(12) United States Patent  
Kodama et al.

(10) Patent No.: US 9,237,854 B2  
(45) Date of Patent: Jan. 19, 2016

(54) VALVE, FLUID CONTROL DEVICE

(71) Applicants: Murata Manufacturing Co., Ltd., Nagaokakyo-shi, Kyoto-fu (JP); OMRON HEALTHCARE Co., Ltd., Muko-shi, Kyoto (JP)

(72) Inventors: Yukiharu Kodama, Nagaokakyo (JP); Atsuhiko Hirata, Nagaokakyo (JP); Yoshihiko Sano, Muko (JP); Toshihiko Ogura, Muko (JP); Yoshiki Doi, Muko (JP)

(73) Assignees: Murata Manufacturing Co., Ltd., Kyoto (JP); OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/570,024

(22) Filed: Dec. 15, 2014

(65) Prior Publication Data

US 2015/0096638 A1    Apr. 9, 2015

Related U.S. Application Data

(60) Division of application No. 13/772,487, filed on Feb. 21, 2013, now Pat. No. 9,033,683, which is a continuation of application No. PCT/JP2012/059620, filed on Apr. 9, 2012.

(30) Foreign Application Priority Data

Apr. 11, 2011  (JP) .................................. 2011-087472

(51) Int. Cl.  
*F04B 43/02*  (2006.01)  
*F16K 7/17*  (2006.01)  
(Continued)

(52) U.S. Cl.  
CPC ............. *A61B 5/0235* (2013.01); *F04B 43/046* (2013.01); *F04B 49/225* (2013.01);  
(Continued)

(58) Field of Classification Search  
CPC ..... F16K 15/14; F16K 15/144; F16K 31/126; F16K 7/14; F16K 7/17; F16K 15/145; F16K 24/04; A61B 5/02; A61B 5/0235; G05D 7/0113; Y10T 137/7836; Y10T 137/87185; Y10T 137/7895; Y10T 137/86019; F04B 49/225; F04B 43/046  
USPC ........ 417/412, 413.1, 413.2, 413.3, 395, 507; 600/490, 498; 137/510, 115.27  
See application file for complete search history.

(56) References Cited

U.S. PATENT DOCUMENTS 1,871,535 A  *  8/1932  Lattner ................... F15B 1/027  
                                              137/115.14  
2,529,028 A  *  11/1950  Landon ................... C02F 1/685  
                                              137/102

(Continued)

OTHER PUBLICATIONS

Kodama et al., "Valve, Fluid Control Device", U.S. Appl. No. 13/772,487, filed Feb. 21, 2013.

*Primary Examiner* — Devon Kramer  
*Assistant Examiner* — Nathan Zollinger  
(74) *Attorney, Agent, or Firm* — Keating & Bennett, LLP

(57) ABSTRACT

In a fluid control device, a check valve includes a first valve housing and a first diaphragm. The first diaphragm defines a first valve chamber and a second valve chamber. An exhaust valve includes a second valve housing and a second diaphragm. The second diaphragm defines a third valve chamber and a fourth valve chamber. The check valve is opened and closed by a difference in pressure between the first valve chamber and the second valve chamber. The exhaust valve is opened and closed by a difference in pressure between the third valve chamber and the fourth valve chamber.

20 Claims, 40 Drawing Sheets

(51) Int. Cl.
  *A61B 5/0235* (2006.01)
  *F04B 43/04* (2006.01)
  *F04B 49/22* (2006.01)
  *F16K 15/14* (2006.01)
  *F16K 24/04* (2006.01)
  *G05D 7/01* (2006.01)

(52) U.S. Cl.
  CPC ............... *F16K 7/17* (2013.01); *F16K 15/145* (2013.01); *F16K 24/04* (2013.01); *G05D 7/0113* (2013.01); *Y10T 137/7836* (2015.04); *Y10T 137/7895* (2015.04); *Y10T 137/86019* (2015.04); *Y10T 137/87185* (2015.04)

(56) References Cited

U.S. PATENT DOCUMENTS

| | | | | |
|---|---|---|---|---|
| 3,076,477 | A * | 2/1963 | Brandenberg | F15B 13/0405 137/625.6 |
| 4,690,171 | A * | 9/1987 | Johnston | A61B 5/0235 137/625.48 |
| 4,794,940 | A * | 1/1989 | Albert | F16K 31/1266 137/1 |
| 5,088,515 | A * | 2/1992 | Kamen | A61M 39/22 137/15.17 |
| 5,660,370 | A * | 8/1997 | Webster | F16K 7/17 137/884 |
| 5,718,567 | A * | 2/1998 | Rapp | F04B 43/043 417/395 |
| 6,033,191 | A * | 3/2000 | Kamper | F04B 43/043 417/322 |
| 6,412,751 | B1 * | 7/2002 | Wang | F15C 5/00 251/331 |
| 6,752,599 | B2 * | 6/2004 | Park | F04B 49/065 417/395 |
| 6,948,918 | B2 * | 9/2005 | Hansen | A61M 5/14224 417/395 |
| 7,018,337 | B2 * | 3/2006 | Hood, Jr. | A61B 5/0235 600/490 |
| 7,637,284 | B1 * | 12/2009 | Feldmeier | F16K 11/20 137/883 |
| 8,038,640 | B2 * | 10/2011 | Orr | A61M 1/106 417/477.2 |
| 2003/0194332 | A1 * | 10/2003 | Jahn | F04B 43/0733 417/395 |
| 2007/0077156 | A1 * | 4/2007 | Orr | F04B 7/02 417/395 |
| 2009/0060750 | A1 * | 3/2009 | Chen | F04B 43/043 417/26 |
| 2013/0255801 | A1 * | 10/2013 | Hirata | F16K 31/126 137/505.14 |

* cited by examiner

VALVE, FLUID CONTROL DEVICE

BACKGROUND OF THE INVENTION

1. Field of the Invention

The present invention relates to a valve suitable for a fluid control device that charges compressed air into an air reservoir and exhausts the air from the air reservoir, and relates to the fluid control device.

2. Description of the Related Art

A conventional electronic sphygmomanometer is disclosed in Japanese Examined Utility Model Application Publication No. 61-32645. This electronic sphygmomanometer is connected to a cuff through an armband rubber tube. This electronic sphygmomanometer stores in a body case: a pressure pump that sends air out to the cuff; a pressure sensor that converts a cuff pressure into an electronic signal; an electromagnetic valve that is opened according to the electric signal, and rapidly reduces the cuff pressure; a constant speed reducing pressure valve that reduces the cuff pressure at a constant speed; and a driver circuit that generates an electric signal and transmits the electric signal to the electromagnetic valve. The pressure sensor, the pressure pump, the electromagnetic valve, and the constant speed reducing pressure valve are connected to one another by one rubber tube, and this one rubber tube is connected to an arm band rubber tube that communicates with the cuff.

In this structure, the electronic sphygmomanometer, when starting blood pressure measurement, sends out air to the cuff by the pumping operation of the pressure pump, and increases the pressure in the cuff. Then, after the blood pressure measurement is completed, the electronic sphygmomanometer energizes the electromagnetic valve, opens the electromagnetic valve, and makes air in the cuff exhaust rapidly. Accordingly, the cuff will be in a state in which the next blood pressure can be measured.

The electronic sphygmomanometer of Japanese Examined Utility Model Application Publication No. 61-32645 requires an electromagnetic valve that is difficult to be miniaturized and a driver circuit that drives the electromagnetic valve. Therefore, the manufacturing costs may become higher, and the main body of the electronic sphygmomanometer may become larger, and the power consumption may increase.

Accordingly, for example, in order to simplify the structure, a typical piezoelectric pump might be connected to a cuff directly. For example, a piezoelectric pump having a pump housing with a pump chamber, a discharge hole, and a suction hole formed inside is prepared; and the discharge hole is connected to the armband rubber tube of the cuff. Then, the piezoelectric pump, when starting blood pressure measurement, performs a pumping operation, sends out air from the discharge hole to the cuff, and increases the pressure in the cuff. Subsequently, after the blood pressure measurement is completed, the piezoelectric pump stops the pumping operation and exhausts the air in the cuff from the suction hole.

However, the volume of the air that can be stored in the cuff is extremely large as compared with the volume of the pump chamber of the piezoelectric pump. Then, the exhaust speed of the piezoelectric pump is extremely slow as compared with the amount of the air that can be stored in the cuff. Therefore, in a case in which the piezoelectric pump is directly connected to the cuff, the air in the cuff cannot be exhausted rapidly.

SUMMARY OF THE INVENTION

Preferred embodiments of the present invention provide a valve suitable for a fluid control device that charges compressed air into an air reservoir and rapidly exhausts the air from the air reservoir, requires low manufacturing costs and small power consumption, and has a small size, and also provide a fluid control device including such a valve.

A valve according to a preferred embodiment of the present invention includes a valve housing including a first ventilation hole, a second ventilation hole, and a third ventilation hole; a diaphragm that divides an inside of the valve housing and defines a first region and a second region in the valve housing, and the diaphragm is fixed to the valve housing so that, in a case in which, in the valve housing, a pressure of the first region that communicates with the first ventilation hole is higher than a pressure of the second region that communicates with the second ventilation hole in the valve housing, the diaphragm makes the first ventilation hole and the second ventilation hole communicate with each other and blocks ventilation between the second ventilation hole and the third ventilation hole; and, in a case in which the pressure of the first region is lower than the pressure of the second region, the diaphragm makes the second ventilation hole and the third ventilation hole communicate with each other and blocks the ventilation between the first ventilation hole and the second ventilation hole.

With this configuration, for example, the pump is connected to the first ventilation hole, the air reservoirs, such as the cuff for blood pressure measurement, are connected to the second ventilation hole, and the third ventilation hole is opened to the atmosphere. In this case, when the pump performs a pumping operation, air will flow from the discharge hole of the pump into the first region in the valve housing through the first ventilation hole. Accordingly, within the valve housing, the pressure of the first region becomes higher than the pressure of the second region, and the first ventilation hole and the second ventilation hole communicate each other; and the ventilation between the second ventilation hole and the third ventilation hole is blocked. As a result, the air is sent out from the pump to the air reservoir through the first ventilation hole and the second ventilation hole, and the pressure (the air pressure) in the air reservoir increases.

Subsequently, after the pump stops the pumping operation, since the volume of the pump chamber and the first region is extremely small as compared with the volume of the air that can be stored in the air reservoir, the air in the pump chamber and the first region is immediately exhausted from the suction hole of the pump to the outside of the pump through the discharge hole of the pump. As a result, within the valve housing, after the pumping operation of the pump stops, the pressure of the first region is immediately reduced lower than the pressure of the second region.

When the pressure of the first region is reduced lower than the pressure of the second region, with this configuration, the second ventilation hole and the third ventilation hole communicate with each other, and the ventilation between the first ventilation hole and the second ventilation hole is blocked. Accordingly, the air in the air reservoir is rapidly exhausted from the third ventilation hole through the second region.

Therefore, by connecting the valve in this configuration to the pump and the air reservoir, compressed air is charged into the air reservoir and the air can be rapidly exhausted from the air reservoir.

The valve housing may preferably include a first valve housing and a second valve housing, wherein the first valve housing and the second valve housing include the first region and the second region defined inside by the diaphragm, respectively; the first valve housing includes the first ventilation hole and the second ventilation hole; the second valve housing includes the third ventilation hole; a fourth ventilation hole that communicates with the first ventilation hole and the first region; and a fifth ventilation hole that communicates with the second ventilation hole and the second region, and the diaphragm is fixed to the first valve housing and the second valve housing so that, in a case in which the pressure of the first region is higher than the pressure of the second region, makes the first ventilation hole and the second ventilation hole communicate with each other and blocks the ventilation between the third ventilation hole and the fifth ventilation hole; and, in a case in which the pressure of the first region is lower than the pressure of the second region, makes the third ventilation hole and the fifth ventilation hole communicate with each other and blocks the ventilation between the first ventilation hole and the second ventilation hole.

With this configuration, when the pump performs the pumping operation, the air will flow from the discharge hole of the pump into the first region in the first valve housing and the second valve housing through the first ventilation hole.

Accordingly, within the first valve housing and the second valve housing, the pressure of the first region becomes higher than the pressure of the second region, and the first ventilation hole and the second ventilation hole communicate with each other, and the ventilation between the second and the fifth ventilation holes and the third ventilation hole is blocked. As a result, the air is sent out from the pump to the air reservoir through the first ventilation hole and the second ventilation hole, and the pressure (the air pressure) in the air reservoir increases.

Subsequently, after the pump stops the pumping operation, as described above, within the first valve housing and the second valve housing, the pressure of the first region is immediately reduced lower than the pressure of the second region. When the pressure of the first region is reduced lower than the pressure of the second region, with this configuration, the second and the fifth ventilation holes and the third ventilation hole communicate with each other, and the ventilation between the first ventilation hole and the second ventilation hole is blocked. Accordingly, the air in the air reservoir is immediately exhausted from the third ventilation hole through the fifth ventilation hole and the second region.

Therefore, by connecting the valve in this configuration to the pump and the air reservoir, compressed air is charged into the air reservoir and the air can be rapidly exhausted from the air reservoir.

The diaphragm may preferably include a first diaphragm that divides an inside of the first valve housing and defines the first region and the second region in the first valve housing; and a second diaphragm that divides an inside of the second valve housing and defines the first region and the second region in the second valve housing, wherein the first diaphragm is fixed to the first valve housing so that, in a case in which the pressure of the first region is higher than the pressure of the second region, the first diaphragm opens the second ventilation hole and makes the first ventilation hole and the second ventilation hole communicate with each other; and, in a case in which the pressure of the first region is lower than the pressure of the second region, seals the second ventilation hole and blocks the ventilation between the first ventilation hole and the second ventilation hole; and the second diaphragm is fixed to the second valve housing so that, in a case in which the pressure of the first region is higher than the pressure of the second region, the second diaphragm seals the third ventilation hole and blocks the ventilation between the third ventilation hole and the fifth ventilation hole; and, in a case in which the pressure of the first region is lower than the pressure of the second region, the second diaphragm opens the third ventilation hole and makes the third ventilation hole and the fifth ventilation hole communicate with each other.

The first valve housing may preferably include a sixth ventilation hole that communicates with the second ventilation hole and the second region, wherein the first diaphragm divides the inside of the first valve housing and defines a first valve chamber that communicates with the first ventilation hole and defines a portion of the first region, and a second valve chamber that communicates with the sixth ventilation hole and defines a portion of the second region.

With this configuration, at a time of performing the pumping operation of the pump, the air that flows out of the second ventilation hole through the first ventilation hole of the first valve housing becomes a pressure slightly lower than the discharge pressure of the piezoelectric pump, and flows from the sixth ventilation hole into the second valve chamber. On the other hand, the discharge pressure of the piezoelectric pump is applied to the first valve chamber. As a result, in the first valve housing, the pressure of the first valve chamber is slightly higher than the pressure of the second valve chamber, and the first diaphragm is kept opened in the first valve housing. In addition, since a difference in pressure between the first valve chamber and the second valve chamber is small, the difference in pressure is not extremely deviated, so that the first diaphragm can be prevented from being damaged.

The first valve housing may preferably include a valve seat that projects from a peripheral end of the second ventilation hole toward the first diaphragm, wherein the first diaphragm is arranged in contact with the valve seat.

The first diaphragm may preferably open and close the valve by contacting or separating from the valve seat by the difference in pressure between the first valve chamber and the second valve chamber.

With this configuration, in a case in which the pressure of the first valve chamber is higher than the pressure of the second valve chamber, the first diaphragm separates from the valve seat and opens the valve. On the contrary, in a case in which the pressure of the second valve chamber is higher than the pressure of the first valve chamber, the first diaphragm contacts the valve seat and closes the valve.

The valve seat may be preferably provided in the first valve housing so as to pressurize the first diaphragm.

With this configuration, in order that the valve seat may give a pressure force to the first diaphragm, the check function of a check valve increases.

The first diaphragm and the second diaphragm preferably include one sheet of a diaphragm sheet.

With this configuration, since the first diaphragm and the second diaphragm preferably include a single diaphragm, the miniaturization of the valve can be attained.

The first valve housing and the second valve housing are preferably provided in one valve housing.

With this configuration, the miniaturization of the valve can be attained by preferably forming the valve housing integrally.

The valve housing may preferably include a communicating hole that communicates with the second ventilation hole and the second region, wherein the diaphragm is fixed to the valve housing so that, in a case in which the pressure of the first region is higher than the pressure of the second region, the diaphragm opens the second ventilation hole and makes the first ventilation hole and the second ventilation hole communicate with each other while sealing the third ventilation hole and blocking the ventilation between the third ventilation hole and the communicating hole; and, in a case in which the pressure of the first region is lower than the pressure of the second region, the diaphragm opens the third ventilation hole and makes the third ventilation hole and the communicating hole communicate with each other while sealing the second ventilation hole and blocking the first ventilation hole and the second ventilation hole.

With this configuration, when the pump performs the pumping operation, air will flow from the discharge hole of the pump into the first region in the valve housing through the first ventilation hole. Accordingly, within the valve housing, the pressure of the first region is higher than the pressure of the second region, the second ventilation hole is opened and the first ventilation hole and the second ventilation hole are communicated with each other while the third ventilation hole is sealed and the ventilation between the third ventilation hole and the communicating hole is blocked. As a result, the air is sent out from the pump to the air reservoir through the first ventilation hole and the second ventilation hole, and the pressure (the air pressure) in the air reservoir increases.

Subsequently, after the pump stops the pumping operation, as described above, within the valve housing, the pressure of the first region is immediately reduced lower than the pressure of the second region. When the pressure of the first region is lower than the pressure of the second region, with this configuration, the third ventilation hole is opened and the third ventilation hole and the communicating hole are communicated with each other while the second ventilation hole is sealed and the ventilation between the first ventilation hole and the second ventilation hole is blocked. Accordingly, the air in the air reservoir is rapidly exhausted from the third ventilation hole through the communicating hole and the second region.

Therefore, by connecting the valve in this configuration to the pump and the air reservoir, compressed air is charged into the air reservoir and the air can be rapidly exhausted from the air reservoir.

The valve housing may preferably include a projecting portion that projects toward the diaphragm in the first region in which the diaphragm includes a hole portion in a portion of a region that is opposed to the projecting portion in which the diaphragm is fixed to the valve housing so that, in a case in which the pressure of the first region is higher than the pressure of the second region, the diaphragm separates a peripheral end of the hole portion from the projecting portion and makes the first ventilation hole and the second ventilation hole communicate with each other, and seals the third ventilation hole and blocks the ventilation between the second ventilation hole and the third ventilation hole; and, in a case in which the pressure of the first region is lower than the pressure of the second region, the diaphragm opens the third ventilation hole and makes the second ventilation hole and the third ventilation hole communicate with each other, and makes the peripheral end of the hole portion abut against the projecting portion and blocks the ventilation between the first ventilation hole and the second ventilation hole.

With this configuration, when the pump performs the pumping operation, air will flow from the discharge hole of the pump into the first region in the valve housing through the first ventilation hole. Accordingly, within the valve housing, the pressure of the first region becomes higher than the pressure of the second region, the first ventilation hole and the second ventilation hole are communicated with each other, the third ventilation hole is sealed, and the ventilation between the second ventilation hole and the third ventilation hole is blocked.

As a result, the air is sent out from the pump to the air reservoir through the first ventilation hole, the hole portion of the diaphragm, and the second ventilation hole, and the pressure (the air pressure) in the air reservoir increases.

Subsequently, after the pump stops the pumping operation, as described above, within the valve housing, the pressure of the first region is immediately reduced lower than the pressure of the second region. When the pressure of the first region is reduced lower than the pressure of the second region, with this configuration, the third ventilation hole is opened, the second ventilation hole and the third ventilation hole are communicated with each other, and the ventilation between the first ventilation hole and the second ventilation hole is blocked.

This enables the air in the air reservoir to be rapidly exhausted from the third ventilation hole through the second ventilation hole and the second region.

Therefore, by connecting the valve in this configuration to the pump and the air reservoir, compressed air is charged into the air reservoir and the air can be rapidly exhausted from the air reservoir.

In addition, a fluid control device according to another preferred embodiment of the present invention preferably has the following configurations.

The fluid control device may preferably include a pump including a pump chamber, and a suction hole and a discharge hole that communicate with each other through the pump chamber; and the valve according to any one of the preferred embodiments described above, wherein the discharge hole of the pump is connected to the first ventilation hole; the pump makes the pressure of the first region higher than the pressure of the second region by performing the pumping operation; and the pump makes the pressure of the first region lower than the pressure of the second region by stopping the pumping operation.

With this configuration, the fluid control device is, for example, an electronic sphygmomanometer. With this configuration, by using any one of the valves according to the preferred embodiments described above, a similar effect is achieved even for a fluid control device equipped with the valve. Furthermore, according to this configuration, an electromagnetic valve which is hard to be miniaturized and a driver circuit that drives the electromagnetic valve are not provided, so that a small and low profile fluid control device can be provided with low manufacturing costs and small power consumption.

It is to be noted that, with this configuration, the pump may include, for example, an actuator of which the peripheral portion is not substantially fixed and which bends and vibrates from the central portion to the peripheral portion; and a flat portion disposed while being close and facing the actuator, and one ventilation hole or a plurality of ventilation holes are formed in an actuator facing region, which faces the actuator, on the flat portion. According to this configuration, since the pump that can achieve a higher pressure and a larger flow rate despite the small size and low profile design is preferably used, a fluid control device that has further smaller size and lower profile design can be provided.

According to various preferred embodiments of the present invention, a valve and a fluid control device can be provided, the valve being suitable for the fluid control device that charges compressed air into an air reservoir and can immediately exhaust the air from the air reservoir, requires low manufacturing costs and small power consumption, and has a small size.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
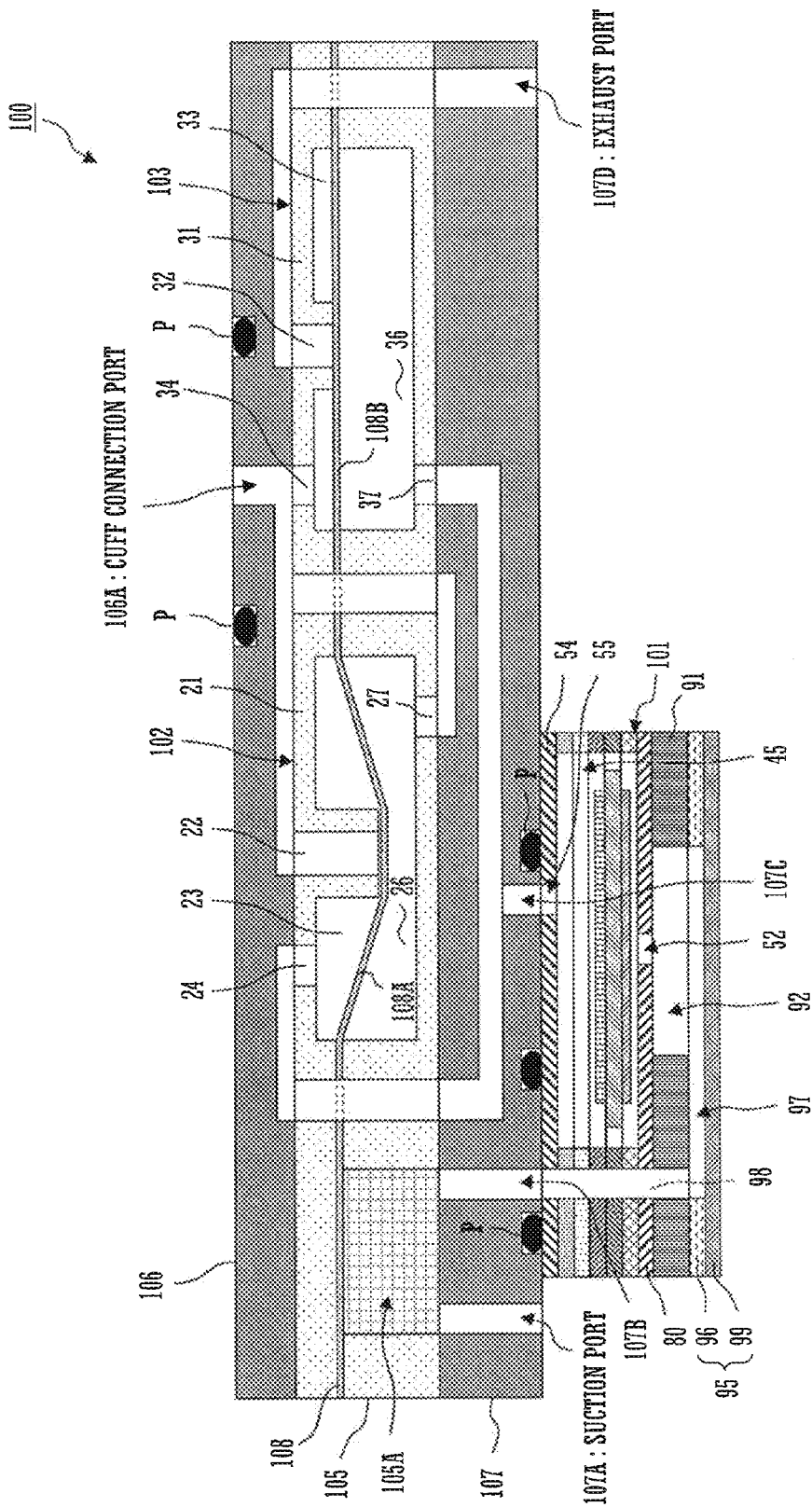
FIG. 1 is a cross sectional view of a main portion of a fluid control device 100 according to a first preferred embodiment of the present invention.
Figure 2:
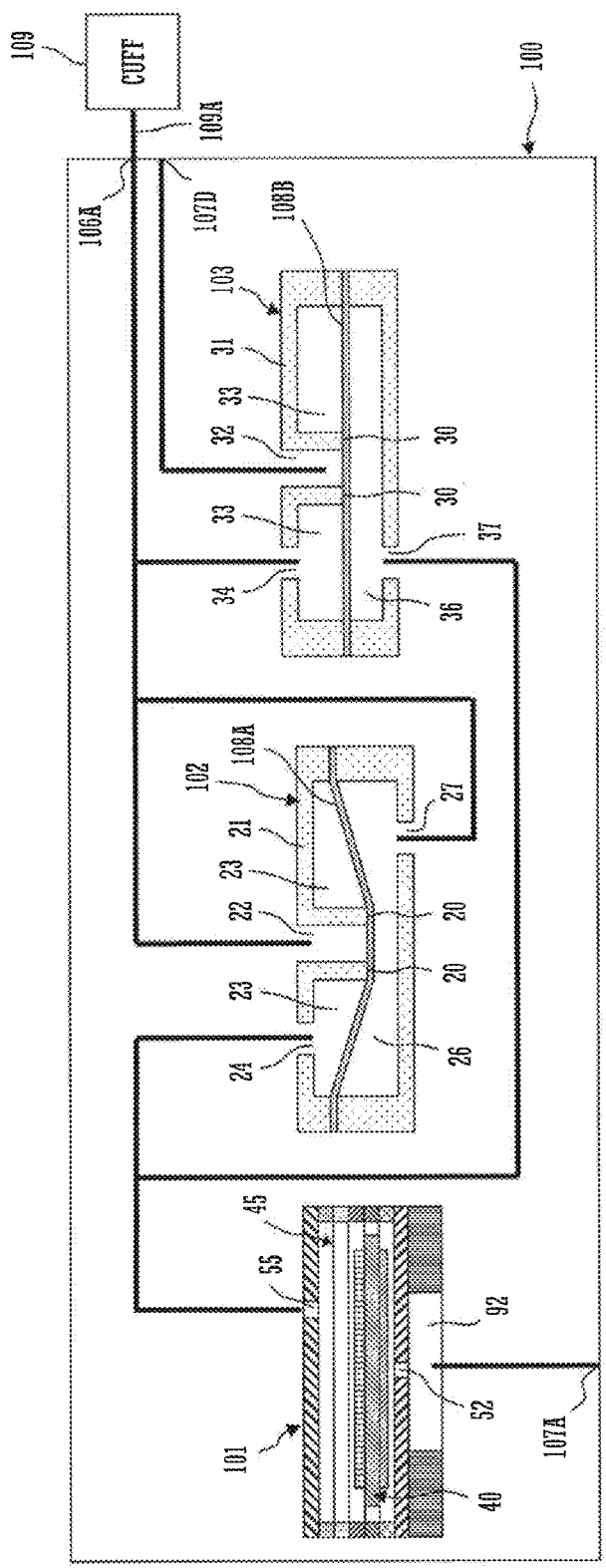
FIG. 2 is an explanatory view showing a connection relationship among a piezoelectric pump 101, a check valve 102, an exhaust valve 103, and a cuff 109 that are shown in FIG. 1.

Hereinafter, a fluid control device 100 according to a first preferred embodiment of the present invention will be described. FIG. 1 is a cross sectional view of the main portion of the fluid control device 100 according to the first preferred embodiment of the present invention. FIG. 2 is an explanatory view showing the connection relationship among a piezoelectric pump 101, a check valve 102, an exhaust valve 103, and a cuff 109 that are shown in FIG. 1. The fluid control device 100 has a structure in which the piezoelectric pump 101, a base plate 107, a valve housing 105 that defines, together with a diaphragm 108, a dustproof filter 105A, the check valve 102, and the exhaust valve 103, and a lid element 106 are laminated in this order. In other words, the piezoelectric pump 101, the check valve 102, and the exhaust valve 103 are preferably formed integrally. With this structure, the fluid control device 100 is equipped with the piezoelectric pump 101, the check valve 102, and the exhaust valve 103.

The lid element 106 includes a cuff connection port 106A that communicates with an arm band rubber tube 109A of the cuff 109. By fitting the arm band rubber tube 109A of the cuff 109 to the cuff connection port 106A of the lid element 106 through a packing P, the fluid control device 100 is connected to the cuff 109.

The base plate 107 includes a suction port 107A that sucks external air, an inflow path 107B that causes the air that has passed the dustproof filter 105A to flow into the piezoelectric pump 101, an outflow path 107C that causes the air sent out from the piezoelectric pump 101 to flow out into the valve housing 105, and an exhaust port 107D that exhausts the air in the cuff 109. By positioning a through hole 98 and a discharge hole 55 of the piezoelectric pump 101 so as to communicate with the inflow path 107B and the outflow path 107C of the base plate 107 and then connecting the piezoelectric pump 101 to the base plate 107 through the packing P, the base plate 107 is connected to the piezoelectric pump 101.

The material of the diaphragm 108 may be an elastic element, such as ethylene propylene rubber or silicone rubber, for example.

In the above structure, the fluid control device 100, although the details will be described later, makes the piezoelectric pump 101 perform the pumping operation when starting blood pressure measurement. Accordingly, the fluid control device 100 sucks external air from the suction port 107A and makes the air flow into a pump chamber 45 in the piezoelectric pump 101 through the dustproof filter 105A. Then, the fluid control device 100 sends out the air from the discharge hole 55 to the cuff 109 through the check valve 102 and increases the pressure (the air pressure) in the cuff 109. Subsequently, after the blood pressure measurement is completed, the fluid control device 100 stops the pumping operation of the piezoelectric pump 101, and makes the air in the cuff 109 exhaust rapidly from the exhaust port 107D through the fourth ventilation hole 34 and the third ventilation hole 32.

It is to be noted that a complex of the check valve 102 and the exhaust valve 103 of the fluid control device 100 shown in FIG. 1 is equivalent to the "valve" according to a preferred embodiment of the present invention.

Here, the structure of the piezoelectric pump 101, the check valve 102, and the exhaust valve 103 is described in detail. To begin with, the structure of the piezoelectric pump 101 is described in detail with reference to FIG. 1, FIG. 3, and FIG. 4.

Figure 3:
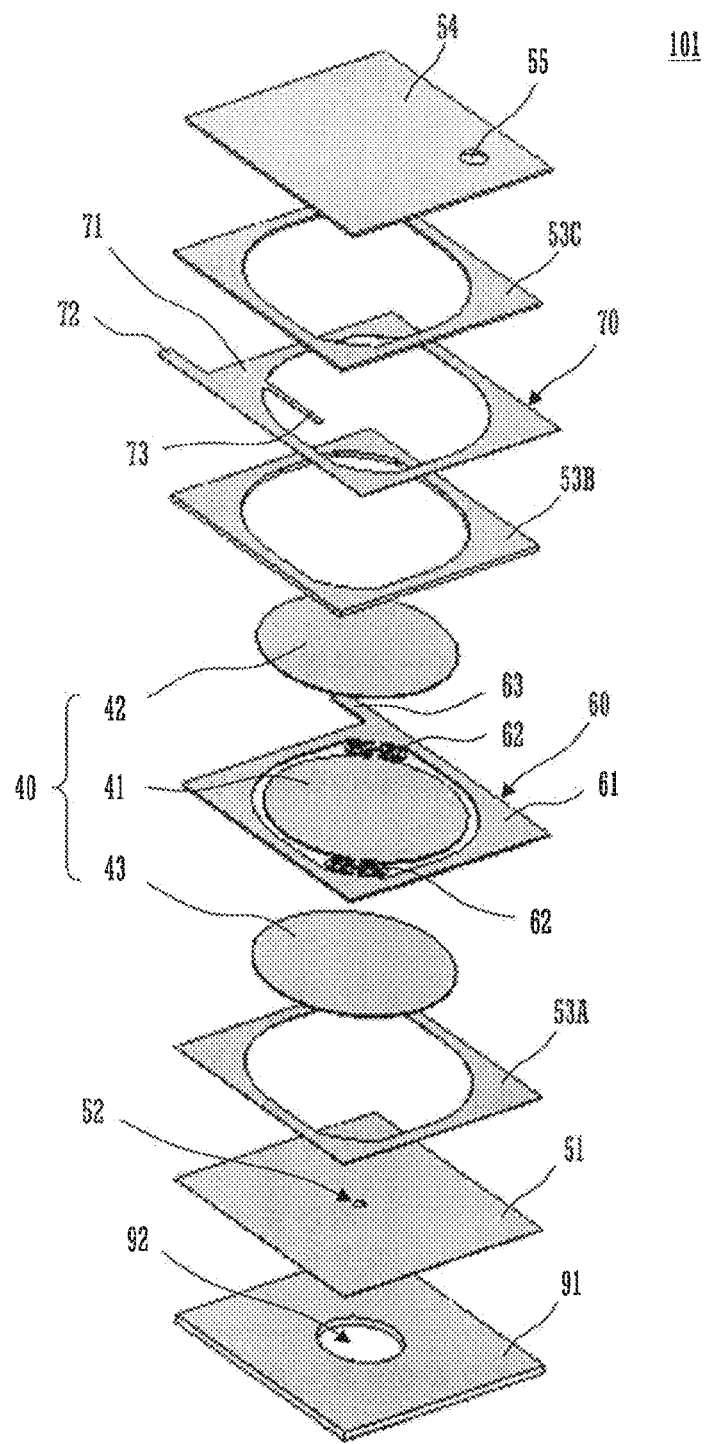
FIG. 3 is an exploded perspective view of a main portion of the piezoelectric pump 101 shown in FIG. 1.
Figure 4:
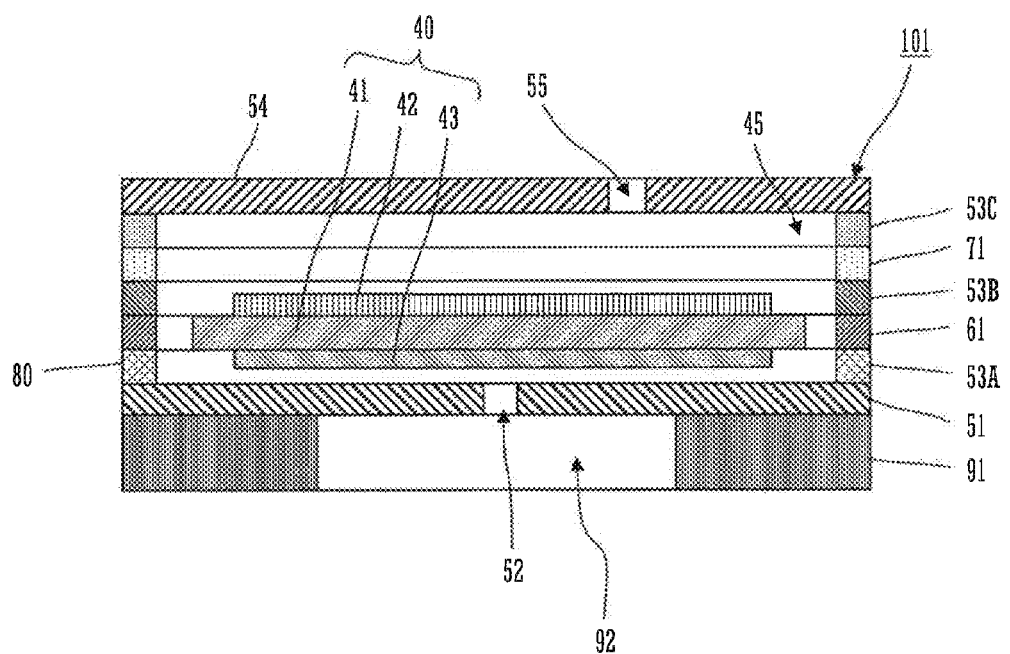
FIG. 4 is a cross sectional view of the main portion of the piezoelectric pump 101 shown in FIG. 1.

FIG. 3 is an exploded perspective view of the main portion of the piezoelectric pump 101 shown in FIG. 1, and FIG. 4 is a cross sectional view of the main portion of the piezoelectric pump 101 shown in FIG. 1. The piezoelectric pump 101 preferably includes a base plate 91, a flat portion 51, a spacer 53A, a reinforcement plate 43, a vibrating plate unit 60, a piezoelectric element 42, a spacer 53B, an electrode conducting plate 70, a spacer 53C, and a lid portion 54, and has a structure in which the above mentioned elements are laminated in order.

The piezoelectric element 42 is attached onto the upper surface of a disc shaped vibrating plate 41; the reinforcement plate 43 is attached onto the lower surface of the vibrating plate 41; and the vibrating plate 41, the piezoelectric element 42, and the reinforcement plate 43 define an actuator 40. Here, the vibrating plate 41 preferably includes a metal plate that has a coefficient of linear expansion greater than the coefficients of linear expansion of the piezoelectric element 42 and the reinforcement plate 43 and cured by applying heat at a time of adhesion, so that the entirety does not bend and an appropriate compressive stress can be left on the piezoelectric element 42, which prevents the piezoelectric element 42 from cracking. For example, the vibrating plate 41 may be preferably made of a material having a greater coefficient of linear expansion such as phosphor bronze (C5210) and stainless steel SUS301, and the reinforcement plate 43 may be preferably formed of 42 nickel, 36 nickel, stainless steel SUS430 or other suitable material. In this case, the thickness of the spacer 53B may preferably be the same as or slightly thicker than the thickness of the piezoelectric element 42. It should be noted that the vibrating plate 41, the piezoelectric element 42, and the reinforcement plate 43 may be arranged from the top in order of the piezoelectric element 42, the reinforcement plate 43, and the vibrating plate 41. Also in this case, the coefficient of linear expansion is adjusted by interchanging the materials between the reinforcement plate 43 and the vibrating plate 41 so as to leave the appropriate compressive stress on the piezoelectric element 42.

A vibrating plate support frame 61 is provided around the vibrating plate 41, and the vibrating plate 41 is linked to the vibrating plate support frame 61 by a link portion 62. The link portion 62 preferably has a thin ring shape and has an elastic structure having the elasticity of a small spring constant. Therefore, the vibrating plate 41 is flexibly supported preferably at two points against the vibrating plate support frame 61 by the two link portions 62. For this reason, the bending vibration of the vibrating plate 41 is not practically blocked. In other words, the peripheral portion of the actuator 40 (as well as the central portion) is not substantially fixed. It is to be noted the spacer 53A is provided in order to hold the actuator 40 while keeping a constant gap to the flat portion 51. The vibrating plate support frame 61 includes an external terminal 63 for electrical connection.

The vibrating plate 41, the vibrating plate support frame 61, the link portion 62, and the external terminal 63 are molded through a stamping process of a metal plate, and these elements define a vibrating plate unit 60.

The spacer 53B made of a resin material is adhesively fixed onto the upper surface of the vibrating plate support frame 61. The thickness of the spacer 53B is preferably the same as or slightly thicker than the thickness of the piezoelectric element 42, and the spacer 53B defines a portion of the pump housing 80 and electrically insulates the electrode conducting plate 70, described below, with the vibrating plate unit 60.

The electrode conducting plate 70 made of a metal material is adhesively fixed on the spacer 53B. The electrode conducting plate 70 includes a frame portion 71 that is a nearly circular opening, an inner terminal 73 that projects into the opening, and an external terminal 72 that projects into the outside.

The leading edge of the inner terminal 73 is soldered onto the surface of the piezoelectric element 42. The vibration of the inner terminal 73 can be significantly reduced and prevented by setting a soldering position to a position equivalent to a node of the bending vibration of the actuator 40.

The spacer 53C made of a resin material is adhesively fixed on the electrode conducting plate 70. The spacer 53C, in this preferred embodiment, preferably has a thickness that is similar to the thickness of the piezoelectric element 42. The spacer 53C is a spacer that prevents the soldered portion of the inner terminal 73 from contacting the lid portion 54 when the actuator vibrates.

The spacer 53C also prevents the surface of the piezoelectric element 42 from excessively approaching to the lid portion 54 so as to prevent vibration amplitude by air resistance from reducing. Therefore, the thickness of the spacer 53C may preferably be similar to the thickness of the piezoelectric element 42 as stated above.

The lid portion 54 is located on the upper portion of the spacer 53C and covers the surroundings of the actuator 40. For that reason, the fluid sucked in through a central ventilation hole 52 is discharged from the discharge hole 55. While the discharge hole 55 may be provided in the center of the lid portion 54, the discharge hole 55 that releases positive pressure in the pump housing 80 including the lid portion 54 need not necessarily be provided in the center of the lid portion 54.

On the other hand, a central ventilation hole 52 (a suction hole) is preferably located in the center or approximate center of the flat portion 51. Between the flat portion 51 and the vibrating plate unit 60, the spacer 53A is inserted, the spacer 53A having a thickness obtained by adding approximately several 10 micrometers to the thickness of the reinforcement plate 43. In this way, even if the spacer 53A exists, since the vibrating plate 41 is not necessarily fixed by the vibrating plate support frame 61, a gap varies automatically according to load fluctuation. However, since the fixed link portion 62 gives some influence, by inserting the spacer 53A in this way, a gap can be ensured positively and a flow rate can be increased at low load time. In addition, even in a case in which the spacer 53A is inserted, the link portion 62 bends at high load time, the gap of region as opposed to the actuator 40 and the flat portion 51 decreases automatically, which makes operation by high pressure possible.

It is to be noted that, while the link portion 62 is provided at two spots in the example shown in FIG. 3, the link portion 62 may be provided at not less than three spots. Since the link portion 62 is not designed to block the vibration of the actuator 40, but gives some influence to the vibration, by linking (holding) at three spots, for example, a more natural hold becomes possible, which can prevent the piezoelectric element from cracking.

The base plate 91 including a cylindrical or substantially cylindrical opening 92 preferably located in the center or approximate center is provided in the lower portion of the flat portion 51. A portion of the flat portion 51 is exposed at the opening 92 of the base plate 91. This circularly exposed portion can vibrate at a frequency substantially the same as a frequency of the actuator 40 by pressure fluctuation accompanying the vibration of the actuator 40. By the configuration of the flat portion 51 and the base plate 91, a portion that is positioned in the center or around the center of an actuator facing region of the flat portion 51 is a thin plate portion that can bend and vibrate, and a peripheral portion is a thick plate portion that is fixed substantially. This characteristic frequency of the circularly thin plate portion is designed to be the same as or slightly lower than the driving frequency of the actuator 40. Accordingly, in response to the vibration of the actuator 40, the exposed portion of the flat portion 51 centering on the central ventilation hole 52 also vibrates with large amplitude. If the vibration phase of the flat portion 51 is a vibration phase delayed (90-delayed, for example) from the vibration phase of the actuator 40, the thickness fluctuation of a gap space between the flat portion 51 and the actuator 40 increases substantially. As a result, the pump performance can be improved.

In the lower portion of the base plate 91, a cover plate portion 95 is provided as shown in FIG. 1. The cover plate portion 95 is formed preferably by bonding a flow path plate 96 and a cover plate 99 together, for example. In addition, the pump housing 80 includes a through hole 98. Consequently, the piezoelectric pump 101 has a shape in which an L character shaped communicating hole 97 that makes the inflow path 107B and the opening 92 communicate with each other is provided.

Figure 5:
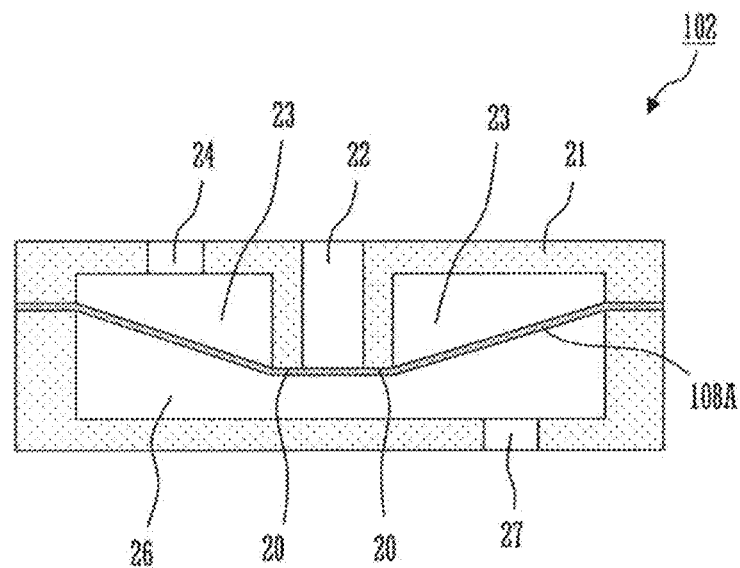
FIG. 5 is a cross sectional view of a main portion of the check valve 102 shown in FIG. 1.

Next, the structure of the check valve 102 is described in detail. FIG. 5 is a cross sectional view of the main portion of the check valve 102 provided in the fluid control device 100 according to the first preferred embodiment of the present invention. The check valve 102 includes a cylindrical or substantially cylindrical first valve housing 21 and a first diaphragm 108A that includes a circular or substantially circular thin film.

The first valve housing 21 includes a first ventilation hole 24 that communicates with a discharge hole 55 of the piezoelectric pump 101, a second ventilation hole 22 that communicates with the cuff 109, a sixth ventilation hole 27 that communicates with the second ventilation hole 22 and the cuff 109, and a valve seat 20 that is projected from the peripheral end of the second ventilation hole 22 to the first diaphragm 108A side.

The first diaphragm 108A contacts the valve seat 20 and is fixed to the first valve housing 21. Accordingly, the first diaphragm 108A divides the inside of the first valve housing 21 and defines a ring shaped first valve chamber 23 that communicates with the first ventilation hole 24, and the second valve chamber 26 that communicates with the sixth ventilation hole 27. The valve seat 20 is arranged in the first valve housing 21 so as to pressurize the first diaphragm 108A.

In the above structure, the check valve 102 opens and closes the valve when the first diaphragm 108A contacts or separates from the valve seat 20 by a difference in pressure between the first valve chamber 23 and the second valve chamber 26.

Figure 6:
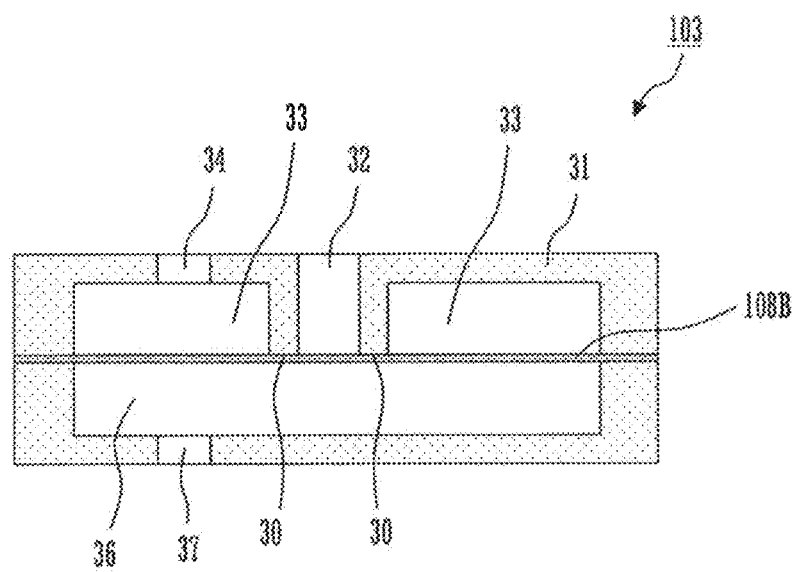
FIG. 6 is a cross sectional view of a main portion of the exhaust valve 103 shown in FIG. 1.

Subsequently, the structure of the exhaust valve 103 is described in detail. FIG. 6 is a cross sectional view of the main portion of the exhaust valve 103 provided in the fluid control device 100 according to the first preferred embodiment of the present invention. The exhaust valve 103 includes a cylindrical or substantially cylindrical second valve housing 31 and a second diaphragm 108B that includes a circular or substantially circular thin film.

The second valve housing 31 includes a third ventilation hole 32 that communicates with the outside of the fluid control device 100; a fifth ventilation hole 37 that communicates with the discharge hole 55 of the piezoelectric pump 101, and the first ventilation hole 24; a fourth ventilation hole 34 that communicates with the cuff 109, the second ventilation hole 22, and the sixth ventilation hole 27; and a valve seat 30 that is projected from the peripheral end of the third ventilation hole 32 to the second diaphragm 108B side.

The second diaphragm 108B contacts the valve seat 30 and is fixed to the second valve housing 31. Accordingly, the second diaphragm 108B divides the inside of the second valve housing 31 and defines a ring shaped third valve chamber 33 that communicates with the fourth ventilation hole 34, and a fourth valve chamber 36 that communicates with the fifth ventilation hole 37.

In the above structure, the exhaust valve 103 opens and closes the valve when the second diaphragm 108B contacts or separates from the valve seat 30 by a difference in pressure between the third valve chamber 33 and the fourth valve chamber 36.

It should be noted, in the present preferred embodiment, the first valve chamber 23 and the fourth valve chamber 36 are equivalent to the "first region" according to a preferred embodiment of the present invention, and the second valve chamber 26 and the third valve chamber 33 are equivalent to the "second region" according to a preferred embodiment of the present invention.

Figure 7:
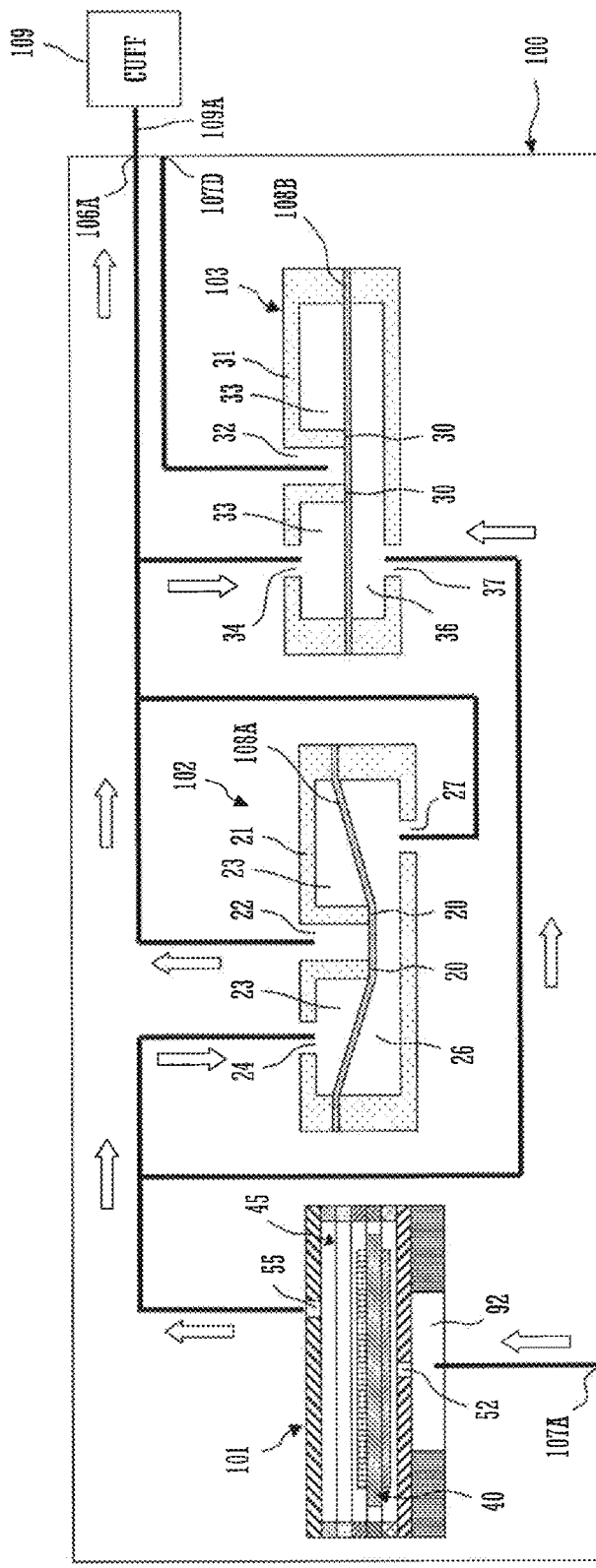
FIG. 7 is an explanatory view showing a flow of air when the piezoelectric pump 101 shown in FIG. 1 is performing a pumping operation.
Figure 8:
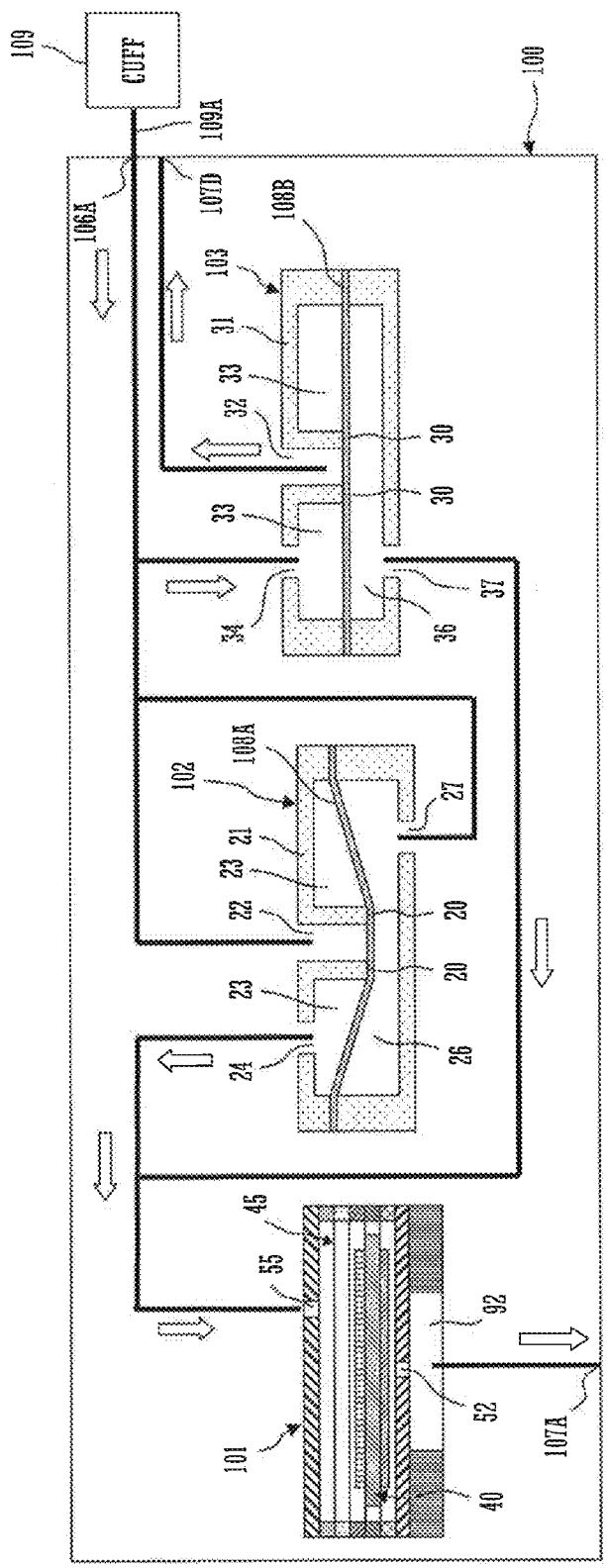
FIG. 8 is an explanatory view showing a flow of air immediately after the piezoelectric pump 101 shown in FIG. 1 stops the pumping operation.
Figure 9:
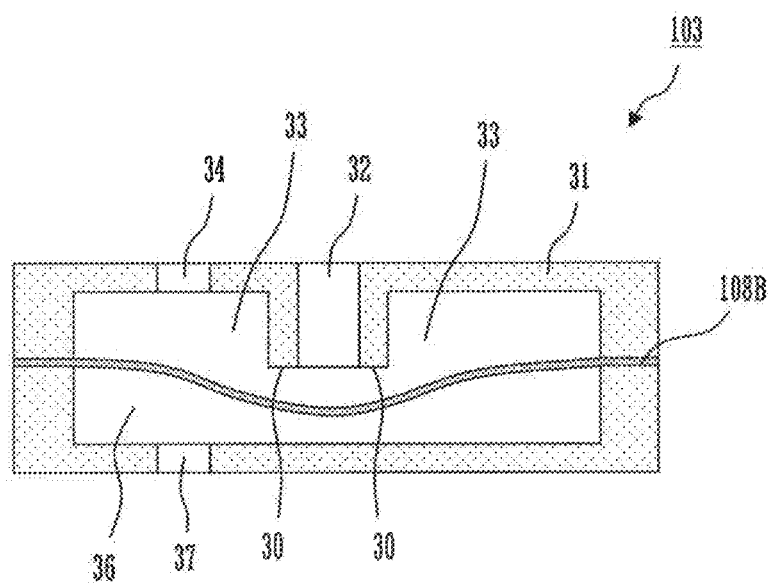
FIG. 9 is a cross sectional view of the main portion when a valve of the exhaust valve 103 shown in FIG. 1 opens.
Figure 10:
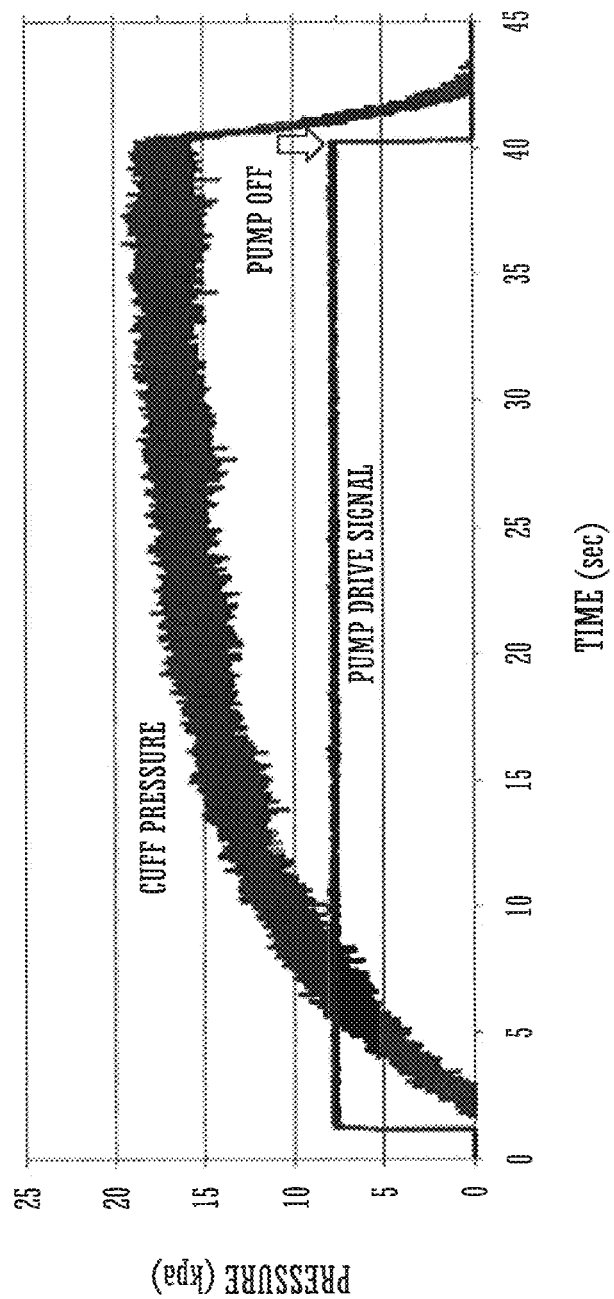
FIG. 10 is a graph showing a change in pressure of the cuff 109 in a state in which the piezoelectric pump 101 shown in FIG. 1 is driven.
Figure 11:
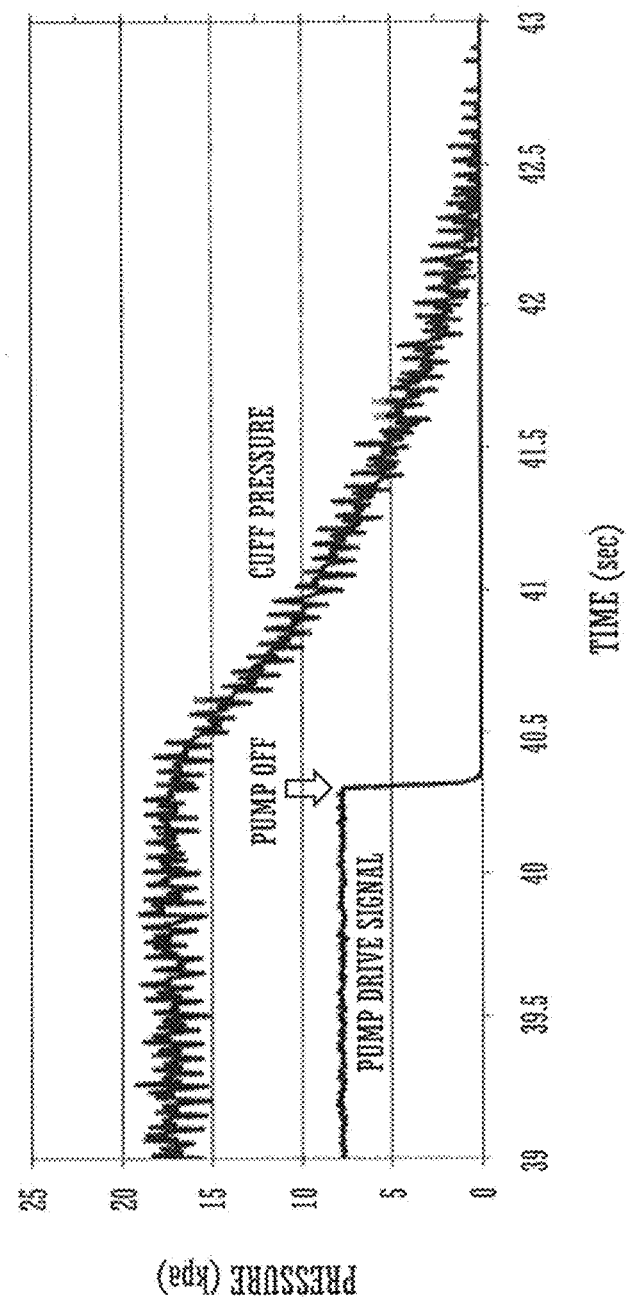
FIG. 11 is a graph showing an enlarged section from Time 39 seconds to Time 43 seconds that are shown in FIG. 10.
Figure 12:
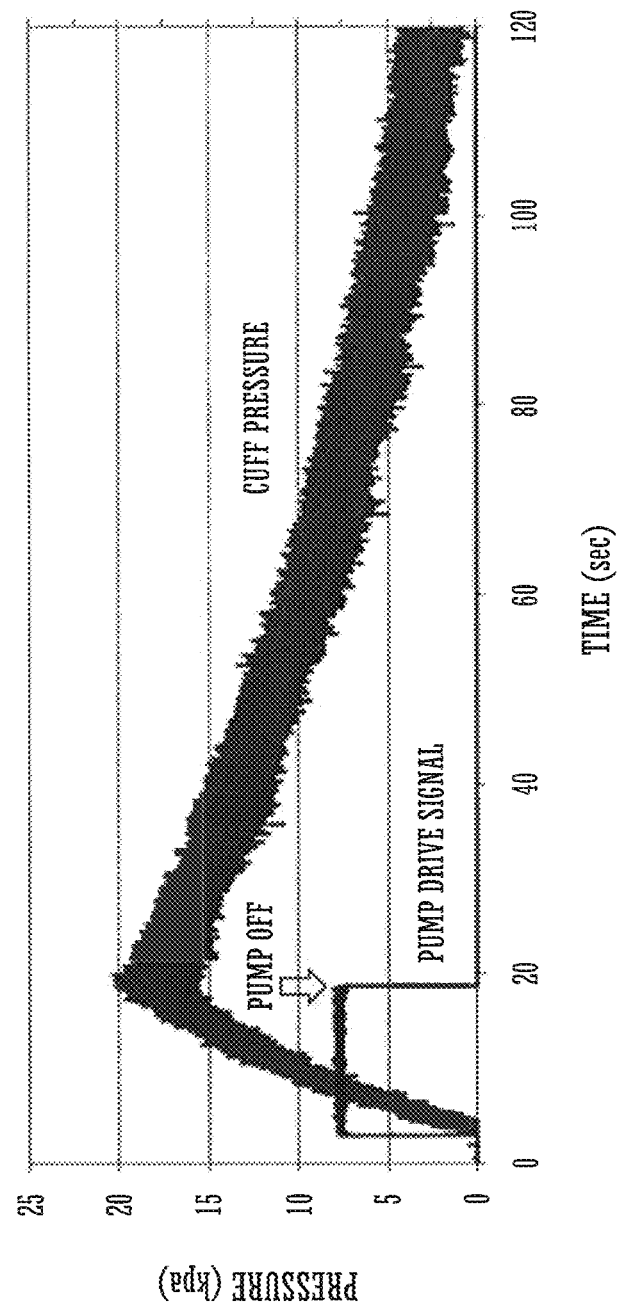
FIG. 12 is a graph showing a change in pressure of the cuff 109 in a state in which the piezoelectric pump 101 is driven when the piezoelectric pump 101 is directly connected to the cuff 109.

Here, the operation of the fluid control device 100 at the time of blood pressure measurement will be described. FIG. 7 is an explanatory view showing a flow of air when the piezoelectric pump 101 shown in FIG. 1 is performing a pumping operation. FIG. 8 is an explanatory view showing a flow of air immediately after the piezoelectric pump 101 shown in FIG. 1 stops the pumping operation. FIG. 9 is a cross sectional view of the main portion of the exhaust valve 103 at a time of opening the valve, provided in the fluid control device 100 according to the first preferred embodiment of the present invention. FIG. 10 is a graph showing a change in pressure of the cuff 109 in a state in which the piezoelectric pump 101 shown in FIG. 1 is driven. FIG. 11 is a graph showing an enlarged section from Time 39 seconds to Time 43 seconds that are shown in FIG. 10. FIG. 12 is a graph showing a change in pressure of the cuff 109 in a state in which the piezoelectric pump 101 is driven when the discharge hole 55 of the piezoelectric pump 101 is directly connected to the cuff 109.

The fluid control device 100 makes the piezoelectric pump 101 perform the pumping operation when starting the blood pressure measurement. Accordingly, the piezoelectric pump 101 sucks external air from the suction port 107A and makes the air flow into the pump chamber 45 in the piezoelectric pump 101 through the dustproof filter 105A (see FIG. 1). Then, the piezoelectric pump 101 makes the air flow from the discharge hole 55 of the piezoelectric pump 101 into the check valve 102. In the check valve 102, the discharge pressure in the forward direction from the first ventilation hole 24 to the second ventilation hole 22 is generated by the pumping operation of the piezoelectric pump 101, so that the pressure of the first valve chamber 23 becomes higher than the pressure of the second valve chamber 26. Accordingly, the first diaphragm 108A opens and makes the first ventilation hole 24 and the second ventilation hole 22 communicate with each other. In addition, in the exhaust valve 103, the pressure of the fourth valve chamber 36 rises by the pumping operation of the piezoelectric pump 101, so that the pressure of the fourth valve chamber 36 becomes higher than the pressure of the third valve chamber 33. Accordingly, the second diaphragm 108B seals the third ventilation hole 32 and blocks out ventilation between the fourth ventilation hole 34 and the second ventilation hole 22, and the third ventilation hole 32. As a result, the air is sent out from the piezoelectric pump 101 to the cuff 109 through the first ventilation hole 24 and the second ventilation hole 22 of the check valve 102 (see FIG. 7), and the pressure (the air pressure) in the cuff 109 increases.

It should be noted the fluid control device 100 has a structure in which the second ventilation hole 22 and the sixth ventilation hole 27 of the check valve 102 communicate with each other. In addition, the check valve 102 has a shape in which the first ventilation hole 24 is arranged in the outer periphery, centering on the second ventilation hole 22. Accordingly, the air that flows out of the second ventilation hole 22 through the first ventilation hole 24 of the check valve 102 becomes a pressure slightly lower than the discharge pressure of the piezoelectric pump 101 and flows from the sixth ventilation hole 27 into the second valve chamber 26. On the other hand, the discharge pressure of the piezoelectric pump 101 is applied to the first valve chamber 23. As a result, in the check valve 102, the pressure of the first valve chamber 23 is slightly higher than the pressure of the second valve chamber 26, and the first diaphragm 108A is kept open in the check valve 102. Additionally, since the difference in pressure between the first valve chamber 23 and the second valve chamber 26 is small, the difference in pressure is not extremely deviated, so that the first diaphragm 108A can be prevented from being damaged.

Moreover, the fluid control device 100 has a structure in which the second ventilation hole 22 of the check valve 102 and the fourth ventilation hole 34 of the exhaust valve 103 communicate with each other. In addition, the exhaust valve 103 has a shape in which the fourth ventilation hole 34 is arranged in the outer periphery, centering on the third ventilation hole 32. Accordingly, the air that flows out of the second ventilation hole 22 through the first ventilation hole 24 of the check valve 102 becomes a pressure slightly lower than the discharge pressure of the piezoelectric pump 101 and flows from the fourth ventilation hole 34 into the third valve chamber 33 of the exhaust valve 103. On the other hand, the discharge pressure of the piezoelectric pump 101 is applied to the fourth valve chamber 36. As a result, in the exhaust valve 103, the pressure of the fourth valve chamber 36 is slightly higher than the pressure of the third valve chamber 33, and the second diaphragm 108B is kept close in the exhaust valve 103. In addition, since the difference in pressure between the fourth valve chamber 36 and the third valve chamber 33 is small, the difference in pressure is not extremely deviated, so that the second diaphragm 108B can be prevented from being damaged.

Subsequently, after the blood pressure measurement is completed, the fluid control device 100 stops the pumping operation of the piezoelectric pump 101. Here, the volume of the pump chamber 45, the first valve chamber 23, and the fourth valve chamber 36 is extremely small as compared with the volume of the air that can be stored in the cuff 109. Therefore, when the pumping operation of the piezoelectric pump 101 stops, the air in the pump chamber 45, the first valve chamber 23, and the fourth valve chamber 36 is immediately exhausted from the suction port 107A of the fluid control device 100 to the outside of the fluid control device 100 through the central ventilation hole 52 and the opening 92 of the piezoelectric pump 101. In addition, the pressure of the cuff 109 is applied to the second valve chamber 26 and the third valve chamber 33. As a result, in the check valve 102, after the pumping operation of the piezoelectric pump 101 stops, the pressure of the first valve chamber 23 is immediately reduced lower than the pressure of the second valve chamber 26. Similarly, in the exhaust valve 103, after the pumping operation of the piezoelectric pump 101 stops, the pressure of the fourth valve chamber 36 is immediately reduced lower than the pressure of the third valve chamber 33.

In the check valve 102, when the pressure of the first valve chamber 23 is reduced lower than the pressure of the second valve chamber 26, the first diaphragm 108A abuts against the valve seat 20 and seals the second ventilation hole 22. In addition, in the exhaust valve 103, when the pressure of the fourth valve chamber 36 is reduced lower than the pressure of the third valve chamber 33, as shown in FIG. 9, the second diaphragm 108B opens and makes the fourth ventilation hole 34 and the third ventilation hole 32 communicate with each other. This enables the air in the cuff 109 to be rapidly exhausted from the exhaust port 107D through the fourth ventilation hole 34 and the third ventilation hole 32 (see FIG. 10 and FIG. 11). FIG. 10 and FIG. 11 show the exhaustion of the air in the cuff 109 will be completed in two seconds after the pumping operation of the piezoelectric pump 101 is stopped.

On the other hand, as a comparative example, in a case of FIG. 12 showing a change in pressure of the cuff 109 in a state in which the piezoelectric pump 101 is driven when the discharge hole 55 of the piezoelectric pump 101 is directly connected to the cuff 109, it is shown that it takes 100 seconds after the pumping operation of the piezoelectric pump 101 is stopped until the exhaust of the air in the cuff 109 is completed, that is, until the cuff 109 can measure next blood pressure.

In other words, in a case in which the fluid control device 100 of the present preferred embodiment is connected to the cuff 109, as compared with a case in which the piezoelectric pump 101 is directly connected to the cuff 109, it became clear that even 98 seconds can be reduced after the blood pressure measurement is completed until the cuff 109 can measure next blood pressure.

Therefore, by connecting the pump 101 and the cuff 109 to the check valve 102 and the exhaust valve 103 of the present preferred embodiment, compressed air can be charged into the cuff 109, and the air can be rapidly discharged from the cuff 109. In addition, by using the check valve 102 and the exhaust valve 103 of the present preferred embodiment, the fluid control device 100 equipped with the check valve 102 and the exhaust valve 103 can also achieve a similar effect. Moreover, according to the present preferred embodiment, an electromagnetic valve which is hard to be miniaturized and a driver circuit that drives the electromagnetic valve are not provided, so that a small and low profile fluid control device 100 can be provided with low manufacturing costs and small power consumption.

It is to be noted while the actuator having a unimorph type structure and undergoing bending vibration was preferably provided in the above described preferred embodiment, it may be possible to attach a piezoelectric element on both sides of the vibrating plate so as to have a bimorph type structure and undergo bending vibration.

Furthermore, in the above described preferred embodiment, while the valve seat 20 of the check valve 102 is preferably provided in the peripheral end of the second ventilation hole 22, the valve seat 20 may be provided in the peripheral end of the first ventilation hole 24 in the event of the operation. Similarly, while the valve seat 30 of the exhaust valve 103 is preferably provided in the peripheral end of the third ventilation hole 32, the valve seat 30 may be provided in the peripheral end of the fourth ventilation hole 34 in the event of the operation.

Additionally, in the above described preferred embodiment, while the exhaust valve 103 connects the fourth ventilation hole 34 to the cuff 109 and connects the third ventilation hole 32 to the exhaust port 107D, in the event of the operation, the exhaust valve 103 may connect the fourth ventilation hole 34 located in the position of the third ventilation hole 32 of FIG. 2 to the cuff 109, and may connect the third ventilation hole 32 located in the position of the fourth ventilation hole 34 of FIG. 2 to the exhaust port 107D. In this connection method, even in a case in which the pressure of the cuff 109 varies due to a body motion and the like, an advantage that unintended exhaust is unlikely to occur is attained.

Moreover, in the above described preferred embodiment, while the diaphragm 108A that preferably includes a circular or substantially circular thin film as a valve element of the check valve 102 is preferably used, other shapes (such as a mushroom shape, a rectangular or substantially rectangular shape, for example) capable of sealing the valve seat 20 may be used.

Subsequently, hereinafter, a fluid control device 200 according to a second preferred embodiment of the present invention will be described. This second preferred embodiment is different from the above described first preferred embodiment in that the check valve 102 and the exhaust valve 103 that are shown in FIG. 2 are replaced with a valve 203 and is preferably the same or substantially the same as the above described first preferred embodiment in other configurations.

Figure 13:
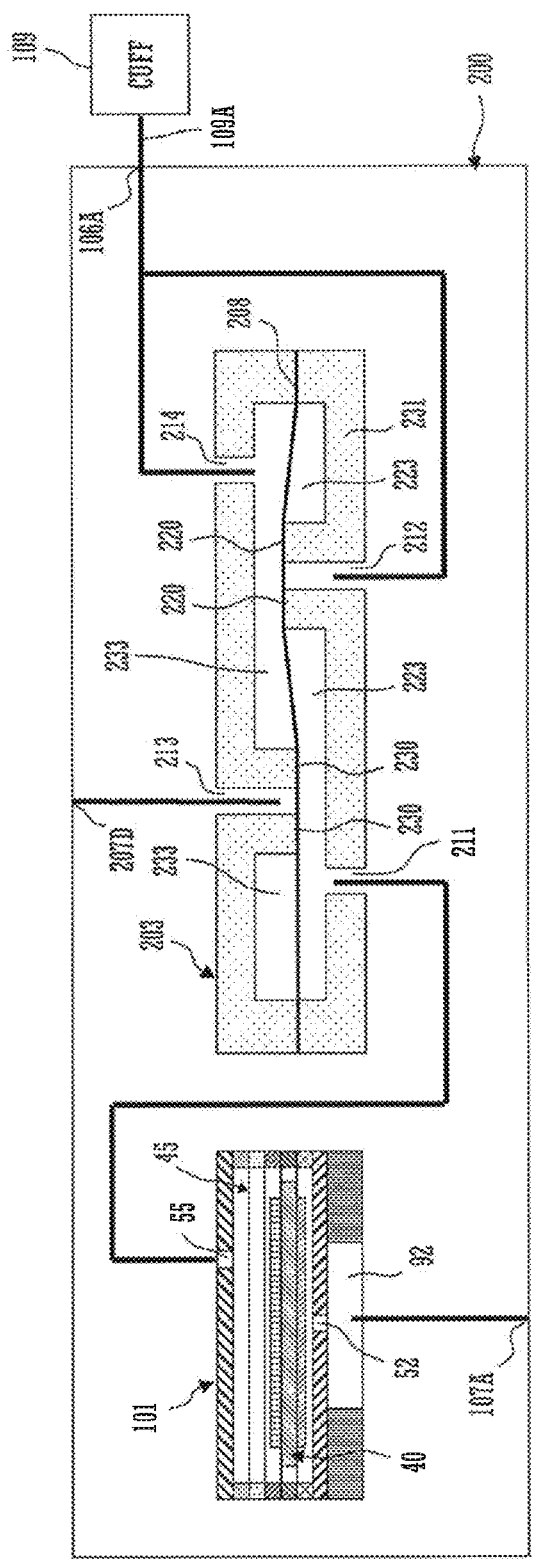
FIG. 13 is an explanatory view showing a connection relationship among a piezoelectric pump 101, a valve 203, and a cuff 109 that are included in a fluid control device 200 according to a second preferred embodiment of the present invention.

To begin with, the structure of the valve 203 will be described. FIG. 13 is an explanatory view showing a connection relationship among a piezoelectric pump 101, the valve 203, and a cuff 109 that are included in a fluid control device 200 according to a second preferred embodiment of the present invention. The valve 203 is an integrated valve that preferably includes the check valve 102 and the exhaust valve 103 that are shown in FIG. 2, and includes a cylindrical or substantially cylindrical valve housing 231 and a diaphragm 208 including a circular or substantially circular thin film.

The valve housing 231 includes a first ventilation hole 211 that communicates with the discharge hole 55 of the piezoelectric pump 101; a second ventilation hole 212 that communicates with the cuff 109; a third ventilation hole 213 that communicates with the outside of the fluid control device 200; a communicating hole 214 that communicates with the second ventilation hole 212 and the cuff 109; a valve seat 220 that is projected from the peripheral end of the second ventilation hole 212 to the diaphragm 208 side; and a valve seat 230 that is projected from the peripheral end of the third ventilation hole 213 to the diaphragm 108 side.

The diaphragm 208 contacts the valve seats 220 and 230 and is fixed to the valve housing 231. Accordingly, the diaphragm 208 divides the inside of the valve housing 231 and forms a ring shaped lower valve chamber 223 that communicates with the first ventilation hole 211, and the ring shaped upper valve chamber 233 that communicates with a communicating hole 214. The valve seat 220 is arranged in the valve housing 231 so as to pressurize the diaphragm 208.

In the above structure, the valve 203 opens and closes the valve when the diaphragm 208 contacts or separates from the valve seat 220 by a difference in pressure between the lower valve chamber 223 and the upper valve chamber 233. In addition, the valve 203 opens and closes the valve when the diaphragm 208 contacts or separates from the valve seat 230 by the difference in pressure between the upper valve chamber 233 and the lower valve chamber 223.

It should be noted, in the present preferred embodiment, the lower valve chamber 223 is equivalent to the "first region" according to a preferred embodiment of the present invention, and the upper valve chamber 233 is equivalent to the "second region" according to a preferred embodiment of the present invention.

Figure 14:
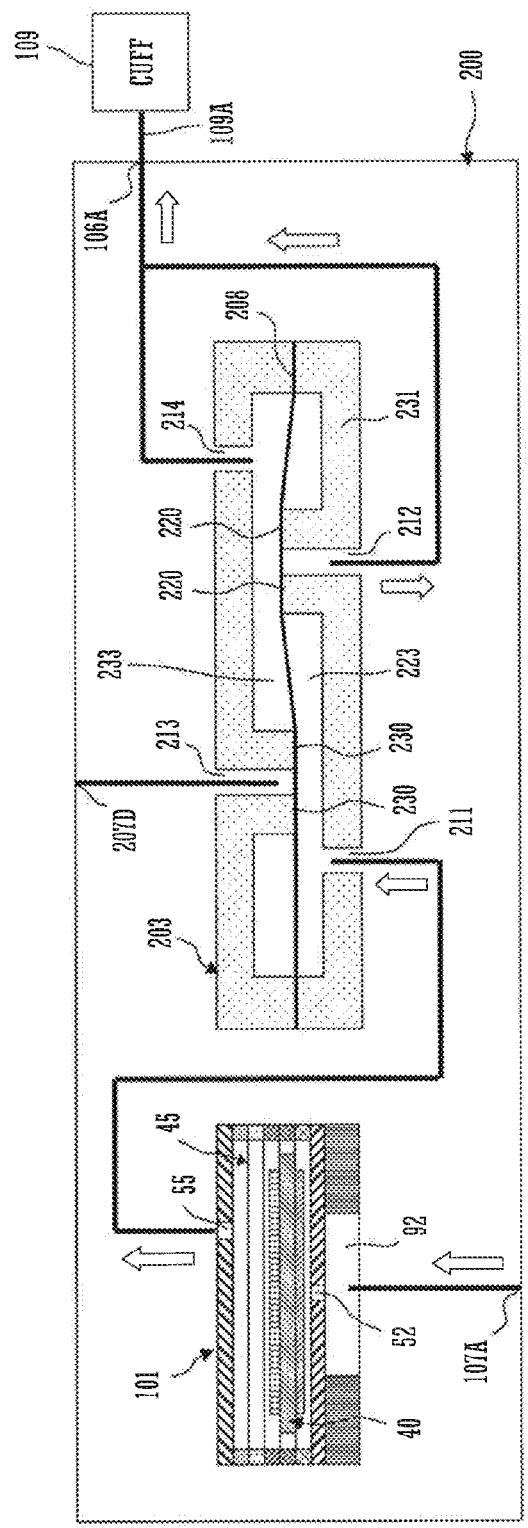
FIG. 14 is an explanatory view showing a flow of air when the piezoelectric pump 101 shown in FIG. 13 is performing a pumping operation.
Figure 15:
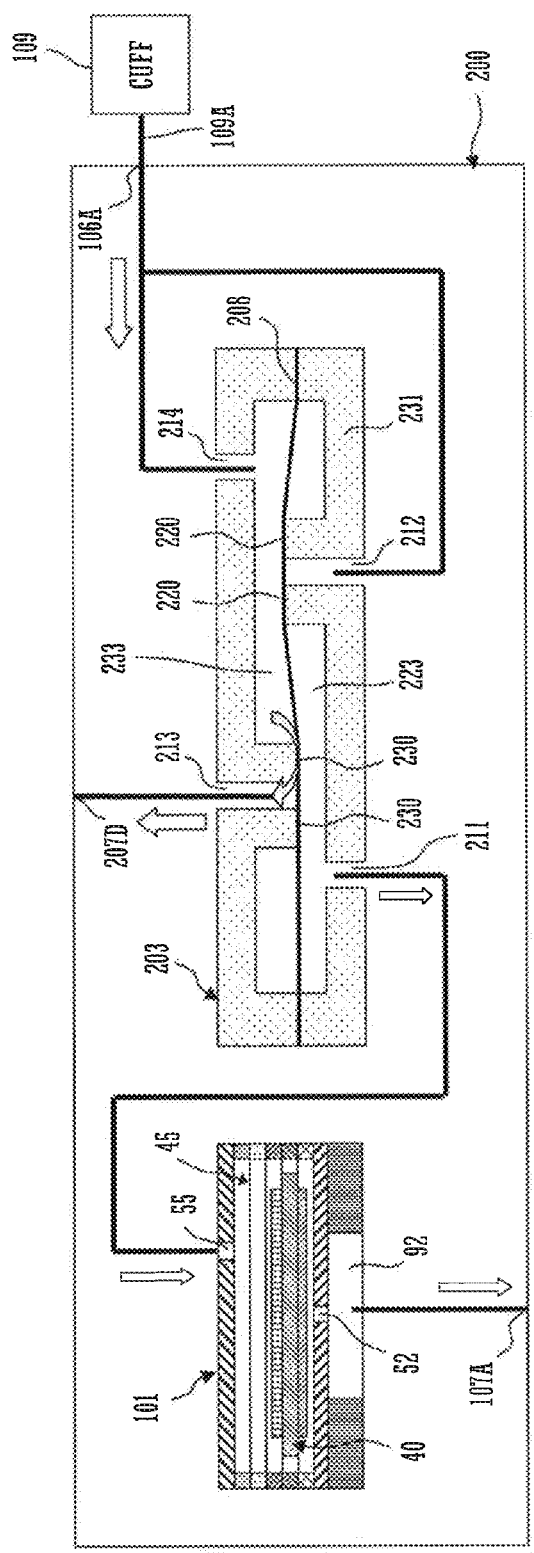
FIG. 15 is an explanatory view showing a flow of air immediately after the piezoelectric pump 101 shown in FIG. 13 stops the pumping operation.

Here, the operation of the fluid control device 200 at the time of blood pressure measurement will be described. FIG. 14 is an explanatory view showing a flow of air when the piezoelectric pump 101 shown in FIG. 13 is performing a pumping operation. FIG. 15 is an explanatory view showing a flow of air immediately after the piezoelectric pump 101 shown in FIG. 13 stops the pumping operation.

The fluid control device 200 makes the piezoelectric pump 101 perform the pumping operation when starting the blood pressure measurement. Accordingly, the piezoelectric pump 101 sucks external air from a suction port 107A and makes the air flow into a pump chamber 45 in the piezoelectric pump 101. Then, the piezoelectric pump 101 makes the air flow from the discharge hole 55 of the piezoelectric pump 101 into the valve 203. In the valve 203, the discharge pressure in the forward direction from the first ventilation hole 211 to the second ventilation hole 212 is generated by the pumping operation of the piezoelectric pump 101, so that the pressure of the lower valve chamber 223 becomes higher than the pressure of the upper valve chamber 233. Accordingly, the diaphragm 208 opens the second ventilation hole 212 and makes the first ventilation hole 211 and the second ventilation hole 212 communicate with each other, and the diaphragm 208 seals the third ventilation hole 213 and blocks the ventilation between the communicating hole 214 and the second ventilation hole 212, and the third ventilation hole 213. As a result, the air is sent out from the piezoelectric pump 101 to the cuff 109 through the first ventilation hole 211 and the second ventilation hole 212 of the valve 203 (see FIG. 14), and the pressure (the air pressure) in the cuff 109 increases.

It should be noted the fluid control device 200 has a structure in which the second ventilation hole 212 and the communicating hole 214 of the valve 203 communicate with each other. In addition, the valve 203 has a shape in which the first ventilation hole 211 is located in the outer periphery, centering on the second ventilation hole 212. Accordingly, the air that flows out of the second ventilation hole 212 through the first ventilation hole 211 of the valve 203 becomes a pressure slightly lower than the discharge pressure of the piezoelectric pump 101 and flows from the communicating hole 214 into the upper valve chamber 233. On the other hand, the discharge pressure of the piezoelectric pump 101 is applied to the lower valve chamber 223. As a result, in the valve 203, the pressure of the lower valve chamber 223 is slightly higher than the pressure of the upper valve chamber 233, and, in the valve 203, the diaphragm 208 seals the third ventilation hole 213 and the second ventilation hole 212 is kept open. Additionally, since a difference in pressure between the lower valve chamber 223 and the upper valve chamber 233 is small, the difference in pressure is not extremely deviated, so that the diaphragm 208 can be prevented from being damaged.

Subsequently, after the blood pressure measurement is completed, the fluid control device 200 stops the pumping operation of the piezoelectric pump 101. Here, the volume of the pump chamber 45 and the lower valve chamber 223 is extremely small as compared with the volume of the air that can be stored in the cuff 109. Therefore, when the pumping operation of the piezoelectric pump 101 stops, the air in the pump chamber 45 and the lower valve chamber 223 is immediately exhausted from the suction port 107A of the fluid control device 200 to the outside of the fluid control device 200 through the central ventilation hole 52 and the opening 92 of the piezoelectric pump 101. In addition, the pressure of the cuff 109 is applied to the upper valve chamber 233. As a result, in the valve 203, after the pumping operation of the piezoelectric pump 101 stops, the pressure of the lower valve chamber 223 is immediately reduced lower than the pressure of the upper valve chamber 233.

In the valve 203, when the pressure of the lower valve chamber 223 is reduced lower than the pressure of the upper valve chamber 233, the diaphragm 208 abuts against the valve seat 220 and seals the second ventilation hole 212, and opens the third ventilation hole 213 and makes the communicating hole 214 and the third ventilation hole 213 communicate with each other. This enables the air in the cuff 109 to be rapidly exhausted from an exhaust port 207D located in the housing of the fluid control device 200 through the communicating hole 214 and the third ventilation hole 213 (see FIG. 15).

Therefore, the valve 203 and the fluid control device 200 according to the present preferred embodiment make it possible to achieve an effect similar to the effect that can be achieved by the first preferred embodiment. Furthermore, since the valve 203 is an integrated valve that preferably includes the check valve 102 and the exhaust valve 103 that are shown in FIG. 2, and the valve 203 and the fluid control device 200 according to the present preferred embodiment can reduce the size.

Subsequently, hereinafter, a fluid control device 300 according to a third preferred embodiment of the present invention will be described. This third preferred embodiment is different from the above described second preferred embodiment in the structure of a valve 303 and is preferably the same or substantially the same as the above described second preferred embodiment in other configurations.

Figure 16:
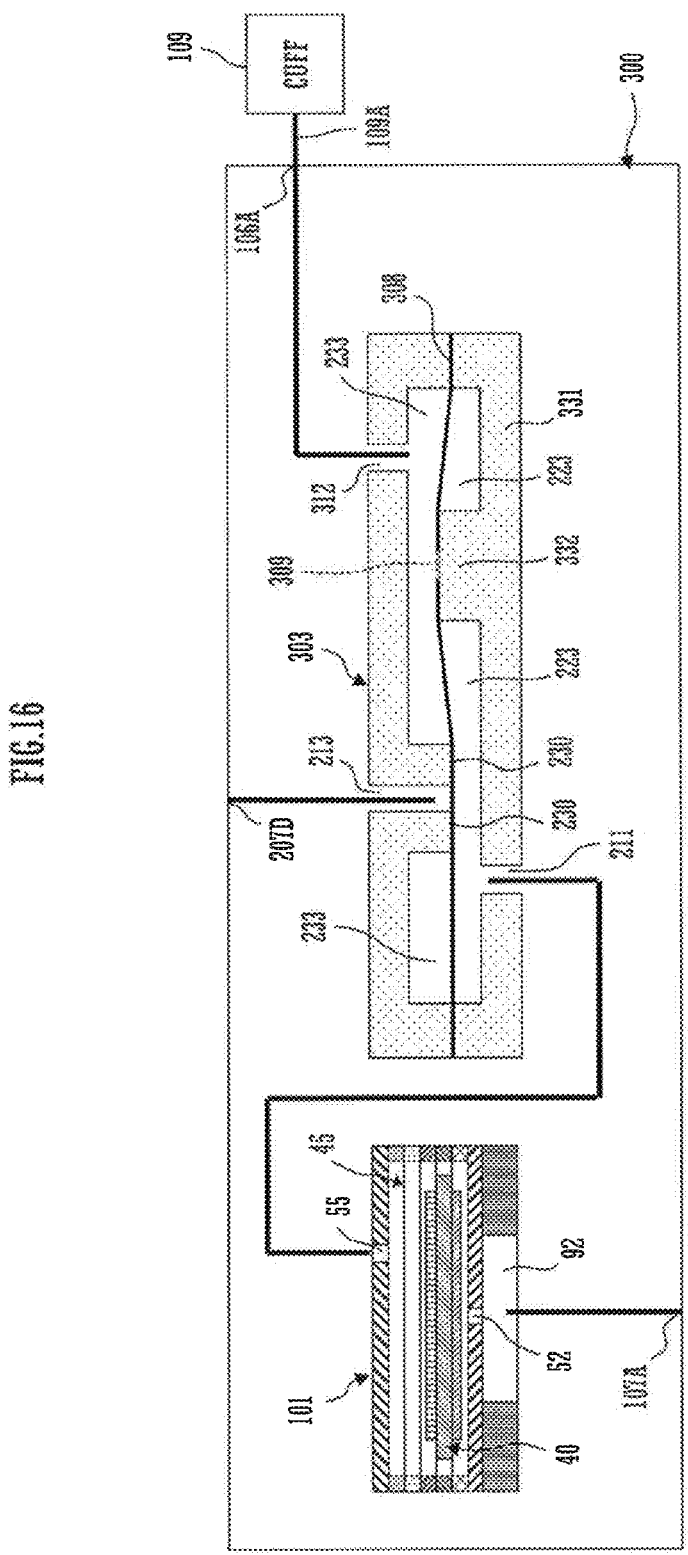
FIG. 16 is an explanatory view showing a connection relationship among a piezoelectric pump 101, a valve 303, and a cuff 109 that are included in a fluid control device 300 according to a third preferred embodiment of the present invention.

To begin with, the structure of the valve 303 will be described. FIG. 16 is an explanatory view showing a connection relationship among a piezoelectric pump 101, the valve 303, and a cuff 109 that are included in the fluid control device 300 according to the third preferred embodiment of the present invention. The valve 303 is a deformed version of the valve 203 shown in FIG. 13, and includes a cylindrical or substantially circular valve housing 331 and a diaphragm 308 including a circular or substantially circular thin film.

The valve housing 331 includes a first ventilation hole 211 that communicates with the discharge hole 55 of the piezoelectric pump 101; a second ventilation hole 312 that communicates with the cuff 109; a third ventilation hole 213 that communicates with the outside of the fluid control device 300; a valve seat 230 that is projected from the peripheral end of the third ventilation hole 213 to the diaphragm 308 side; and a projecting portion 332 that is projected to the diaphragm 308 side.

The diaphragm 308 includes a hole portion 309 in a portion of a region that is opposed to the projecting portion 332. The diaphragm 308 is fixed to the valve housing 331 so as to contact the valve seat 230 and make the peripheral end of the hole portion 309 contact the projecting portion 332. Accordingly, the diaphragm 308 divides the inside of the valve housing 331 and defines a ring shaped lower valve chamber 223 that communicates with the first ventilation hole 211, and a ring shaped upper valve chamber 233 that communicates with the second ventilation hole 312. The projecting portion 332 is arranged in the valve housing 331 so as to pressurize the peripheral end of the hole portion 309 in the diaphragm 308.

In the above structure, the valve 303 opens and closes the valve when the diaphragm 308 contacts or separates from the projecting portion 332 by a difference in pressure between the lower valve chamber 223 and the upper valve chamber 233. In addition, the valve 303 opens and closes the valve when the diaphragm 308 contacts or separates from the valve seat 230 by the difference in pressure between the upper valve chamber 233 and the lower valve chamber 223.

It should be noted, in the present preferred embodiment, the lower valve chamber 223 is equivalent to the "first region" according to a preferred embodiment of the present invention, and the upper valve chamber 233 is equivalent to the "second region" according to a preferred embodiment of the present invention.

Figure 17:
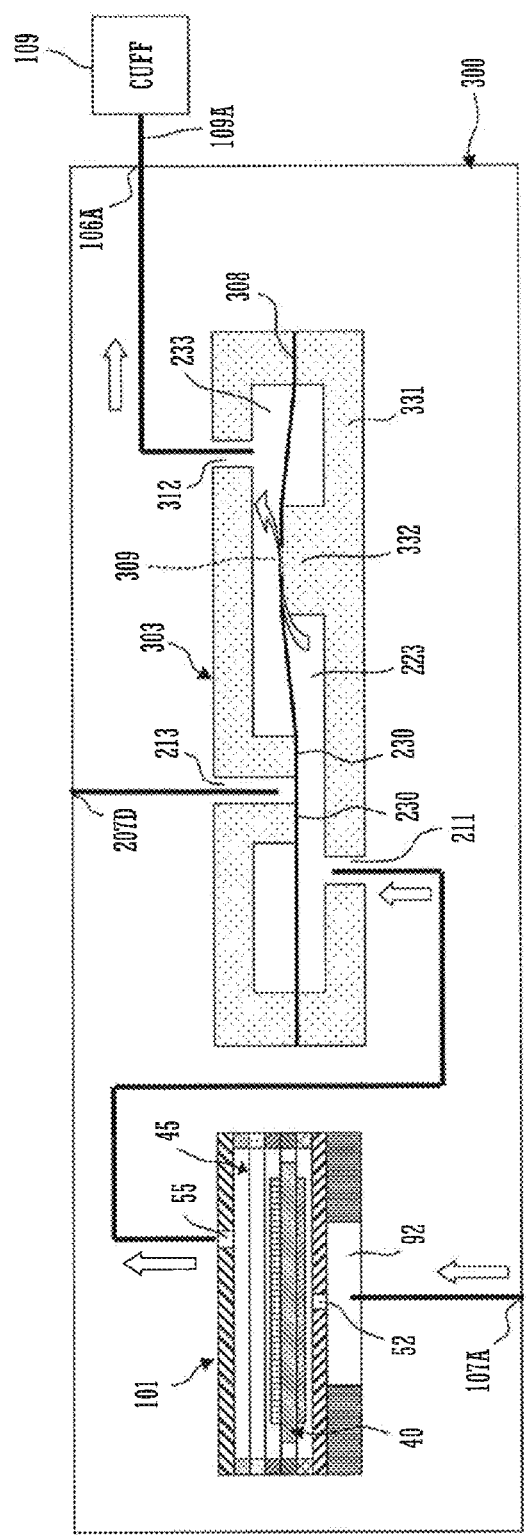
FIG. 17 is an explanatory view showing a flow of air when the piezoelectric pump 101 shown in FIG. 16 is performing a pumping operation.
Figure 18:
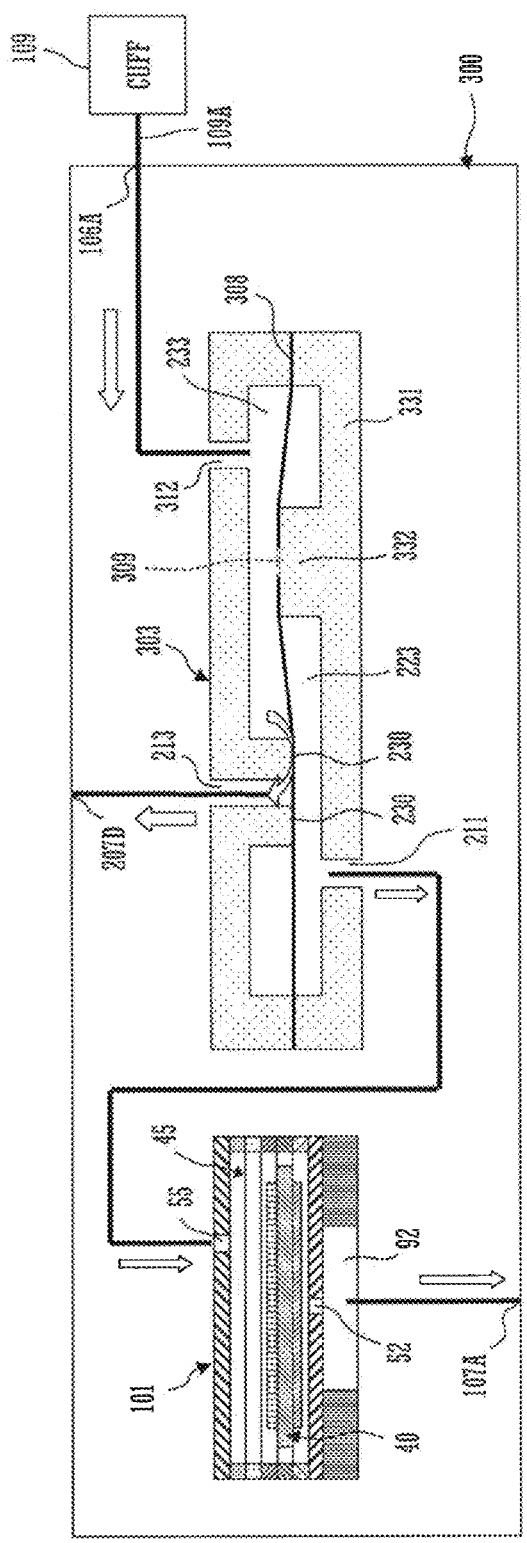
FIG. 18 is an explanatory view showing a flow of air immediately after the piezoelectric pump 101 shown in FIG. 16 stops the pumping operation.

Here, the operation of the fluid control device 300 at the time of blood pressure measurement will be described. FIG. 17 is an explanatory view showing a flow of air when the piezoelectric pump 101 shown in FIG. 16 is performing a pumping operation. FIG. 18 is an explanatory view showing a flow of air immediately after the piezoelectric pump 101 shown in FIG. 16 stops the pumping operation.

The fluid control device 300 makes the piezoelectric pump 101 perform the pumping operation when starting blood pressure measurement. Accordingly, the piezoelectric pump 101 sucks external air from a suction port 107A and makes the air flow into a pump chamber 45 in the piezoelectric pump 101. Then, the piezoelectric pump 101 makes the air flow from the discharge hole 55 of the piezoelectric pump 101 into the valve 303. In the valve 303, the discharge pressure in the forward direction from the first ventilation hole 211 to the second ventilation hole 312 is generated by the pumping operation of the piezoelectric pump 101, so that the pressure of the lower valve chamber 223 becomes higher than the pressure of the upper valve chamber 233. Accordingly, the diaphragm 308 separates from the projecting portion 332 and makes the first ventilation hole 211 and the second ventilation hole 312 communicate through the hole portion 309, and the diaphragm 308 seals the third ventilation hole 213 and blocks the ventilation between the second ventilation hole 312 and the third ventilation hole 213. As a result, the air is sent out from the piezoelectric pump 101 to the cuff 109 through the first ventilation hole 221, the hole portion 309, and the second ventilation hole 312 of the valve 303 (see FIG. 17), and the pressure (the air pressure) in the cuff 109 increases.

It should be noted the diaphragm 308 is fixed to the valve housing 331 so that the peripheral end of the hole portion 309 contacts the projecting portion 332. Then, this projecting portion 332 pressurizes the peripheral end of the hole portion 309 in the diaphragm 308. Accordingly, the air that flows out of the hole portion 309 through the first ventilation hole 211 of the valve 303 becomes a pressure slightly lower than the discharge pressure of the piezoelectric pump 101 and flows from the hole portion 309 into the upper valve chamber 233. On the other hand, the discharge pressure of the piezoelectric pump 101 is applied to the lower valve chamber 223. As a result, in the valve 303, the pressure of the lower valve chamber 223 is slightly higher than the pressure of the upper valve chamber 233, and, in the valve 303, the diaphragm 308 seals the third ventilation hole 213 and the hole portion 309 is kept open. Additionally, since the difference in pressure between the lower valve chamber 223 and the upper valve chamber 233 is small, the difference in pressure is not extremely deviated, so that the diaphragm 308 can be prevented from being damaged.

Subsequently, after the blood pressure measurement is completed, the fluid control device 300 stops the pumping operation of the piezoelectric pump 101. Here, as stated above, when the pumping operation of the piezoelectric pump 101 stops, the air in the pump chamber 45 and the lower valve chamber 223 is immediately exhausted from the suction port 107A of the fluid control device 300 to the outside of the fluid control device 300 through the central ventilation hole 52 and the opening 92 of the piezoelectric pump 101. In addition, the pressure of the cuff 109 is applied to the upper valve chamber 233 from the second ventilation hole 312. As a result, in the valve 303, after the pumping operation of the piezoelectric pump 101 stops, the pressure of the lower valve chamber 223 is immediately reduced lower than the pressure of the upper valve chamber 233.

In the valve 303, when the pressure of the lower valve chamber 223 is reduced lower than the pressure of the upper valve chamber 233, the diaphragm 308 abuts against the projecting portion 332 and seals the hole portion 309, and opens the third ventilation hole 213 and makes the second ventilation hole 312 and the third ventilation hole 213 communicate with each other. This enables the air in the cuff 109 to be rapidly exhausted from the exhaust port 207D through the second ventilation hole 312 and the third ventilation hole 213 (see FIG. 18). Therefore, the valve 303 and the fluid control device 300 according to the present preferred embodiment make it possible to achieve an effect similar to the effect that can be achieved by the second preferred embodiment.

Figure 19:
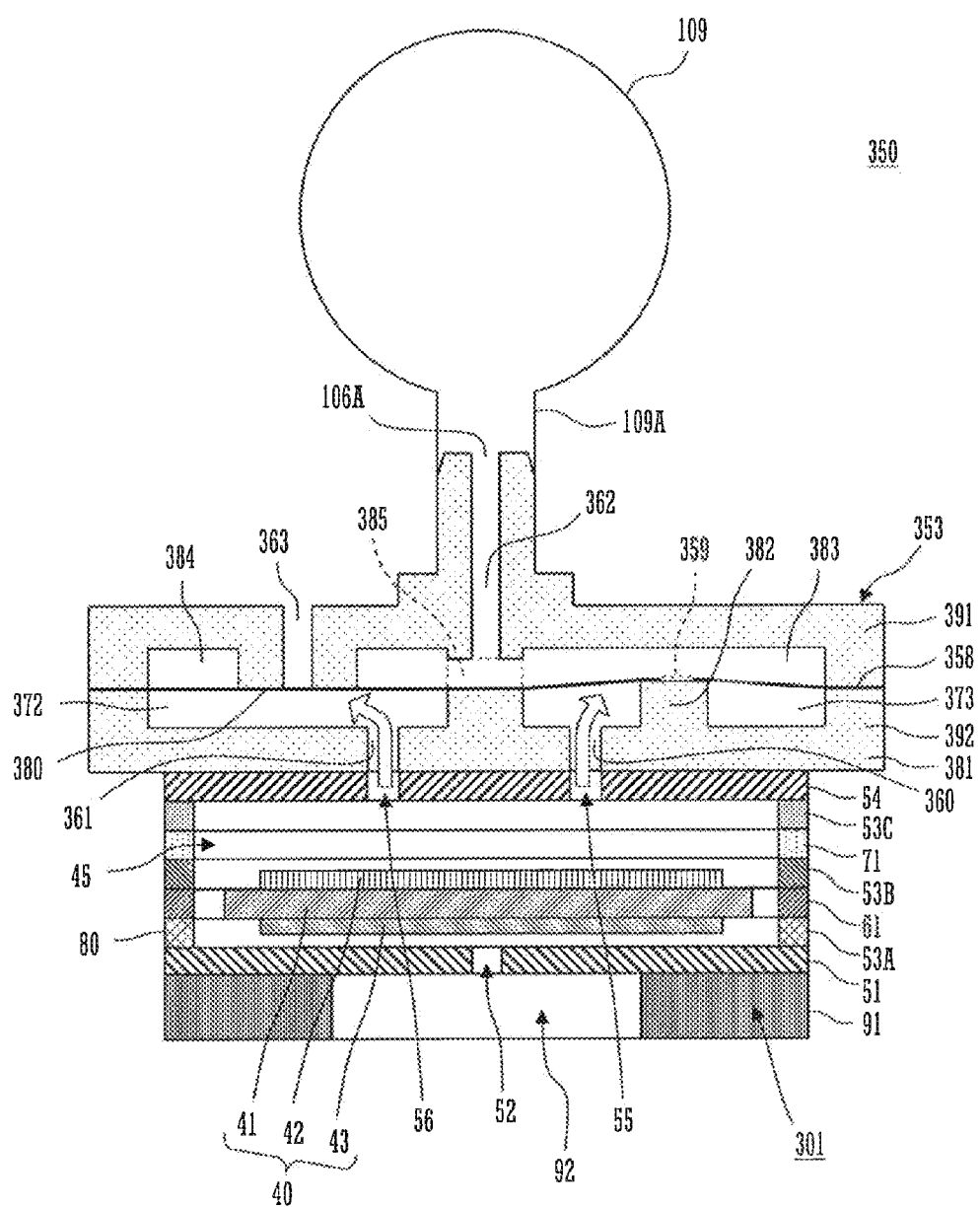
FIG. 19 is a cross sectional view of a main portion of a fluid control device 350 according to a modification example according to the third preferred embodiment of the present invention.
Figure 20:
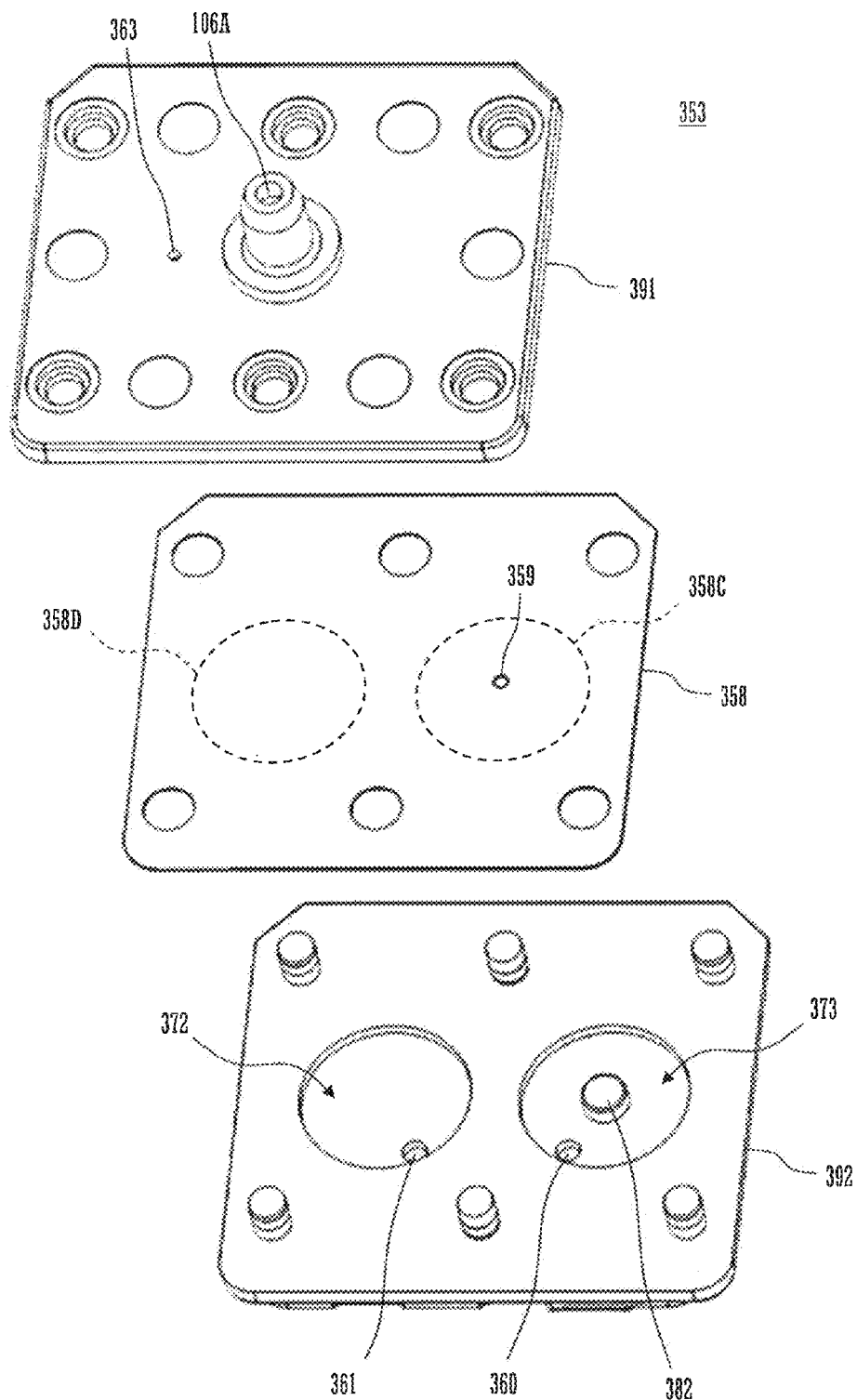
FIG. 20 is an exploded perspective view of a valve 353 shown in FIG. 19.
Figure 21:
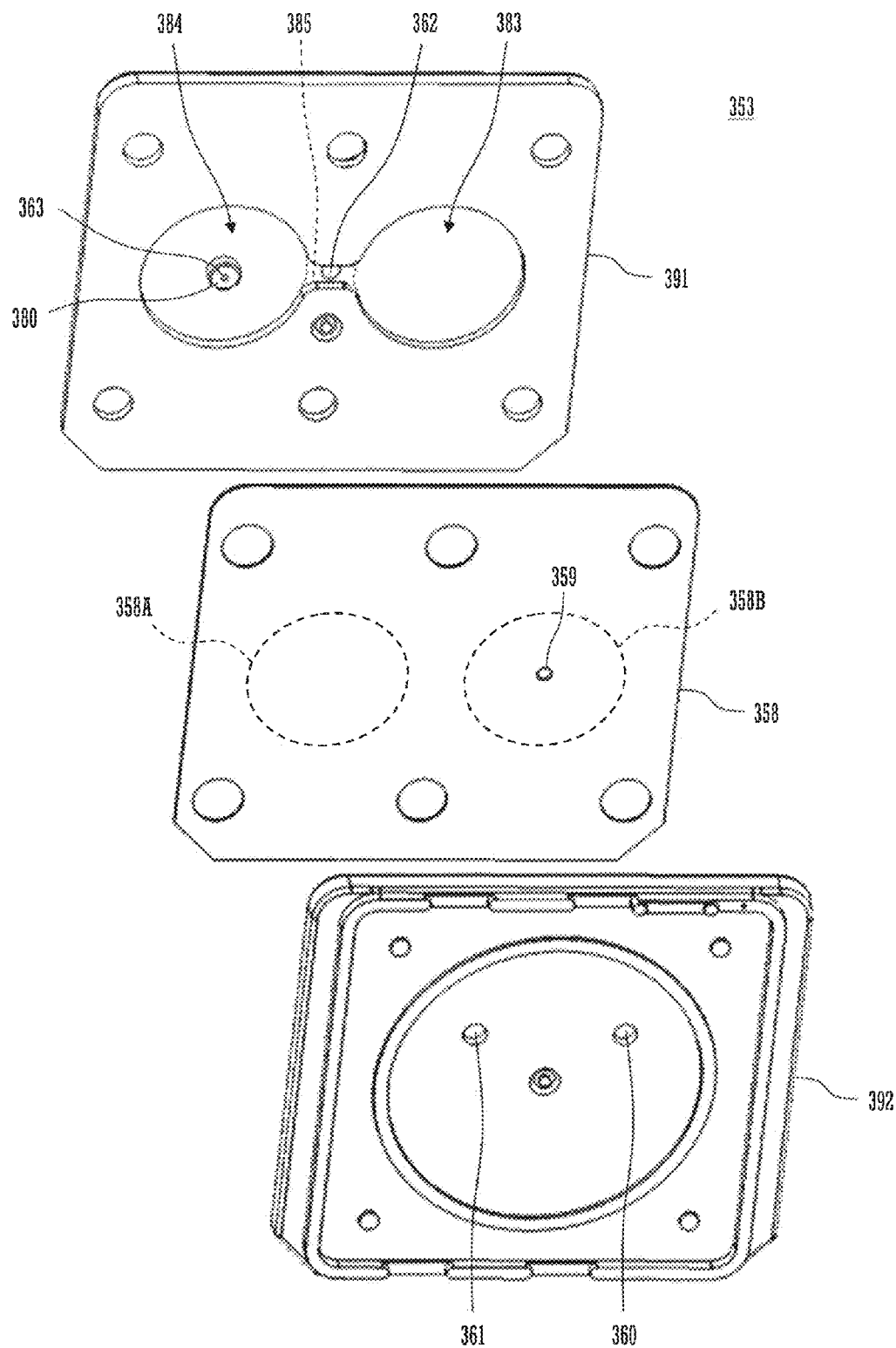
FIG. 21 is an exploded perspective view of the valve 353 shown in FIG. 19.

Hereinafter, a fluid control device 350 according to a modification example of the third preferred embodiment of the present invention will be described. FIG. 19 is a cross sectional view of a main portion of the fluid control device 350 according to the modification example of the third preferred embodiment of the present invention. FIG. 20 and FIG. 21 are exploded perspective views of a valve 353 shown in FIG. 19. FIG. 20 is the exploded perspective view of the valve 353 as viewed from the upper surface side that is connected to the cuff 109, and FIG. 21 is the exploded perspective view of the valve 353 as viewed from the bottom side that is bonded to a piezoelectric pump 301.

The fluid control device 350 preferably includes the piezoelectric pump 301 and the valve 353. This piezoelectric pump 301 is different from the above described piezoelectric pump 101 in that two discharge holes 55 and 56 are provided, and preferably is the same or substantially the same as the above described piezoelectric pump 101 in other configurations.

The valve 353 is a deformed version of the valve 303 shown in FIG. 16 and an integrated valve that preferably includes the check valve 102 and the exhaust valve 103 that are shown in FIG. 2. The valve 353, as shown in FIG. 19, FIG. 20, and FIG. 21, has a structure in which a lower valve housing 392, a diaphragm 358 that is made of a rectangular or substantially rectangular thin film, and an upper valve housing 391 are laminated in this order. Here, the upper valve housing 391 and the lower valve housing 392 are equivalent to the valve housing 381.

To the bottom surface of the lower valve housing 392, as shown in FIG. 19, the top surface of the piezoelectric pump 301 is bonded. The lower valve housing 392, as shown in FIG. 19, FIG. 20, and FIG. 21, includes a first ventilation hole 361 that communicates with the discharge hole 56 of the piezoelectric pump 301; a fourth ventilation hole 360 that communicates with the discharge hole 55 of the piezoelectric pump 301; and a projecting portion 382 that is projected to the diaphragm 358 side.

The upper valve housing 391, as shown in FIG. 19, FIG. 20, and FIG. 21, includes a second ventilation hole 362 that communicates with the cuff 109; a third ventilation hole 363 that communicates with the outside of the fluid control device 350, and a valve seat 380 that is projected from the peripheral end of the third ventilation hole 363 to the diaphragm 358 side.

The diaphragm 358, as shown in FIG. 19, FIG. 20, and FIG. 21, includes a hole portion 359 in a portion of a region as opposed to the projecting portion 382. The diaphragm 358 is held by the upper valve housing 391 and the lower valve housing 392 from the both sides and is fixed to the upper valve housing 391 and the lower valve housing 392 so as to contact the valve seat 380 and make the peripheral end of the hole portion 359 contact the projecting portion 382. Accordingly, the diaphragm 358 divides the inside of the valve housing 381 and defines a cylindrical or substantially cylindrical first lower valve chamber 372 that communicates with a first ventilation hole 361; a ring shaped second lower valve chamber 373 that communicates with a fourth ventilation hole 360; a cylindrical or substantially cylindrical first upper valve chamber 383 that communicates with a second ventilation hole 362 through a communicating path 385; and a ring shaped second upper valve chamber 384 that communicates with the first upper valve chamber 383 through the communicating path 385. Therefore, during the pumping operation of the piezoelectric pump 301, the air discharged out of the discharge holes 55 and 56 of the piezoelectric pump 301, as shown in FIG. 19, flows into both the first lower valve chamber 372 and the second lower valve chamber 373.

The projecting portion 382 is arranged in the lower valve housing 392 so as to pressurize the peripheral end of the hole portion 359 in the diaphragm 358.

In the above structure, the valve 353 opens and closes the valve when the diaphragm 358 contacts or separates from the projecting portion 382 by a difference in pressure between the first lower valve chamber 372 and the second lower valve chamber 373, and the first upper valve chamber 383 and the second lower valve chamber 384. In addition, the valve 353 opens and closes the valve when the diaphragm 358 contacts or separates from the valve seat 380 by the difference in pressure between the first lower valve chamber 372 and the second lower valve chamber 373, and the first upper valve chamber 383 and the second lower valve chamber 384.

Therefore, the valve 353 and the fluid control device 350 according to the present modification example make it possible to achieve an effect similar to the effect that can be achieved by the second preferred embodiment. Moreover, in the valve 353 according to the present modification example, since each of the regions 358A, 358B, 358C, and 358D of the diaphragm 358 facing each of the valve chambers 372, 373, 383, and 384 has a circular or substantially circular shape, as shown in FIGS. 20 and 21, the tension of the diaphragm 358 is applied uniformly. Thus, according to the valve 353 of the present modification example, each valve can be more reliably opened and closed.

Subsequently, hereinafter, a fluid control device 400 according to a fourth preferred embodiment of the present invention will be described. This fourth preferred embodiment is different from the above described third preferred embodiment in that a piezoelectric pump 401 and a valve 403 are directly connected to each other, and preferably is the same or substantially the same as the above described third preferred embodiment in other configurations.

Figure 22:
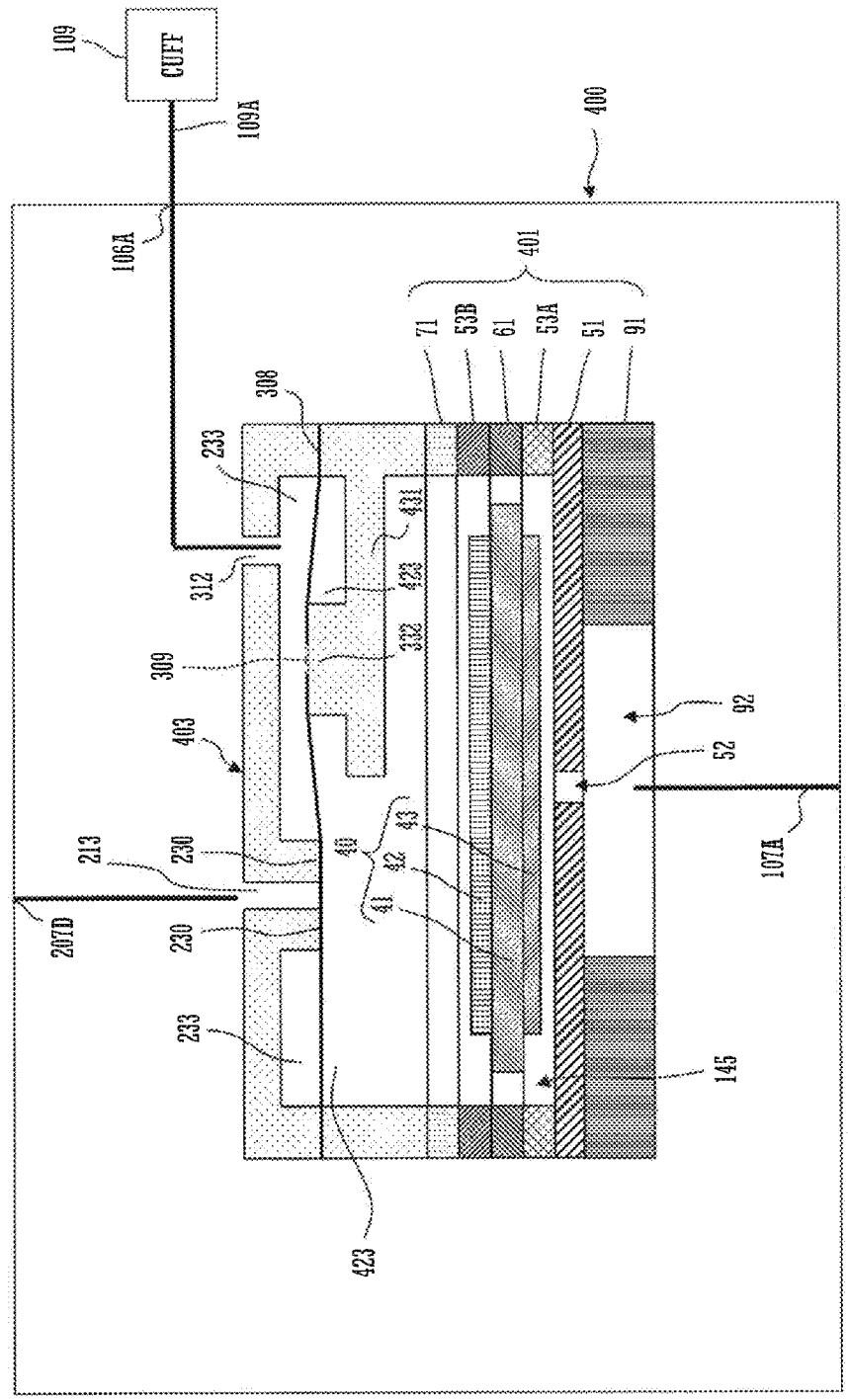
FIG. 22 is an explanatory view showing a connection relationship among a piezoelectric pump 401, a valve 403, and a cuff 109 that are included in a fluid control device 400 according to a fourth preferred embodiment of the present invention.
Figure 23:
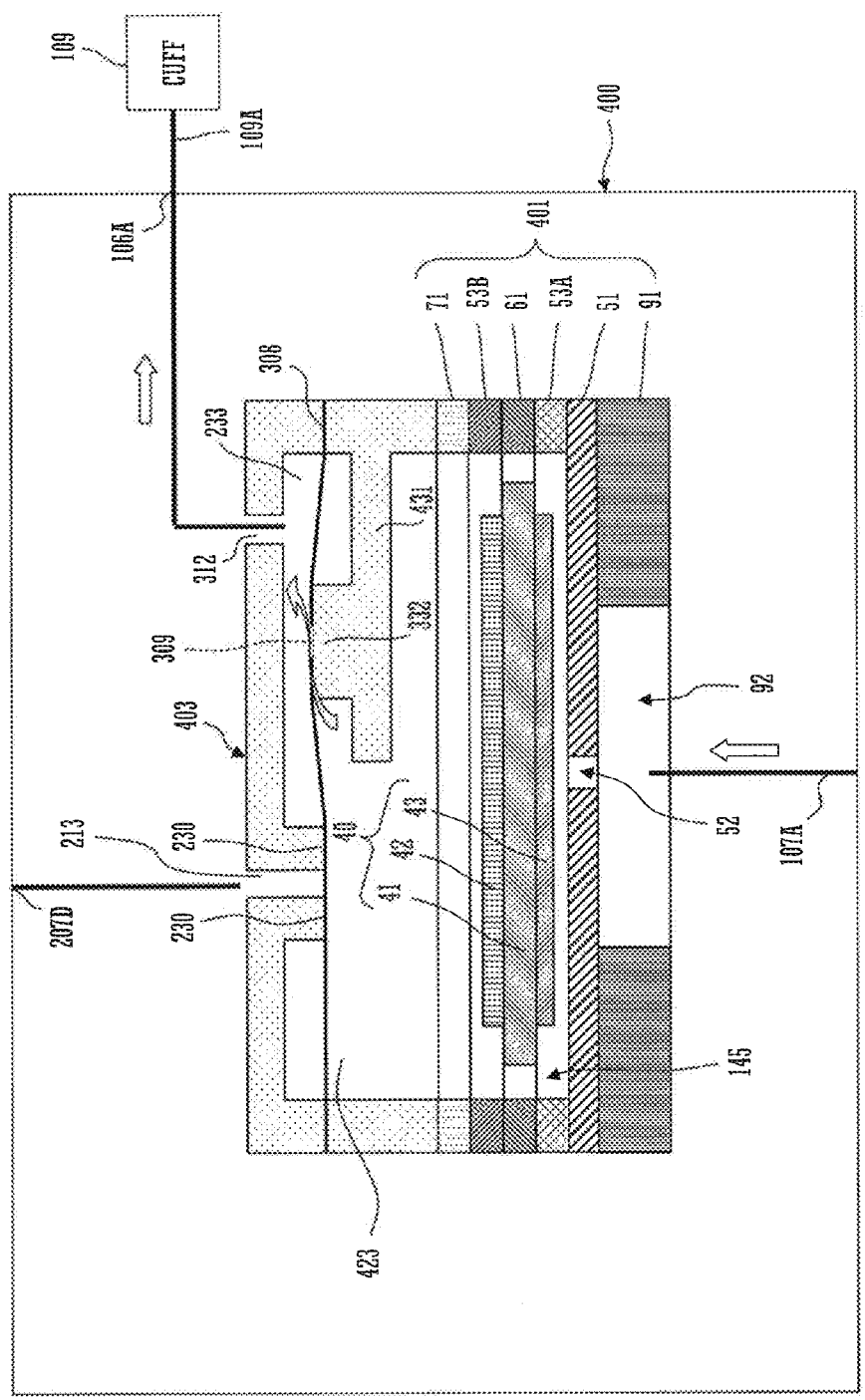
FIG. 23 is an explanatory view showing a flow of air when the piezoelectric pump 401 shown in FIG. 22 is performing a pumping operation.
Figure 24:
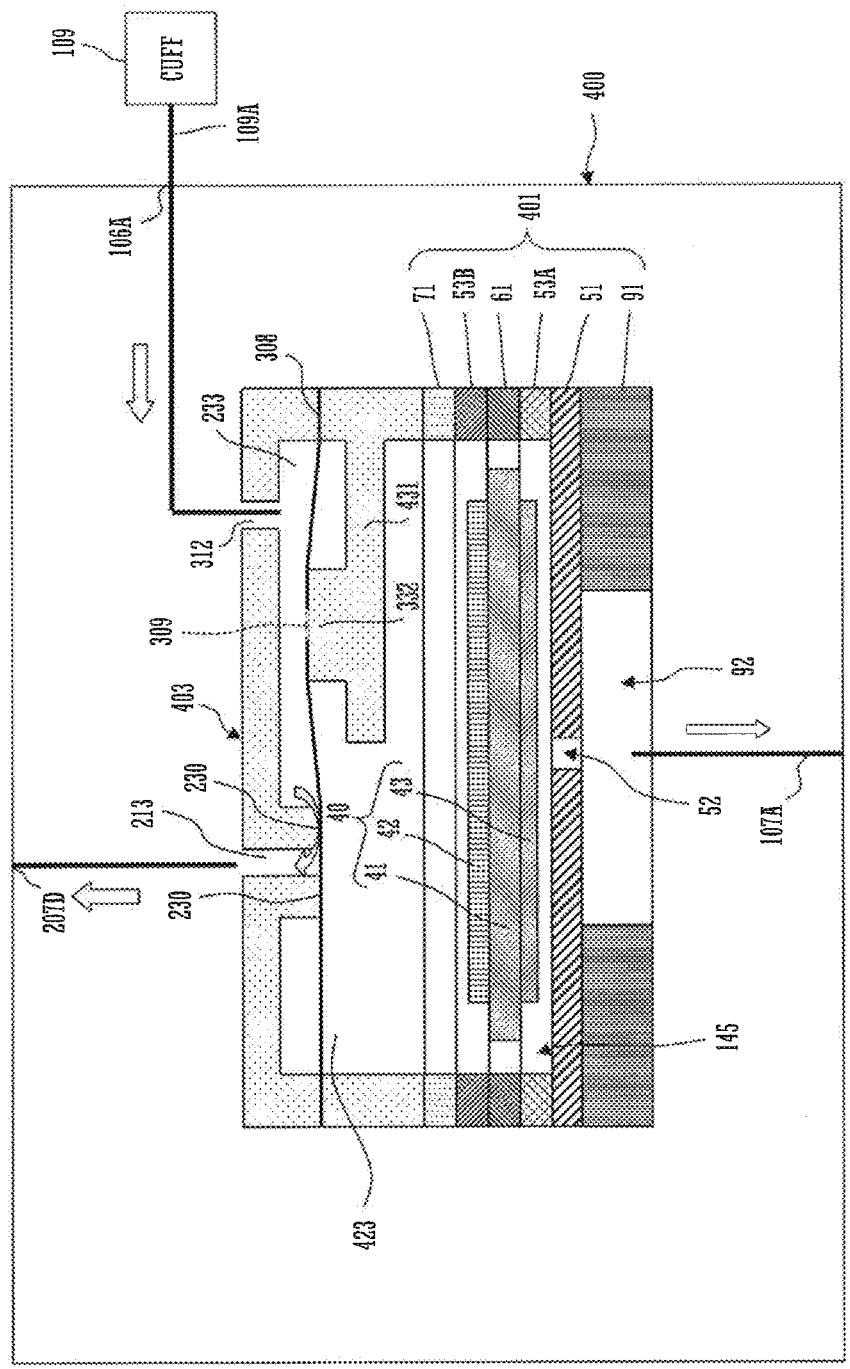
FIG. 24 is an explanatory view showing a flow of air immediately after the piezoelectric pump 401 shown in FIG. 22 stops the pumping operation.

FIG. 22 is an explanatory view showing a connection relationship among the piezoelectric pump 401, the valve 403, and a cuff 109 that are included in a fluid control device 400 according to the fourth preferred embodiment of the present invention. FIG. 23 is an explanatory view showing a flow of air when the piezoelectric pump 401 shown in FIG. 22 is performing a pumping operation. FIG. 24 is an explanatory view showing a flow of air immediately after the piezoelectric pump 401 shown in FIG. 22 stops the pumping operation.

A complex of the piezoelectric pump 401 and the valve 403 is an integral structure that preferably includes the piezoelectric pump 101 and the valve 303 that are shown in FIG. 16. More specifically, the complex of the piezoelectric pump 401 and the valve 403 has a structure in which the spacer 53C of the piezoelectric pump 101 shown in FIG. 4 is removed, and the lid portion 54 is replaced with a valve housing 431 having a shape in which the first ventilation hole 211 of the valve housing 331 as shown in FIG. 16 is expanded; and preferably is the same or substantially the same in other configurations as the piezoelectric pump 101 as shown in FIG. 4.

The diaphragm 308 divides the inside of the valve housing 403 and defines a lower valve chamber 423 that communicates with a suction hole 52, and a ring shaped upper valve chamber 233 that communicates with the second ventilation hole 312.

Additionally, the pump chamber 145 and the lower valve chamber 423 of the piezoelectric pump 401 communicate with each other.

In the above structure, the valve 403, as shown in FIG. 23 and FIG. 24, opens and closes the valve when the diaphragm 308 contacts or separates from the projecting portion 332 by a difference in pressure between the lower valve chamber 423 and the upper valve chamber 233. In addition, the valve 403 opens and closes the valve when the diaphragm 308 contacts or separates from the valve seat 230 by the difference in pressure between the upper valve chamber 233 and the lower valve chamber 423.

Therefore, the fluid control device 400 according to the present preferred embodiment makes it possible to achieve an effect similar to the effect that can be achieved by the third preferred embodiment. Additionally, in the valve 403 according to the present preferred embodiment, direct connection of the valve 403 and the piezoelectric pump 401 used as a pressure generating device increases the pressure of the lower valve chamber 423. Therefore, the fluid control device 400 of the present preferred embodiment can further miniaturize the main body of the apparatus.

It should be noted, in the present preferred embodiment, the lower valve chamber 423 is equivalent to the "first region" according to a preferred embodiment of the present invention, and the upper valve chamber 233 is equivalent to the "second region" according to a preferred embodiment of the present invention. Furthermore, in the present preferred embodiment, since the pump chamber 145 and the lower valve chamber 423 of the piezoelectric pump 401 preferably are directly connected to each other and integrated into one body, the vicinity of the position in which the pump chamber 145 and the lower valve chamber 423 are connected is defined as "the first ventilation hole" according to a preferred embodiment of the present invention.

Subsequently, hereinafter, a fluid control device 500 according to a fifth preferred embodiment of the present invention will be described. This fifth preferred embodiment is different from the above described second preferred embodiment in the structure of a valve 503, and preferably is the same or substantially the same as the above described second preferred embodiment in other configurations.

Figure 25:
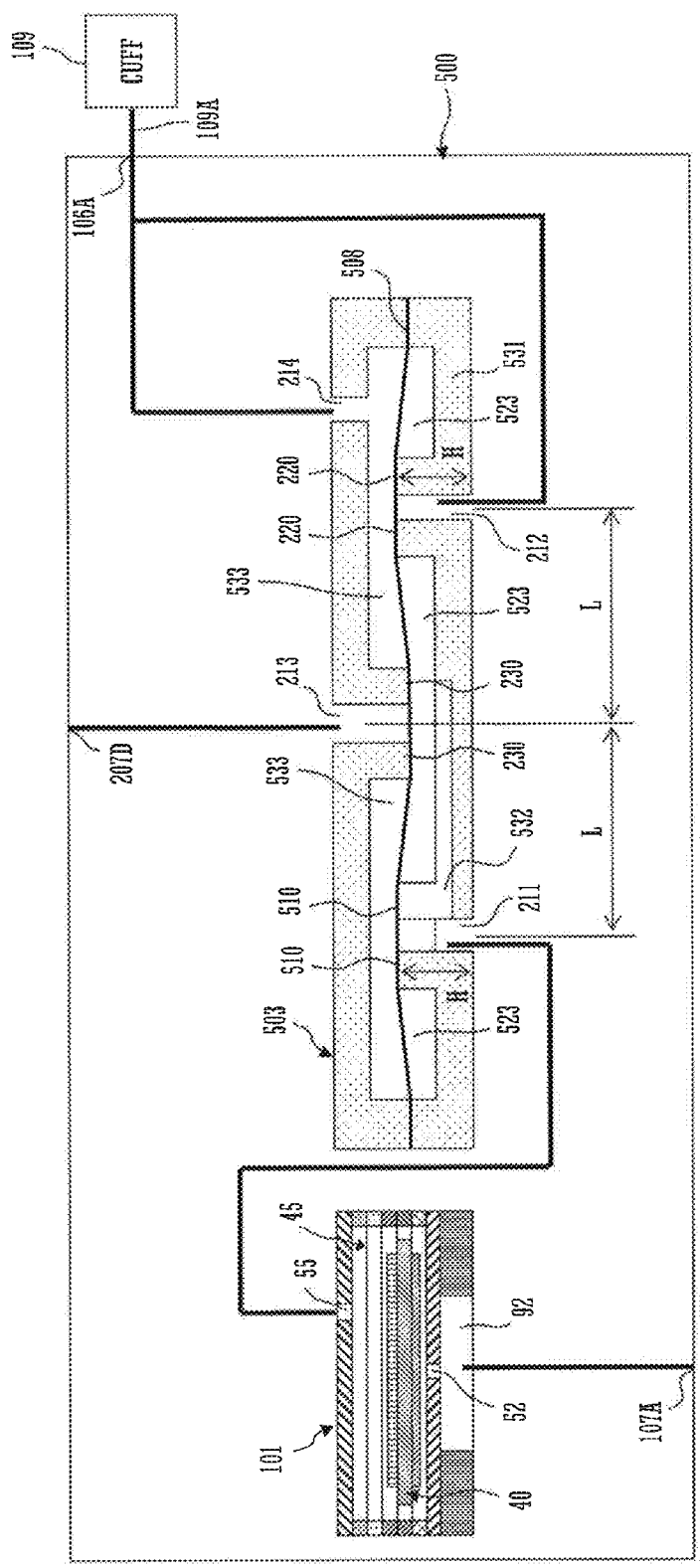
FIG. 25 is an explanatory view showing a connection relationship among a piezoelectric pump 101, a valve 503, and a cuff 109 that are included in a fluid control device 500 according to a fifth preferred embodiment of the present invention.
Figure 26:
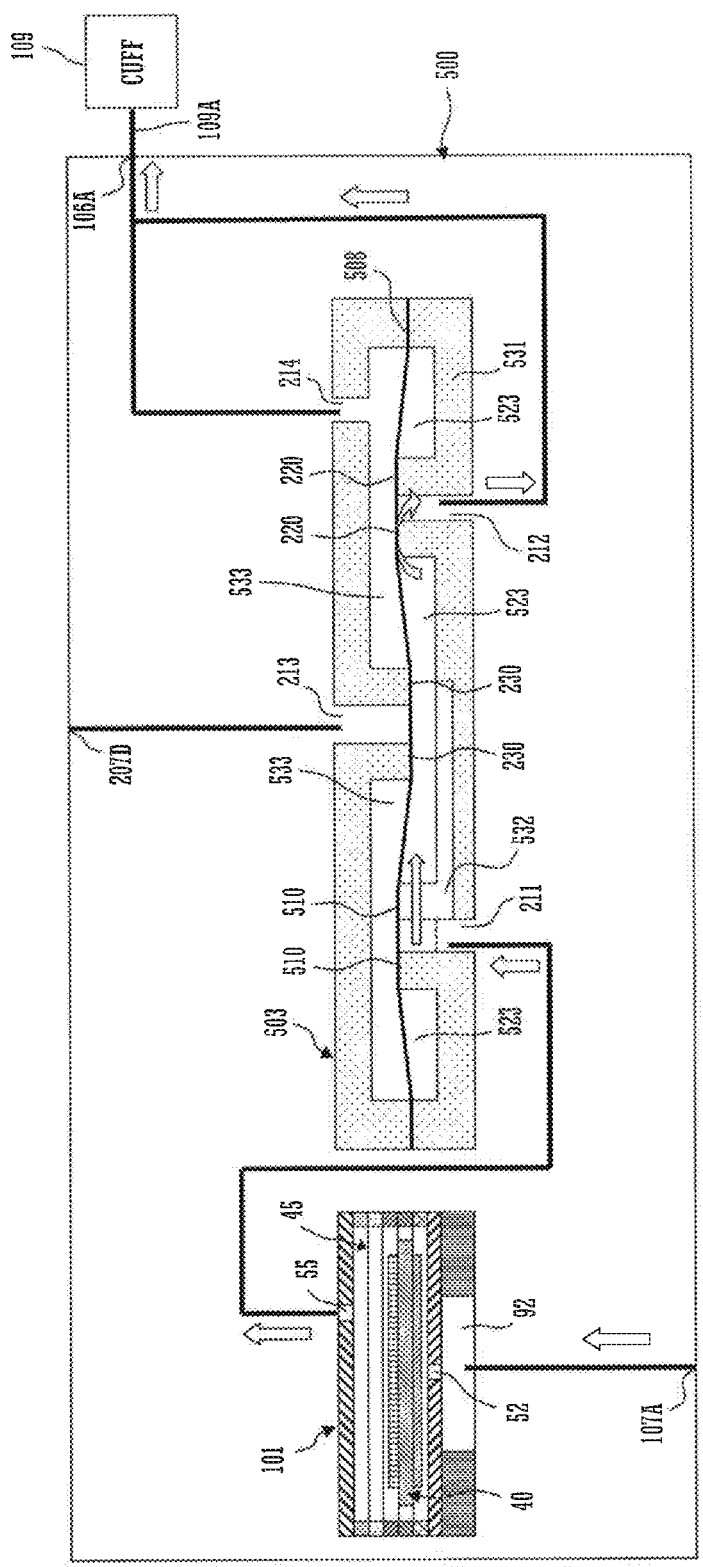
FIG. 26 is an explanatory view showing a flow of air when the piezoelectric pump 101 shown in FIG. 25 is performing a pumping operation.
Figure 27:
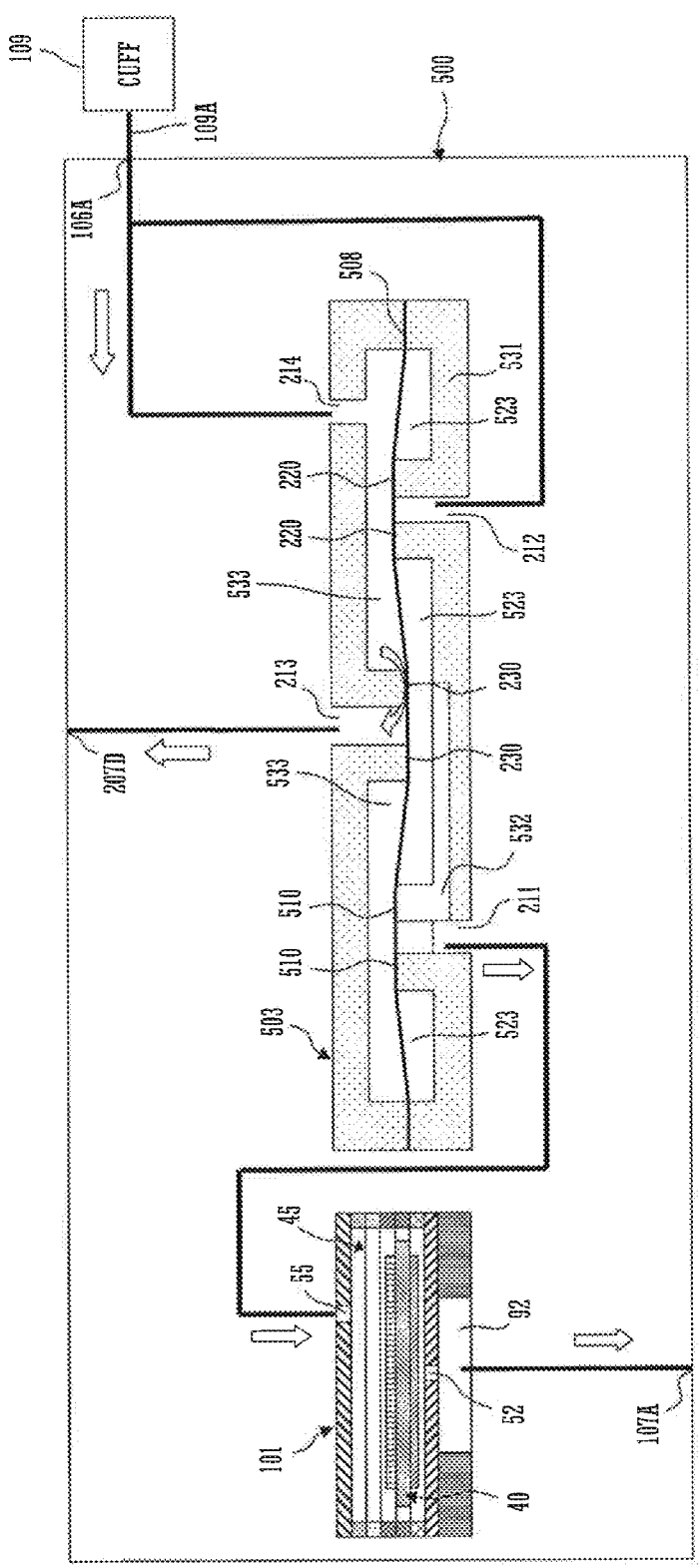
FIG. 27 is an explanatory view showing a flow of air immediately after the piezoelectric pump 101 shown in FIG. 25 stops the pumping operation.

FIG. 25 is an explanatory view showing a connection relationship among a piezoelectric pump 101, the valve 503, and a cuff 109 that are included in a fluid control device 500 according to the fifth preferred embodiment of the present invention. FIG. 26 is an explanatory view showing a flow of air when the piezoelectric pump 101 shown in FIG. 25 is performing a pumping operation. FIG. 27 is an explanatory view showing a flow of air immediately after the piezoelectric pump 101 shown in FIG. 25 stops the pumping operation. This valve 503 is a deformed version of the valve 203 shown in FIG. 13, and includes a cylindrical or substantially cylindrical valve housing 531 and a diaphragm 508 that includes a circular or substantially circular thin film.

The valve housing 531, in the same manner as the valve housing 231 of the valve 203 as shown in FIG. 13, includes a first ventilation hole 211, a second ventilation hole 212, a third ventilation hole 213, a communicating hole 214, and valve seats 220 and 230.

Furthermore, the valve housing 531 includes a valve seat 510 that is projected from the peripheral end of the first ventilation hole 211 to the diaphragm 508 side. This valve seat 510 and the valve seat 220 preferably have the same shape and the same height H. In this regard, since the valve housing 531 including this valve seat 510 includes a cutout 532, the first ventilation hole 211 always communicates with the lower valve chamber 523.

The positional relationship among the first ventilation hole 211, the second ventilation hole 212, and the third ventilation hole 213 in the valve housing 531 will be described in detail. The third ventilation hole 213 is located in the center or approximate center of the valve housing 531. In addition, the first ventilation hole 211 and the second ventilation hole 212 are located in a position of the valve housing 531, the position being a location at which a length L from the center of the first ventilation hole 211 to the center of the third ventilation hole 213 becomes the same as a length L from the center of the third ventilation hole 213 to the center of the second ventilation hole 212.

The diaphragm 508 is fixed to the valve housing 531 so as to contact the valve seats 220, 230, and 510. Accordingly, the diaphragm 508 divides the inside of the valve housing 531 and defines a lower valve chamber 523 and a ring shaped upper valve chamber 533 that communicates with a communicating hole 214. It should be noted, in the present preferred embodiment, the lower valve chamber 523 is equivalent to the "first region" according to a preferred embodiment of the present invention, and the upper valve chamber 533 is equivalent to the "second region" according to a preferred embodiment of the present invention.

In the above structure, the valve 503, as shown in FIG. 26 and FIG. 27, opens and closes the valve when the diaphragm 508 contacts or separates from the valve seat 220 by a difference in pressure between the lower valve chamber 523 and the upper valve chamber 533. In this regard, since the valve housing 531 includes a cutout 532, the first ventilation hole 211 always communicates with the lower valve chamber 523. In addition, the valve 503 opens and closes the valve when the diaphragm 508 contacts or separates from the valve seat 230 by the difference in pressure between the upper valve chamber 533 and the lower valve chamber 523.

Therefore, the valve 503 and the fluid control device 500 according to the present preferred embodiment make it possible to achieve an effect similar to the effect that can be achieved by the second preferred embodiment. Furthermore, according to the valve 503 and the fluid control device 500 of the present preferred embodiment, the diaphragm 508 is in close contact with the valve seat 230 of the third ventilation hole 213 in parallel, so that the air from the upper valve chamber 533 to the third ventilation hole 213 can be prevented from leaking and rapid exhaustion of the air can be further stabilized.

Figure 28:
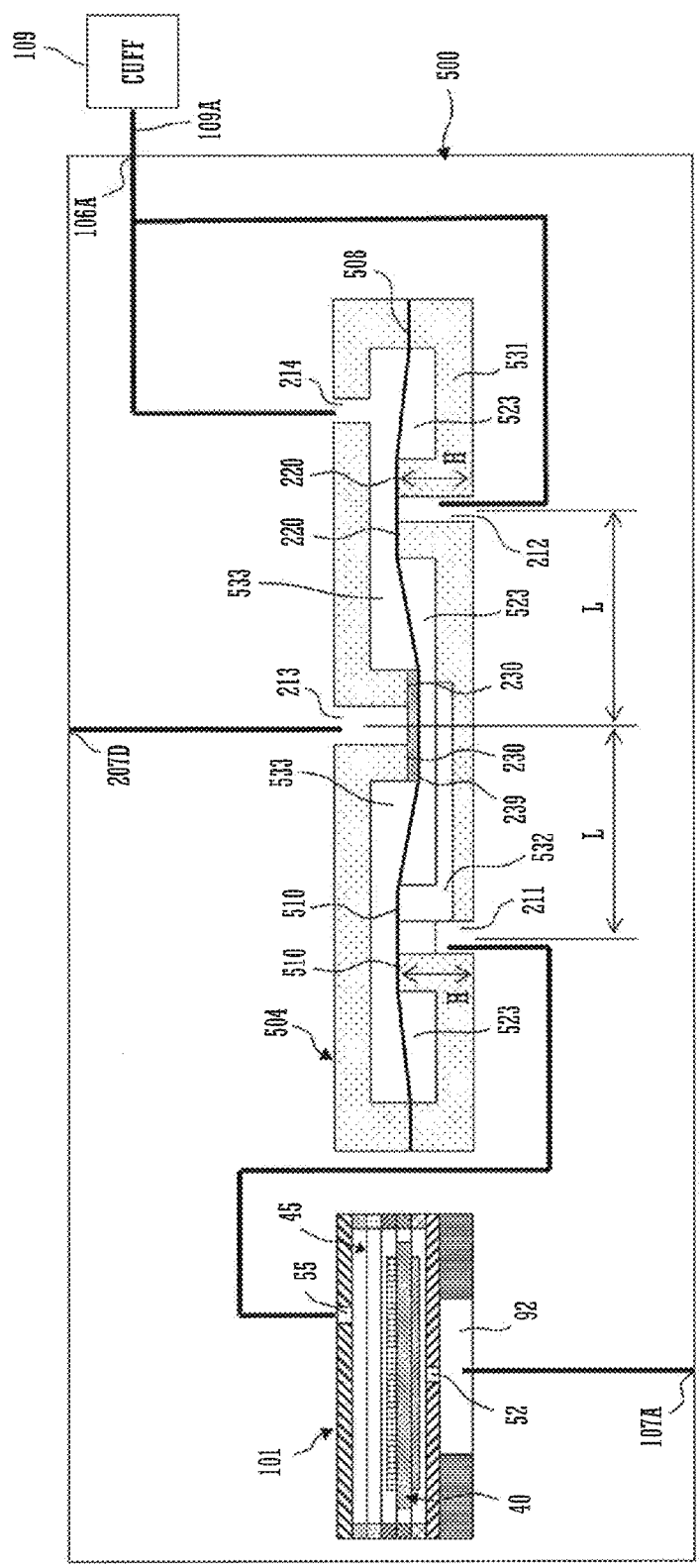
FIG. 28 is an explanatory view showing a connection relationship among a valve 504 as a modification example of the valve 503 shown in FIG. 25, the piezoelectric pump 101, and the cuff 109.

It is to be noted, as shown in FIG. 28, a disc shaped packing 239 may be provided in a position as opposed to the valve seat 230 of the diaphragm 508. The packing 239 is preferably made of an elastic body harder than the diaphragm 508. In the valve 504 equipped with this packing 239, since the packing 239 attached to the diaphragm 508 is in close contact with the valve seat 230 and closes the third ventilation hole 213, the diaphragm 508 can be prevented from being deformed when the diaphragm 508 closes the third ventilation hole 213. Also, in the valve 504, since the valve seat 230 and the packing 239 are in close contact with each other when the diaphragm 508 closes the third ventilation hole 213, air can be further prevented from leaking. Furthermore, in the valve 504, since the packing 239 of the diaphragm 508 can be moved in parallel apart from the valve seat 230, the valve is stably opened and rapid exhaustion of the air can be further stabilized.

Subsequently, hereinafter, a fluid control device 600 according to a sixth preferred embodiment of the present invention will be described. This sixth preferred embodiment is different from the above described fifth preferred embodiment in regards to the structure of a valve 603, and is the same as the above described fifth preferred embodiment in other configurations.

Figure 29:
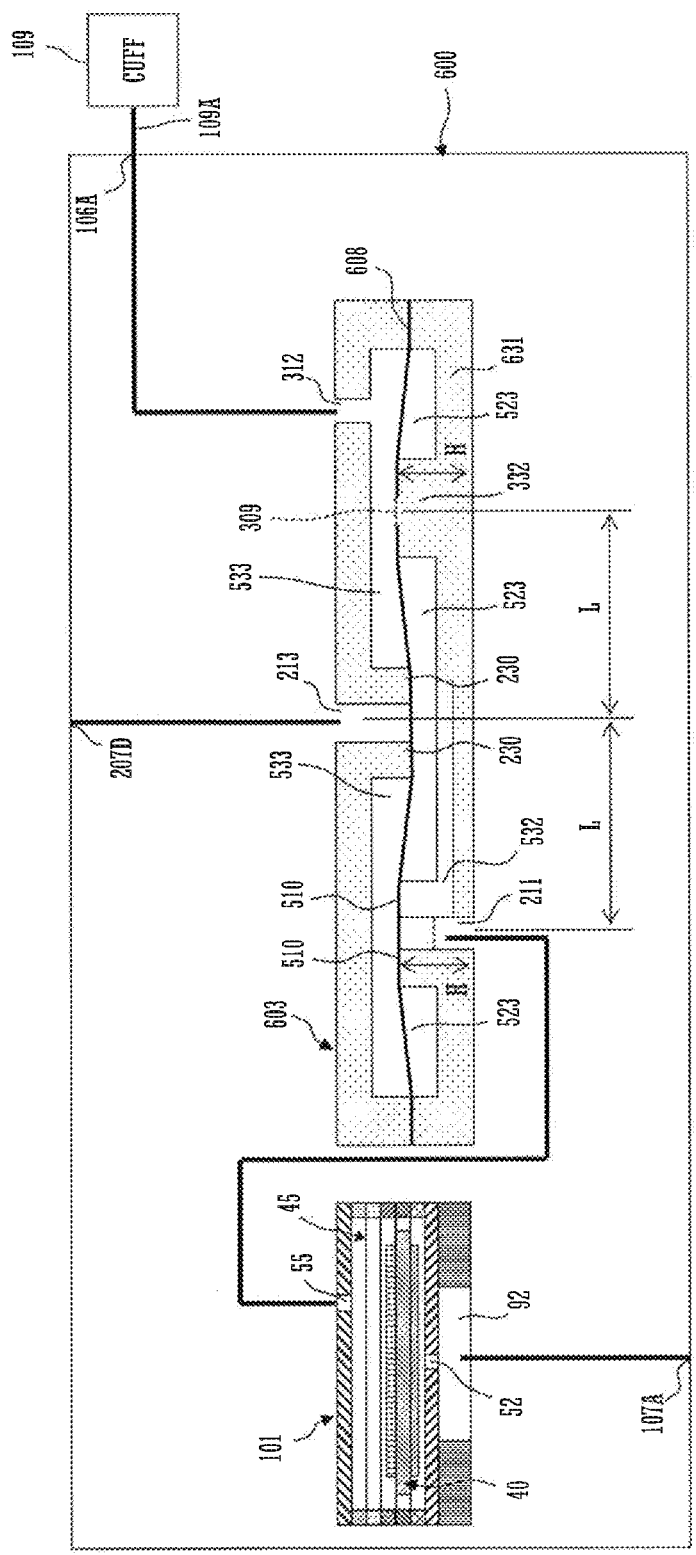
FIG. 29 is an explanatory view showing a connection relationship among a piezoelectric pump 101, a valve 603, and a cuff 109 that are included in a fluid control device 600 according to a sixth preferred embodiment of the present invention.
Figure 30:
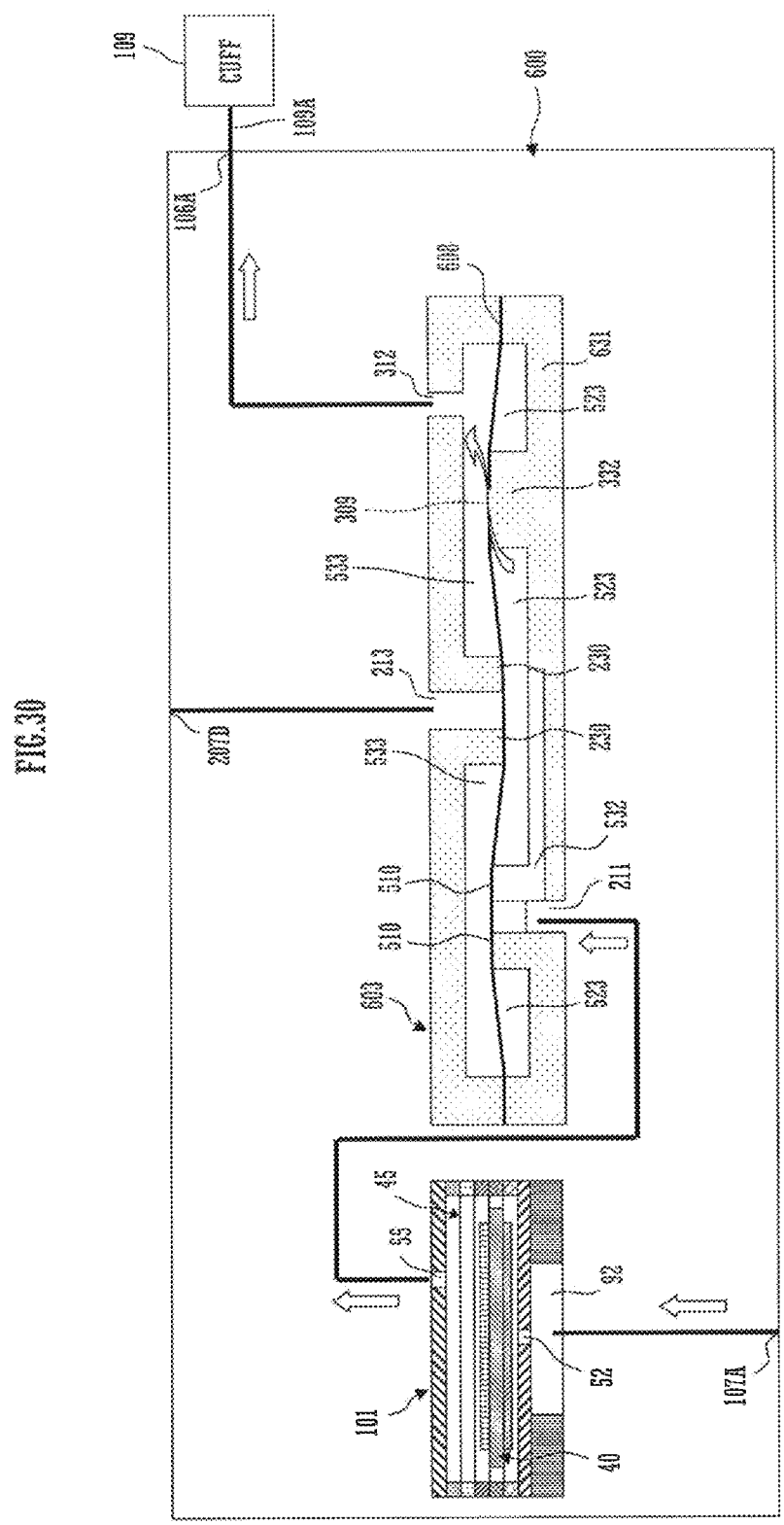
FIG. 30 is an explanatory view showing a flow of air when the piezoelectric pump 101 shown in FIG. 28 is performing a pumping operation.
Figure 31:
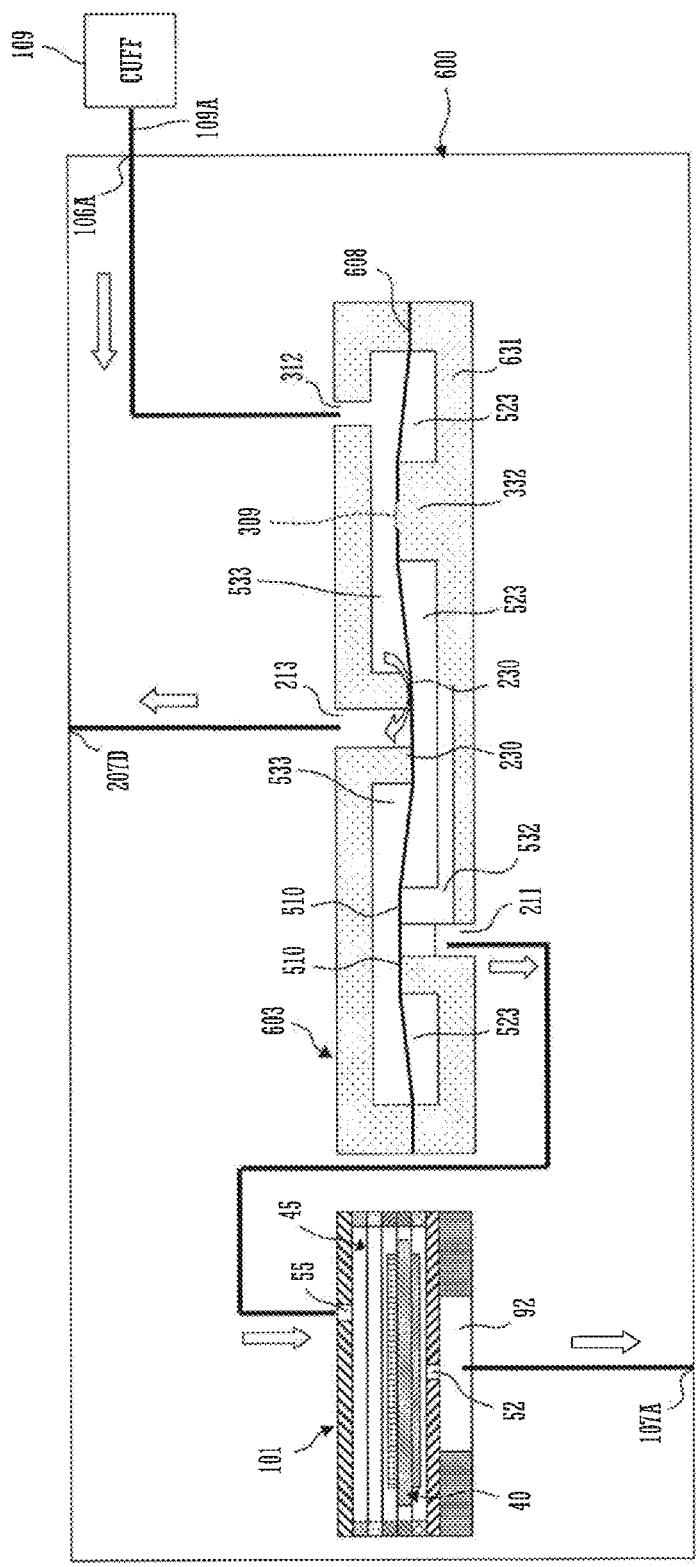
FIG. 31 is an explanatory view showing a flow of air immediately after the piezoelectric pump 101 shown in FIG. 28 stops the pumping operation.

FIG. 29 is an explanatory view showing a connection relationship among a piezoelectric pump 101, the valve 603, and a cuff 109 that are included in the fluid control device 600 according to the sixth preferred embodiment of the present invention. FIG. 30 is an explanatory view showing a flow of air when the piezoelectric pump 101 shown in FIG. 29 is performing a pumping operation. FIG. 31 is an explanatory view showing a flow of air immediately after the piezoelectric pump 101 shown in FIG. 29 stops the pumping operation. This valve 603 is a valve obtained by combining the valve 503 shown in FIG. 25 and the valve 303 shown in FIG. 16.

More specifically, the valve housing 631, in the same manner as the valve 503 as shown in FIG. 25, includes a first ventilation hole 211, a third ventilation hole 213, and valve seats 230 and 510. Furthermore, the valve housing 631, in the same manner as the valve 303 as shown in FIG. 16, includes a second ventilation hole 312 and a projecting portion 332 that is projected to the diaphragm 608 side. This projecting portion 332 and the valve seat 510 preferably have the same height H. In this regard, since the valve housing 631 including this valve seat 510 also includes a cutout 532, the first ventilation hole 211 always communicates with the lower valve chamber 523.

Here, the positional relationship among the first ventilation hole 211, the projecting portion 332, and the third ventilation hole 213 in the valve housing 631 will be described in detail. The third ventilation hole 213 is located in the center or approximate center of the valve housing 531. In addition, the first ventilation hole 211 and the projecting portion 332 are located in a position of the valve housing 631, the position being a location at which a length L from the center of the first ventilation hole 211 to the center of the third ventilation hole 213 becomes the same as a length L from the center of the third ventilation hole 213 to the center of the projecting portion 332.

Moreover, the diaphragm 608, in the same manner as the valve 303 as shown in FIG. 16, includes a hole portion 309 in a portion of a region as opposed to the projecting portion 332. The diaphragm 608 is fixed to the valve housing 631 so as to contact the valve seats 230 and 510 and make the peripheral end of the hole portion 309 contact the projecting portion 332. Accordingly, the diaphragm 608 divides the inside of the valve housing 631 and defines a lower valve chamber 523 and a ring shaped upper valve chamber 533 that communicates with the second ventilation hole 312. The projecting portion 332 is arranged in the valve housing 631 so as to pressurize the peripheral end of the hole portion 309 in the diaphragm 608.

In the above structure, the valve 603, as shown in FIG. 30 and FIG. 31, opens and closes the valve when the diaphragm 608 contacts or separates from the projecting portion 332 by a difference in pressure between the lower valve chamber 523 and the upper valve chamber 533. In addition, the valve 603 opens and closes the valve when the diaphragm 608 contacts or separates from the valve seat 230 by the difference in pressure between the upper valve chamber 533 and the lower valve chamber 523.

Therefore, the valve 603 and the fluid control device 600 according to the present preferred embodiment make it possible to achieve an effect similar to the effect that can be achieved by the above described third preferred embodiment. Furthermore, according to the valve 603 and the fluid control device 600 of the present preferred embodiment, the diaphragm 608 is in close contact with the valve seat 230 of the third ventilation hole 213 in parallel, so that the air can be prevented from leaking and rapid exhaustion of the air can be further stabilized.

Figure 32:
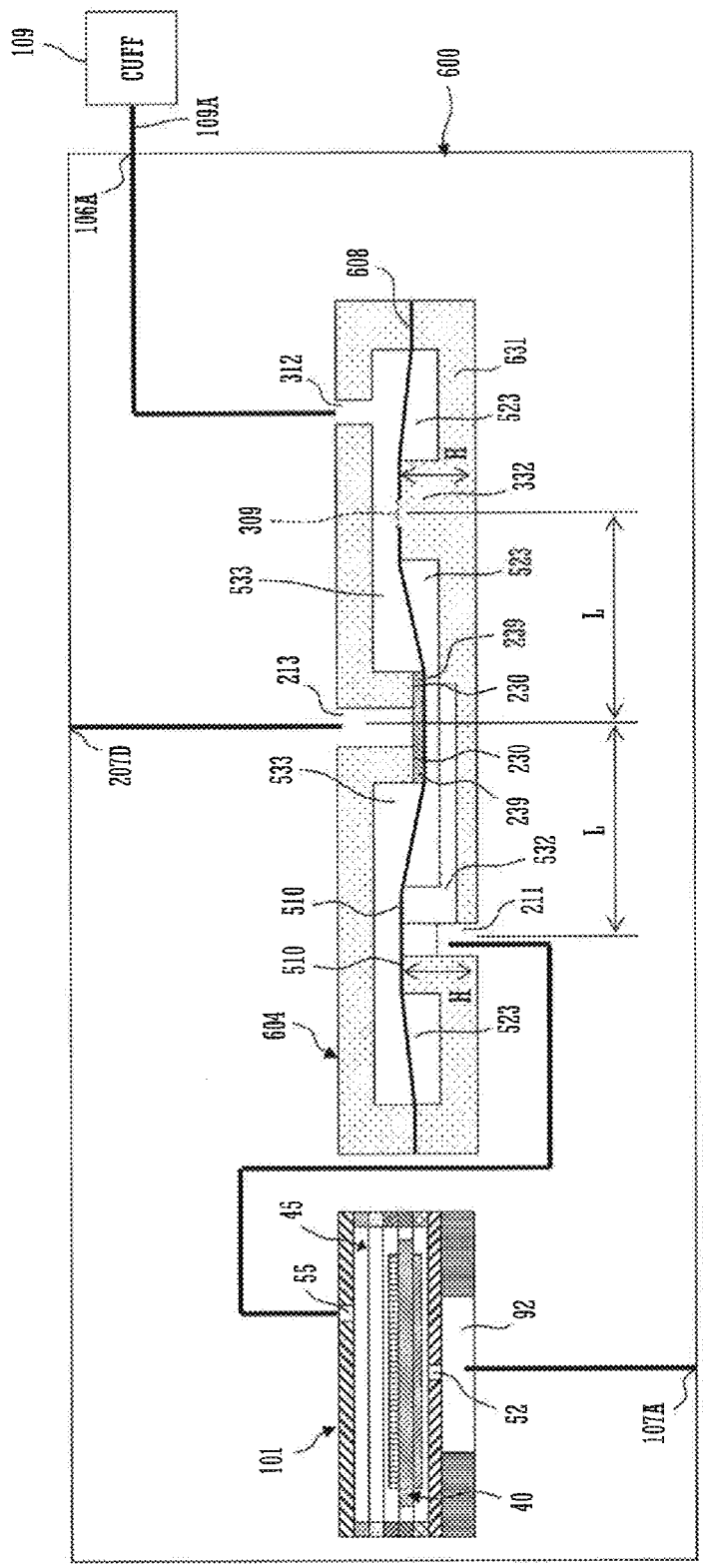
FIG. 32 is an explanatory view showing a connection relationship among a valve 604 as a modification example of the valve 603 shown in FIG. 28, the piezoelectric pump 101, and the cuff 109.

It is to be noted, also in the present preferred embodiment, as shown in FIG. 32, a disc shaped packing 239 may be provided in a position as opposed to the valve seat 230 of the diaphragm 608. The packing 239 is preferably made of an elastic body harder than the diaphragm 608. The valve 604 equipped with this packing 239 makes it possible to achieve an effect similar to the effect that can be achieved by the valve 504 equipped with the packing 239 as shown in FIG. 28.

Subsequently, hereinafter, a fluid control device 700 according to a seventh preferred embodiment of the present invention will be described. This seventh preferred embodiment is different from the above described second preferred embodiment in the structure of a valve 703, and preferably is the same or substantially the same as the above described second preferred embodiment in other configurations.

Figure 33:
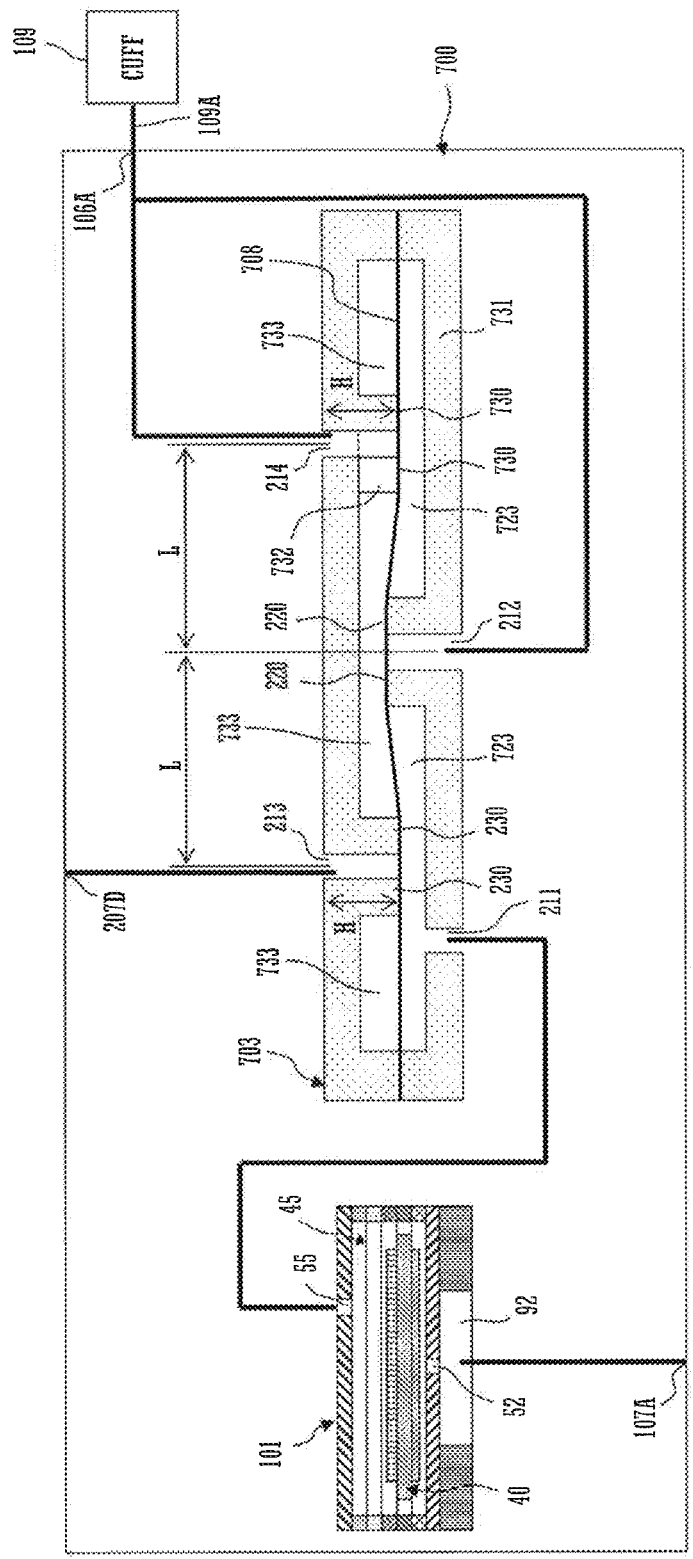
FIG. 33 is an explanatory view showing a connection relationship among a piezoelectric pump 101, a valve 703, and a cuff 109 that are included in a fluid control device 700 according to a seventh preferred embodiment of the present invention.
Figure 34:
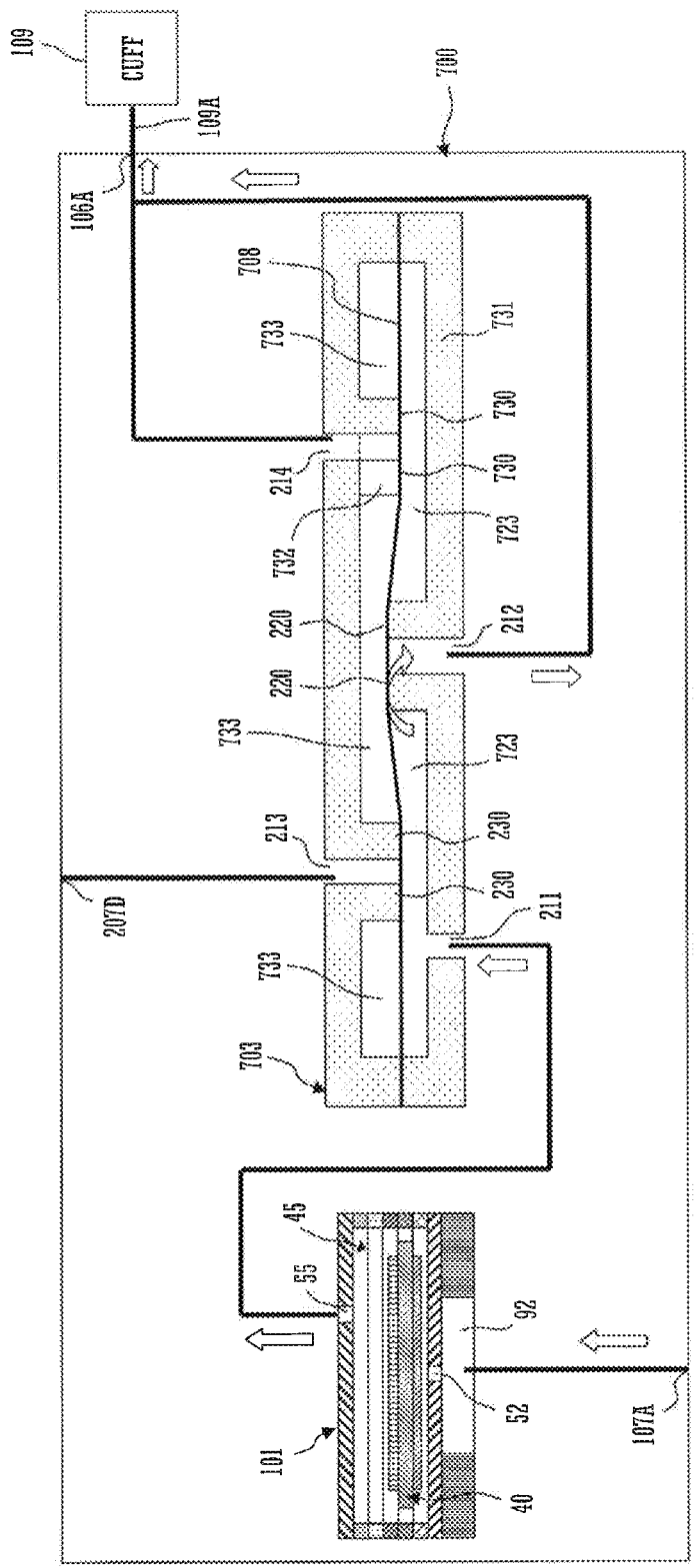
FIG. 34 is an explanatory view showing a flow of air when the piezoelectric pump 101 shown in FIG. 33 is performing a pumping operation.
Figure 35:
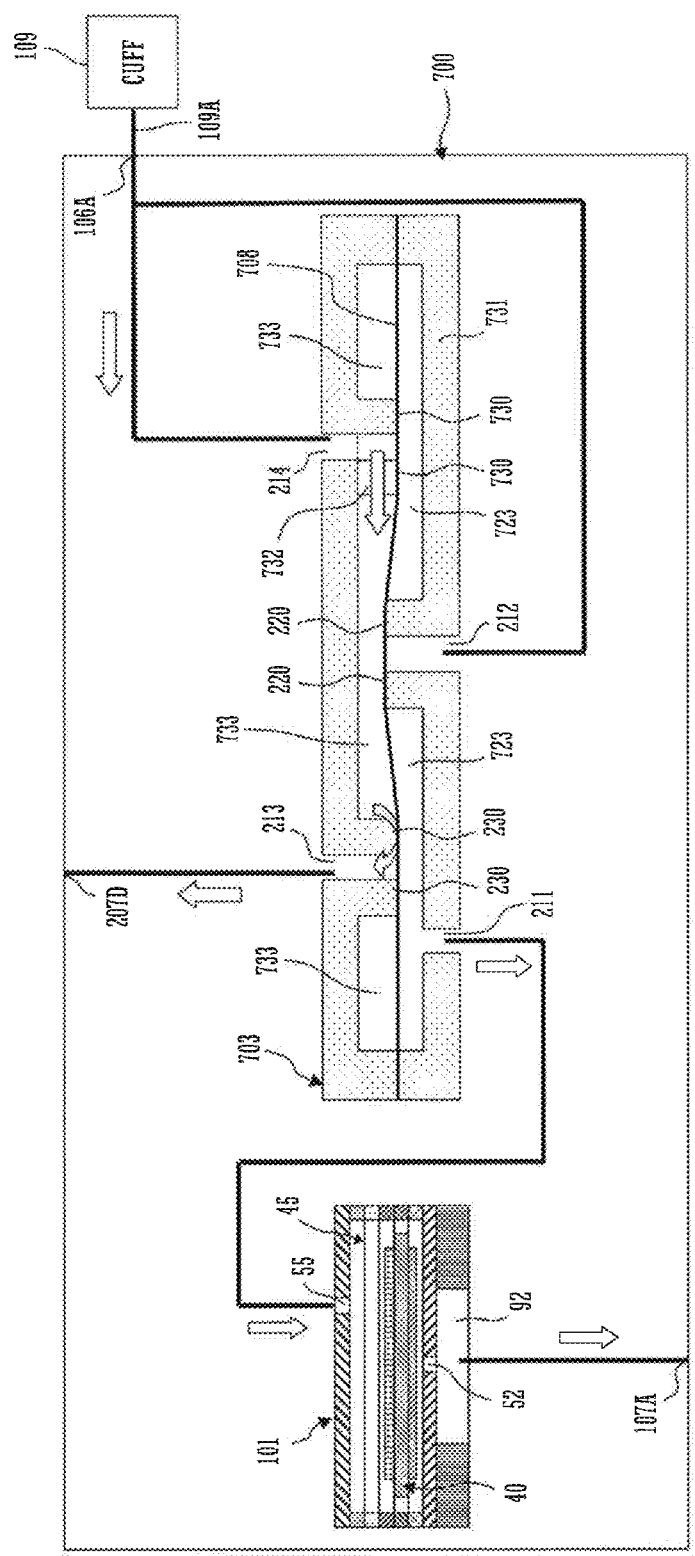
FIG. 35 is an explanatory view showing a flow of air immediately after the piezoelectric pump 101 shown in FIG. 33 stops the pumping operation.

FIG. 33 is an explanatory view showing a connection relationship among a piezoelectric pump 101, the valve 703, and a cuff 109 that are included in the fluid control device 700 according to the seventh preferred embodiment of the present invention. FIG. 34 is an explanatory view showing a flow of air when the piezoelectric pump 101 shown in FIG. 33 is performing a pumping operation. FIG. 35 is an explanatory view showing a flow of air immediately after the piezoelectric pump 101 shown in FIG. 33 stops the pumping operation. This valve 703 is a deformed version of the valve 203 shown in FIG. 13, and has a cylindrical or substantially cylindrical valve housing 731 and a diaphragm 708 that includes a circular or substantially circular thin film.

The valve housing 731, in the same manner as the valve housing 231 of the valve 203 as shown in FIG. 13, includes a first ventilation hole 211, a second ventilation hole 212, a third ventilation hole 213, a communicating hole 214, and valve seats 220 and 230.

Furthermore, the valve housing 731 includes a valve seat 730 that is projected from the peripheral end of the communicating hole 214 to the diaphragm 708 side. This valve seat 730 and the valve seat 230 have the same shape and the same height H. In this regard, since the valve housing 731 including this valve seat 730 includes a cutout 732, the communicating hole 214 always communicates with the upper valve chamber 733.

Here, the positional relationship among the second ventilation hole 212, the third ventilation hole 213, and the communicating hole 214 in the valve housing 731 will be described in detail. The second ventilation hole 212 is located in the center of the valve housing 731. In addition, the third ventilation hole 213 and the communicating hole 214 are located in a position of the valve housing 731, the position being a location at which a length L from the center of the third ventilation hole 213 to the center of the second ventilation hole 212 becomes the same as a length L from the center of the second ventilation hole 212 to the center of the communicating hole 214.

The diaphragm 708 is fixed to the valve housing 731 so as to contact the valve seats 220, 230, and 730. Accordingly, the diaphragm 708 divides the inside of the valve housing 731 and defines a ring shaped lower valve chamber 723 that communicates with the first ventilation hole 211, and a upper valve chamber 733. It should be noted, in the present preferred embodiment, the lower valve chamber 723 is equivalent to the "first region" according to a preferred embodiment of the present invention, and the upper valve chamber 733 is equivalent to the "second region" according to a preferred embodiment of the present invention.

In the above structure, the valve 703, as shown in FIG. 34 and FIG. 35, opens and closes the valve when the diaphragm 708 contacts or separates from the valve seat 220 by a difference in pressure between the lower valve chamber 723 and the upper valve chamber 733. In addition, the valve 703 opens and closes the valve when the diaphragm 708 contacts or separates from the valve seat 230 by the difference in pressure between the upper valve chamber 733 and the lower valve chamber 723.

Therefore, the valve 703 and the fluid control device 700 according to the present preferred embodiment make it possible to achieve an effect similar to the effect that can be achieved by the second preferred embodiment. Furthermore, according to the valve 703 and the fluid control device 700 of the present preferred embodiment, the diaphragm 708 is in close contact with the valve seat 220 of the second ventilation hole 212 in parallel, so that rapid exhaustion of the air can be further stabilized.

Subsequently, hereinafter, a fluid control device 800 according to an eighth preferred embodiment of the present invention will be described. This eighth preferred embodiment is different from the above described seventh preferred embodiment in the structure of a valve 803, and preferably is the same or substantially the same as the above described seventh preferred embodiment in other configurations.

Figure 36:
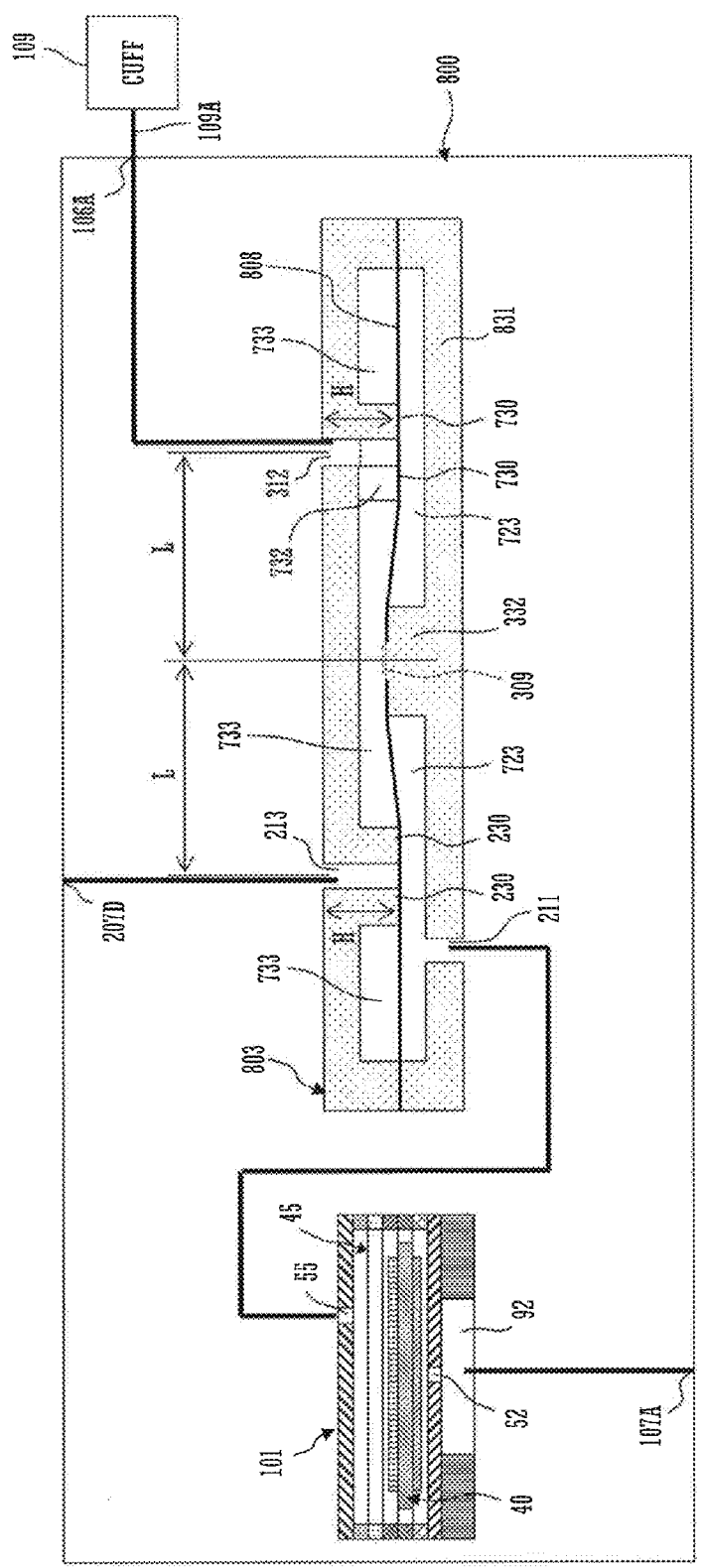
FIG. 36 is an explanatory view showing a connection relationship among a piezoelectric pump 101, a valve 803, and a cuff 109 that are included in a fluid control device 800 according to an eighth preferred embodiment of the present invention.
Figure 37:
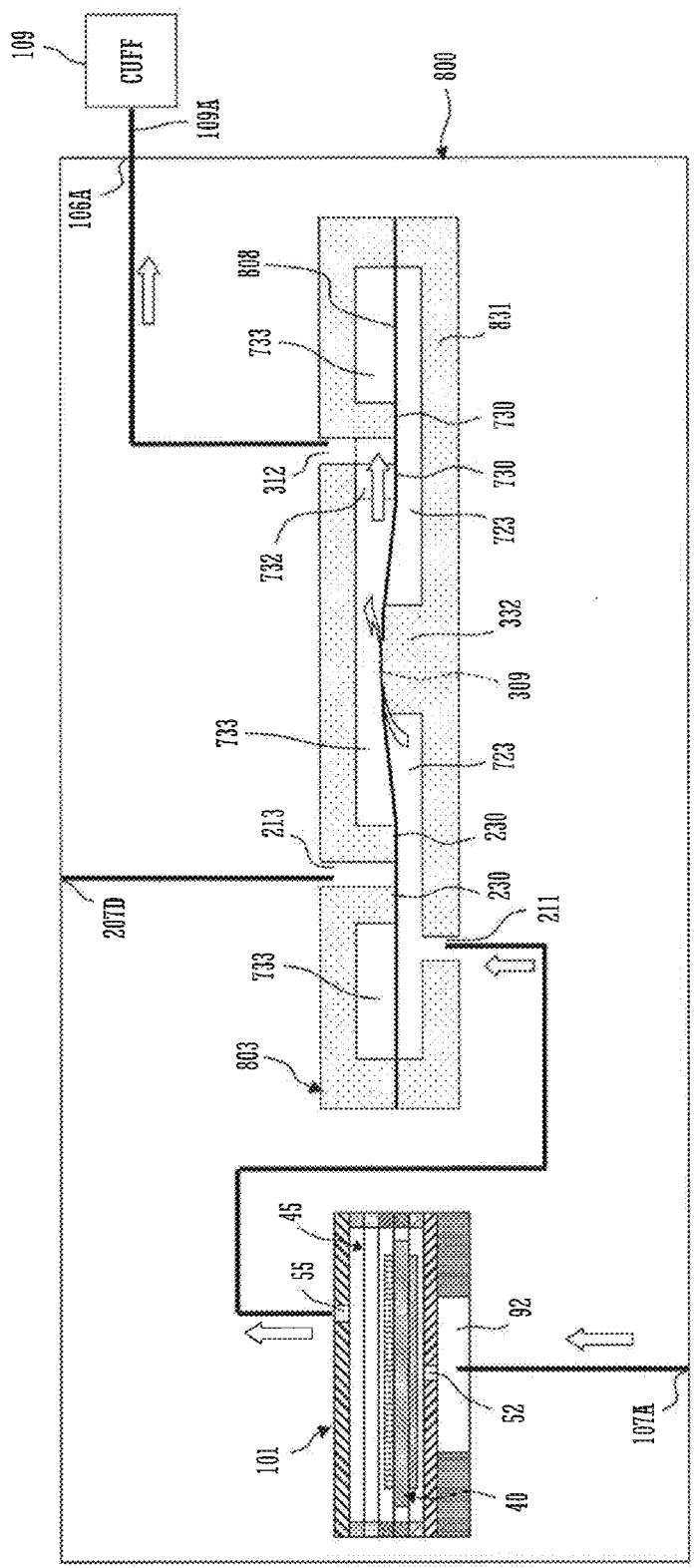
FIG. 37 is an explanatory view showing a flow of air when the piezoelectric pump 101 shown in FIG. 36 is performing a pumping operation.
Figure 38:
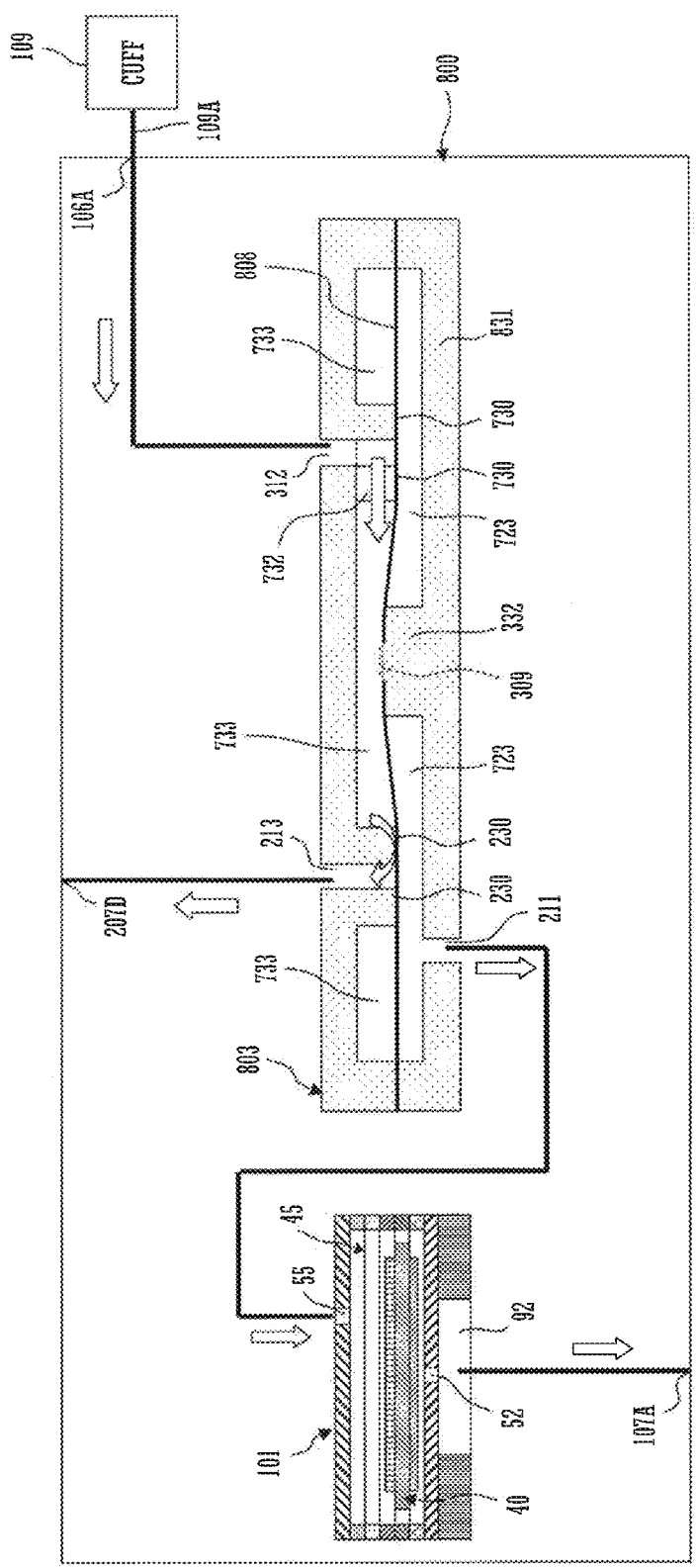
FIG. 38 is an explanatory view showing a flow of air immediately after the piezoelectric pump 101 shown in FIG. 36 stops the pumping operation.

FIG. 36 is an explanatory view showing a connection relationship among a piezoelectric pump 101, the valve 803, and a cuff 109 that are included in the fluid control device 800 according to the eighth preferred embodiment of the present invention. FIG. 37 is an explanatory view showing a flow of air when the piezoelectric pump 101 shown in FIG. 36 is performing a pumping operation. FIG. 38 is an explanatory view showing a flow of air immediately after the piezoelectric pump 101 shown in FIG. 36 stops the pumping operation. This valve 803 is a valve obtained by combining the valve 703 shown in FIG. 33 and the valve 303 shown in FIG. 16.

More specifically, the valve housing 831, in the same manner as the valve 703 as shown in FIG. 33, includes a first ventilation hole 211, a third ventilation hole 213, and valve seats 230 and 730. Furthermore, the valve housing 831, in the same manner as the valve 303 as shown in FIG. 16, includes a second ventilation hole 312 and a projecting portion 332 that is projected to the diaphragm 808 side. The valve seat 230 and the valve seat 730 preferably have the same shape and the same height H.

In this regard, since the valve housing 831 including this valve seat 730 includes a cutout 732, the second ventilation hole 312 always communicates with the upper valve chamber 733.

Here, the positional relationship among the second ventilation hole 312, the projecting portion 332, and the third ventilation hole 213 in the valve housing 831 will be described in detail. The projecting portion 332 is located in the center or approximate center of the valve housing 831. In addition, the second ventilation hole 312 and the third ventilation hole 213 are located in a position of the valve housing 831, the position being a location at which a length L from the center of the second ventilation hole 312 to the center of the projecting portion 332 becomes the same as a length L from the center of the projecting portion 332 to the center of the third ventilation hole 213.

Moreover, the diaphragm 808, in the same manner as the valve 303 as shown in FIG. 16, includes a hole portion 309 in a portion of a region as opposed to the projecting portion 332. The diaphragm 808 is fixed to the valve housing 831 so as to contact the valve seats 230 and 730 and make the peripheral end of the hole portion 309 contact the projecting portion 332. Accordingly, the diaphragm 808 divides the inside of the valve housing 831 and defines a ring shaped lower valve chamber 723 that communicates with the first ventilation hole 211, and a upper valve chamber 733. The projecting portion 332 is arranged in the valve housing 831 so as to pressurize the peripheral end of the hole portion 309 in the diaphragm 808.

In the above structure, the valve 803, as shown in FIG. 37 and FIG. 38, opens and closes the valve when the diaphragm 808 contacts or separates from the projecting portion 332 by a difference in pressure between the lower valve chamber 723 and the upper valve chamber 733. In addition, the valve 803 opens and closes the valve when the diaphragm 808 contacts or separates from the valve seat 230 by the difference in pressure between the upper valve chamber 733 and the lower valve chamber 723.

Therefore, the valve 803 and the fluid control device 800 according to the present preferred embodiment make it possible to achieve an effect similar to the effect that can be achieved by the above described third preferred embodiment. Furthermore, according to the valve 803 and the fluid control device 800 of the present preferred embodiment, the diaphragm 808 is in close contact with the projecting portion 332 in parallel, so that rapid exhaustion of the air can be further stabilized.

Subsequently, hereinafter, a fluid control device 900 according to a ninth preferred embodiment of the present invention will be described. This ninth preferred embodiment is different from the above described second preferred embodiment in that a leak valve 80 is provided, and preferably is the same or substantially the same as the above described second preferred embodiment in other configurations.

Figure 39:
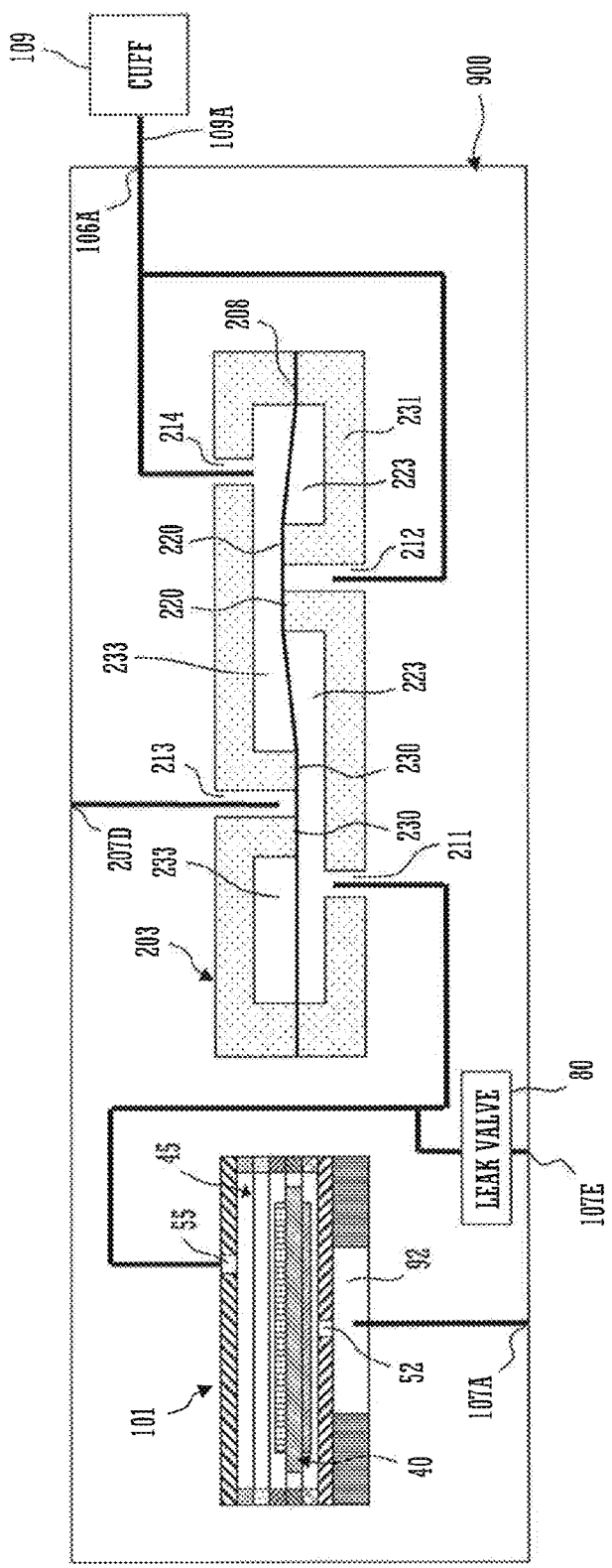
FIG. 39 is an explanatory view showing a connection relationship among a piezoelectric pump 101, a leak valve 80, a valve 203, and a cuff 109 that are included in a fluid control device 900 according to a ninth preferred embodiment of the present invention.
Figure 40A:
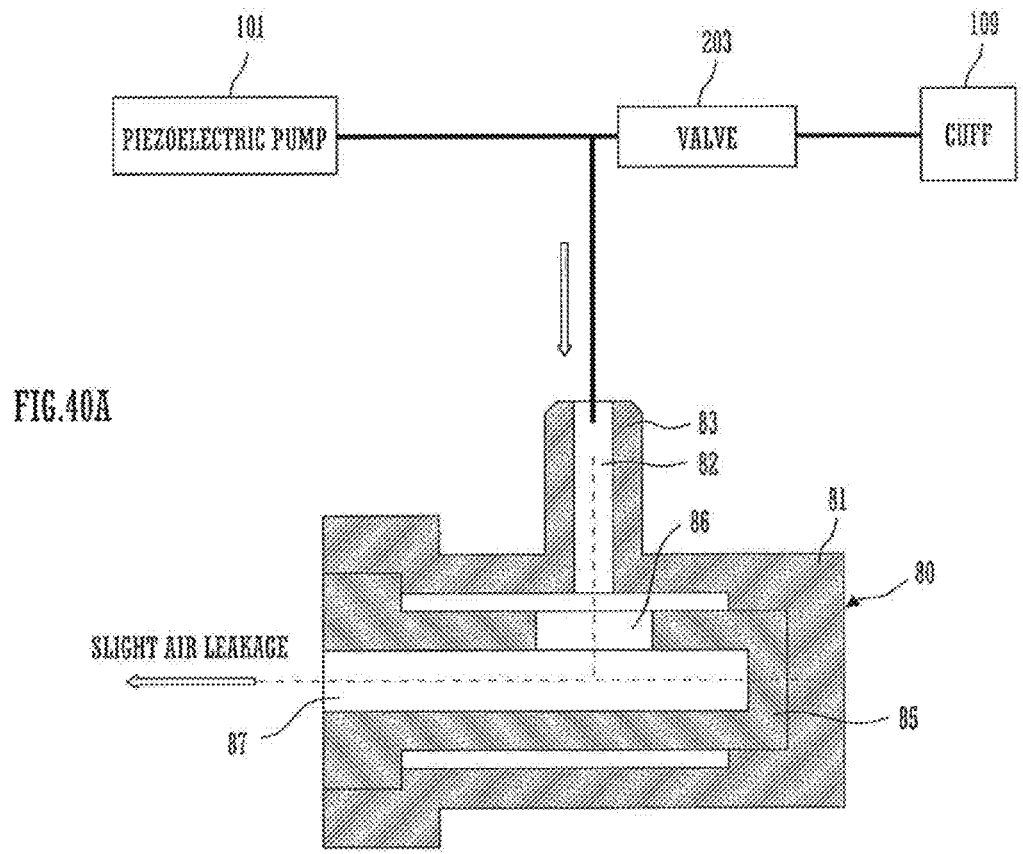
FIG. 40A is a cross sectional view of a main portion of the leak valve 80 shown in FIG. 39.
Figure 40B:
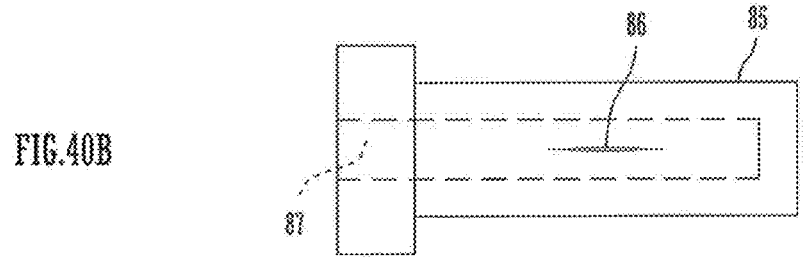
FIG. 40B is a plan view of a cylinder portion 85 shown in FIG. 40A.

FIG. 39 is an explanatory view showing a connection relationship among a piezoelectric pump 101, the leak valve 80, a valve 203, and a cuff 109 that are included in the fluid control device 900 according to the ninth preferred embodiment of the present invention. FIG. 40A is a cross sectional view of a main portion of the leak valve 80 shown in FIG. 39. FIG. 40B is a plan view of a cylinder portion 85 shown in FIG. 40A.

In the fluid control device 200 according to the above described second preferred embodiment of the present invention, as stated above, when the pumping operation of the piezoelectric pump 101 stops, the air in the pump chamber 45 and the lower valve chamber 223 is exhausted from the suction port 107A of the fluid control device 200 to the outside of the fluid control device 200 through the piezoelectric pump 101.

However, the air in the pump chamber 45 and the lower valve chamber 223 may pass through the inside of the piezoelectric pump 101 having a high flow passage resistance. Therefore, in the fluid control device 200, even if the pumping operation of the piezoelectric pump 101 stops, there is a risk that the air in the pump chamber 45 and the lower valve chamber 223 is not rapidly exhausted from the suction port 107A of the fluid control device 200 to the outside of the fluid control device 200 through the piezoelectric pump 101. Then, in this preferred embodiment, the fluid control device 900 is equipped with the leak valve 80.

More specifically, this leak valve 80, as shown in FIG. 39, is connected to a flow path that links the piezoelectric pump 101 and the valve 203. The leak valve 80, as shown in FIGS. 40A and 40B, includes a housing 81 which is made of a resin and in which a connecting portion 83 connected to the flow path is located, and a cylinder portion 85 which is made of rubber and in which a slit 86 is formed. Within the cylinder portion 85, interior space 87 is arranged to communicate through a hole portion 82 in the connection portion 83, and the slit 86.

In the present preferred embodiment, when the pumping operation of the piezoelectric pump 101 stops, the air in the pump chamber 45 and the lower valve chamber 223 is exhausted from the suction port 107A to the outside of the device through the piezoelectric pump 101 and is exhausted from an exhaust port 107E of the fluid control device 900 to the outside of the device through the leak valve 80 (see FIG. 40A). In the leak valve 80, the air that has flowed into the hole portion 82 in the connecting portion 83 flows out to the exhaust port 107E through the slit 86 and the interior space 87 of the cylinder portion 85.

Therefore, according to the valve 903 and the fluid control device 900 of this preferred embodiment, when the pumping operation of the piezoelectric pump 101 stops, the air in the pump chamber 45 and the lower valve chamber 223 is immediately exhausted, so that the responsiveness of rapid exhaustion can be improved.

Finally, the above described preferred embodiments are to be considered in all respects as illustrative and not restrictive. The scope of the present invention is defined not by above described preferred embodiments but by the claims. Further, the scope of the present invention is intended to include all modifications that come within the meaning and scope of the claims and any equivalents thereof.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A valve comprising:
    a valve housing; and
    a diaphragm that divides an inside of the valve housing and defines a first region and a second region in the valve housing; wherein
    the valve housing includes:
        a first ventilation hole to communicate with the first region;
        a second ventilation hole to communicate with the second region; and
        a third ventilation hole to communicate with a region outside of the valve housing;
    the diaphragm includes:
        a fourth ventilation hole to communicate with both the second ventilation hole and the second region;
        a first face that communicates with the first region; and
        a second face that communicates with the third ventilation hole; and
    the diaphragm is fixed to the valve housing so that, in a case in which a pressure of the first region is higher than a pressure of the second region, the diaphragm makes the first ventilation hole and the second ventilation hole communicate with each other and blocks communication between the third ventilation hole and the fourth ventilation hole; and, in a case in which the pressure of the first region is lower than the pressure of the second region, the diaphragm makes the third ventilation hole and the fourth ventilation hole communicate with each other and blocks the communication between the first ventilation hole and the second ventilation hole.

2. The valve according to claim 1, wherein
    the valve housing includes a first valve housing and a second valve housing;
    the first valve housing and the second valve housing include the first region and the second region that are defined therein by the diaphragm, respectively;

the first valve housing includes the first ventilation hole and the second ventilation hole;

the second valve housing includes:

the third ventilation hole; and a fifth ventilation hole that communicates with the first ventilation hole and the first region; and the diaphragm is fixed to the first valve housing and the second valve housing.

3. The valve according to claim 2, wherein the diaphragm further comprises:

a first diaphragm that divides an inside of the first valve housing and defines the first region and the second region in the first valve housing; and a second diaphragm that divides an inside of the second valve housing and defines the first region and the second region in the second valve housing; wherein the first diaphragm is fixed to the first valve housing so that, in the case in which the pressure of the first region is higher than the pressure of the second region, the first diaphragm opens the second ventilation hole and makes the first ventilation hole and the second ventilation hole communicate with each other; and, in the case in which the pressure of the first region is lower than the pressure of the second region, seals the second ventilation hole and blocks the communication between the first ventilation hole and the second ventilation hole; and the second diaphragm is fixed to the second valve housing so that, in the case in which the pressure of the first region is higher than the pressure of the second region, the second diaphragm seals the third ventilation hole and blocks the communication between the third ventilation hole and the fourth ventilation hole; and, in the case in which the pressure of the first region is lower than the pressure of the second region, the second diaphragm opens the third ventilation hole and makes the third ventilation hole and the fourth ventilation hole communicate with each other.

4. The valve according to claim 3, wherein the first valve housing further comprises:

a sixth ventilation hole that communicates with the second ventilation hole and the second region; wherein the first diaphragm divides the inside of the first valve housing and defines:

a first valve chamber that communicates with the first ventilation hole and defines a portion of the first region; and a second valve chamber that communicates with the sixth ventilation hole and defines a portion of the second region.

5. The valve according to claim 4, wherein the first valve housing further comprises:

a valve seat that projects from a peripheral end of the second ventilation hole toward the first diaphragm; wherein the first diaphragm is arranged in contact with the valve seat.

6. The valve according to claim 5, wherein the first diaphragm opens and closes the valve by contacting or separating from the valve seat by a difference in pressure between the first valve chamber and the second valve chamber.

7. The valve according to claim 5, wherein the valve seat is arranged in the first valve housing so as to pressurize the first diaphragm.

8. The valve according to claim 3, wherein the first diaphragm and the second diaphragm are defined by one sheet of a diaphragm sheet.

9. The valve according to claim 2, wherein the first valve housing and the second valve housing are arranged in one valve housing.

10. The valve according to claim 1, wherein the valve housing further comprises a projecting portion that projects toward the diaphragm in the first region; and the diaphragm includes the fourth ventilation hole in a portion of a region that is opposed to the projecting portion.

11. A fluid control device comprising:

a pump including:

a pump chamber; and a suction hole and a discharge hole that communicate with each other through the pump chamber;

the valve according to claim 1, wherein the discharge hole of the pump is connected to the first ventilation hole;

the pump makes the pressure of the first region higher than the pressure of the second region by performing a pumping operation; and the pump makes the pressure of the first region lower than the pressure of the second region when stopping the pumping operation.

12. A fluid control device comprising:

a pump including:

a pump chamber; and a suction hole and a discharge hole that communicate with each other through the pump chamber;

the valve according to claim 2; wherein the discharge hole of the pump is connected to the first ventilation hole;

the pump makes the pressure of the first region higher than the pressure of the second region by performing a pumping operation; and the pump makes the pressure of the first region lower than the pressure of the second region when stopping the pumping operation.

13. A fluid control device comprising:

a pump including:

a pump chamber; and a suction hole and a discharge hole that communicate with each other through the pump chamber;

the valve according to claim 3; wherein the discharge hole of the pump is connected to the first ventilation hole;

the pump makes the pressure of the first region higher than the pressure of the second region by performing a pumping operation; and the pump makes the pressure of the first region lower than the pressure of the second region when stopping the pumping operation.

14. A fluid control device comprising:

a pump including:

a pump chamber; and a suction hole and a discharge hole that communicate with each other through the pump chamber;

the valve according to claim 4; wherein the discharge hole of the pump is connected to the first ventilation hole;

the pump makes the pressure of the first region higher than the pressure of the second region by performing a pumping operation; and the pump makes the pressure of the first region lower than the pressure of the second region when stopping the pumping operation.

15. A fluid control device comprising:
a pump including:
- a pump chamber; and
- a suction hole and a discharge hole that communicate with each other through the pump chamber;

the valve according to claim 5; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

16. A fluid control device comprising:
a pump including:
- a pump chamber; and
- a suction hole and a discharge hole that communicate with each other through the pump chamber;

the valve according to claim 6; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

17. A fluid control device comprising:
a pump including:
- a pump chamber; and
- a suction hole and a discharge hole that communicate with each other through the pump chamber;

the valve according to claim 7; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

18. A fluid control device comprising:
a pump including:
- a pump chamber; and
- a suction hole and a discharge hole that communicate with each other through the pump chamber;

the valve according to claim 8; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

19. A fluid control device comprising:
a pump including:
- a pump chamber; and
- a suction hole and a discharge hole that communicate with each other through the pump chamber;

the valve according to claim 9; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

20. A fluid control device comprising:
a pump including:
- a pump chamber; and
- a suction hole and a discharge hole that communicate with each other through the pump chamber;

the valve according to claim 10; wherein
the discharge hole of the pump is connected to the first ventilation hole;
the pump makes the pressure of the first region higher than the pressure of the second region by performing a pumping operation; and
the pump makes the pressure of the first region lower than the pressure of the second region when stopping the pumping operation.

* * * * *